US 009513216B2

United States Patent
Ohba et al.

(10) Patent No.: US 9,513,216 B2
(45) Date of Patent: Dec. 6, 2016

(54) OPTICAL SENSOR AND IMAGE FORMING APPARATUS

(71) Applicants: Yoshihiro Ohba, Miyagi (JP); Satoru Sugawara, Miyagi (JP); Toshihiro Ishii, Miyagi (JP); Fumikazu Hoshi, Miyagi (JP)

(72) Inventors: Yoshihiro Ohba, Miyagi (JP); Satoru Sugawara, Miyagi (JP); Toshihiro Ishii, Miyagi (JP); Fumikazu Hoshi, Miyagi (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/977,166

(22) Filed: Dec. 21, 2015

(65) Prior Publication Data

US 2016/0109364 A1    Apr. 21, 2016

Related U.S. Application Data

(63) Continuation of application No. 13/879,451, filed as application No. PCT/JP2011/077875 on Nov. 25, 2011, now Pat. No. 9,267,886.

(30) Foreign Application Priority Data

Nov. 26, 2010 (JP) .................................. 2010-263079
Mar. 15, 2011 (JP) .................................. 2011-056234
(Continued)

(51) Int. Cl.
G01J 4/00 (2006.01)
G01J 1/42 (2006.01)
(Continued)

(52) U.S. Cl.
CPC ....... *G01N 21/4738* (2013.01); *G01B 11/0625* (2013.01); *G01N 21/21* (2013.01);
(Continued)

(58) Field of Classification Search
CPC .... G01N 21/17; G01N 21/4738; G01N 21/57; G01N 21/21; G01N 21/55; G03G 15/5029; G03G 15/6591; G03G 2215/00616; G01B 11/0625
(Continued)

(56) References Cited

U.S. PATENT DOCUMENTS 4,276,910 A     7/1981  Eichenberger
5,329,338 A  *  7/1994  Merz .................. G03G 15/5029
                                              250/559.16
(Continued)

FOREIGN PATENT DOCUMENTS

JP    H09-222361    8/1997
JP    H10-160687    6/1998
(Continued)

OTHER PUBLICATIONS

Jun. 9, 2016 European search report in connection with European patent application No. 11842775.6.
(Continued)

*Primary Examiner* — Tarifur Chowdhury
*Assistant Examiner* — Sunghee Y Gray
(74) *Attorney, Agent, or Firm* — Cooper & Dunham LLP

(57) ABSTRACT

In an optical sensor, a light emission system emits an irradiated light of a linear polarization in a first polarization direction toward a surface of a target object having a sheet shape from an incident direction which is inclined with respect to a normal direction of the surface. A first light detection system includes a first light detector arranged on a first light path of a specular reflected light, which is emitted from the light emission system and is specularly reflected from the target object. A second light detection system includes a second light detector arranged on a second light path of a diffuse reflected light which is diffusely reflected
(Continued)

from an incident plane on the target object. The second light detector receives second light passed by an optical element which passes a linear polarization component of a second polarization direction perpendicular to the first polarization direction.

9 Claims, 51 Drawing Sheets

(30) Foreign Application Priority Data

Jul. 20, 2011 (JP) .................................. 2011-158527
Aug. 4, 2011 (JP) .................................. 2011-171101

(51) Int. Cl.
| | | |
|---|---|---|
| *F21V 1/00* | (2006.01) | |
| *H04L 12/18* | (2006.01) | |
| *H04H 20/71* | (2008.01) | |
| *G01N 21/47* | (2006.01) | |
| *G01N 21/55* | (2014.01) | |
| *G01B 11/06* | (2006.01) | |
| *G01N 21/21* | (2006.01) | |
| *G01N 21/57* | (2006.01) | |
| *G03G 15/00* | (2006.01) | |
| *G03G 15/04* | (2006.01) | |
| *G03G 15/32* | (2006.01) | |
| *G03G 15/043* | (2006.01) | |

(52) U.S. Cl.
CPC ............. *G01N 21/55* (2013.01); *G01N 21/57* (2013.01); *G03G 15/0409* (2013.01); *G03G 15/04072* (2013.01); *G03G 15/326* (2013.01); *G03G 15/5029* (2013.01); *G03G 15/5062* (2013.01); *G01N 2021/4792* (2013.01); *G01N 2201/06113* (2013.01); *G03G 15/0435* (2013.01)

(58) Field of Classification Search
USPC ......... 356/369; 399/45; 359/204.1; 362/227, 362/235; 370/254, 312; 250/216, 208.2
See application file for complete search history.

(56) References Cited

U.S. PATENT DOCUMENTS

| | | |
|---|---|---|
| 6,630,995 B1 | 10/2003 | Hunter |
| 6,731,886 B2 | 5/2004 | Takeda |
| 6,975,663 B2 | 12/2005 | Sekiya et al. |
| 7,002,527 B2 | 2/2006 | Sugawara |
| 7,245,647 B2 | 7/2007 | Jikutani et al. |
| 7,978,739 B2 | 7/2011 | Sugawara et al. |
| 8,035,676 B2 | 10/2011 | Harasaka et al. |
| 8,111,725 B2 | 2/2012 | Ishii et al. |
| 2003/0058433 A1 | 3/2003 | Almogy et al. |
| 2003/0193034 A1 | 10/2003 | Tullis et al. |
| 2004/0129901 A1 | 7/2004 | Yamaguchi et al. |
| 2004/0136738 A1 | 7/2004 | Yamamoto et al. |
| 2005/0051743 A1 | 3/2005 | Yamaguchi et al. |
| 2006/0093010 A1 | 5/2006 | Sekiya et al. |
| 2007/0046713 A1 | 3/2007 | Miyahara et al. |
| 2007/0273886 A1 | 11/2007 | Matsumoto et al. |
| 2009/0059216 A1 | 3/2009 | Shibata et al. |
| 2009/0295902 A1 | 12/2009 | Sato et al. |
| 2010/0119262 A1 | 5/2010 | Omori et al. |
| 2010/0328747 A1 | 12/2010 | Jikutani et al. |
| 2011/0037825 A1 | 2/2011 | Jikutani et al. |
| 2011/0058174 A1 | 3/2011 | Ramachandran et al. |
| 2011/0109713 A1 | 5/2011 | Yamaguchi et al. |
| 2011/0115872 A1 | 5/2011 | Harasaka et al. |
| 2011/0170155 A1 | 7/2011 | Jikutani et al. |
| 2011/0211869 A1 | 9/2011 | Shouji et al. |
| 2011/0228035 A1 | 9/2011 | Ishii et al. |
| 2011/0261139 A1 | 10/2011 | Hoshi et al. |
| 2011/0267415 A1 | 11/2011 | Ohba et al. |
| 2012/0207589 A1* | 8/2012 | Fridthjof ................ B64D 15/20 415/121.3 |

FOREIGN PATENT DOCUMENTS

| | | |
|---|---|---|
| JP | H11-249353 | 9/1999 |
| JP | 2002-340518 | 11/2002 |
| JP | 2003-292170 | 10/2003 |
| JP | 2004-184203 | 7/2004 |
| JP | 2004-212088 | 7/2004 |
| JP | 2005-083850 | 3/2005 |
| JP | 2005-156380 | 6/2005 |
| JP | 2005-529313 | 9/2005 |
| JP | 2006-062842 | 3/2006 |
| JP | 2007-093586 | 4/2007 |
| JP | 2007093586 | 4/2007 |
| JP | 2007-315761 | 12/2007 |
| JP | 2008-8740 | 1/2008 |
| JP | 2008-249714 | 10/2008 |
| JP | 2008-311499 | 12/2008 |
| JP | 2009-58303 | 3/2009 |
| JP | 2010-197482 | 9/2010 |
| JP | 2012-127937 | 7/2012 |

OTHER PUBLICATIONS

Japanese official action dated Jun. 11, 2015 in corresponding Japanese Patent Application No. 2011-158527.
Japanese official action dated Jul. 7, 2015 in corresponding Japanese Patent Application No. 2011-171101.
International Search Report Issued Feb. 28, 2012 in PCT/JP2011/077875 filed on Nov. 25, 2011.
Korean official action dated Jul. 22, 2014 and English translation in corresponding Korean patent application No. 10-2013-7013230.

* cited by examiner

INTERNAL DIFFUSE REFLECTED LIGHT

SURFACE DIFFUSE REFLECTED LIGHT

SURFACE SPECULAR REFLECTED LIGHT

RECORDING PAPER

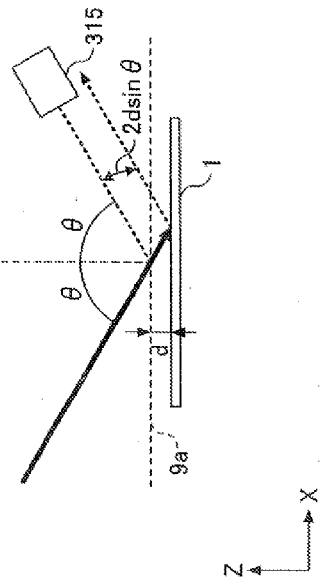
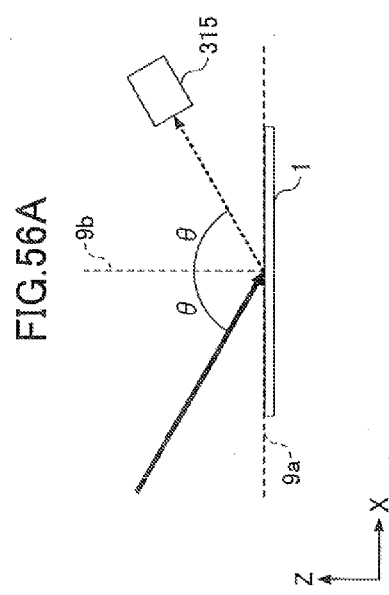
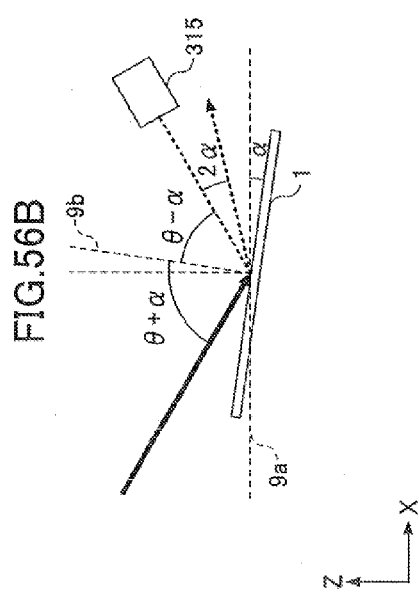

OPTICAL SENSOR AND IMAGE FORMING APPARATUS

CROSS-REFERENCE TO RELATED APPLICATIONS

This application is a Rule 1.53(b) continuation of application Ser. No. 13/879,451 filed as a National Stage under 35 U.S.C. 371 of International Application No. PCT/JP2011/077875 filed Nov. 25, 2011, claiming the priority of Japanese Patent Applications Nos. 2010-263079, 2011-056234, 2011-158527 and 2011-171101 filed on Nov. 26, 2010, Mar. 15, 2011, Jul. 20, 2011 and Aug. 4, 2011, respectively.

TECHNICAL FIELD

The present invention generally relates to an optical sensor and an image forming apparatus.

BACKGROUND ART

In an image forming apparatus using an electrophotographic method such as a digital copier, a laser printer, and the like, a toner image is transferred onto a recording medium such as a recording paper and is fixed by heating and pressurizing at a predetermined condition, thereby an image is formed on the recording medium such as the recording paper. In the image forming apparatus, a condition such as a heat amount, pressure, and the like to fix the toner image is considered. Especially, in a case of forming an image at high quality, it is needed to individually set a condition for fixing the toner image depending on types of the recording medium.

An image quality for recording to the recording medium is greatly influenced by material, thickness, temperature, smoothness, a coating state, and the like. For example, regarding the smoothness, a fixing rate of toner is lower at a concave portion due to an irregularity of the recording medium depending on the condition for fixing the image. As a result, it is not possible to acquire a high quality image. That is, if the image is not fixed at a condition corresponding to the smoothness of the recording medium to which the image is formed, an irregular color or the like is caused. The high quality image is not acquired.

On the other hand, a concurrent recent development of the image forming apparatus and diversity of expressing method, there are more than several hundred types of the recording papers used as the recording medium. Moreover, a large variety of names exist depending on grammage, thickness, or the like for each type of the recording paper. Therefore, in order to form the high quality image, it is required to set a fixing condition and the like in detail based on the type, the name, and the like of the recording paper used as the recording medium.

Various types of the recording media have been marketed such as a special paper being embossed on a surface of a paper as well as a plain paper, a coated paper such as a gloss coated paper, a matt coated paper, and an art coated paper, an OHP (Over Head Projector) sheet, and the like. The types of the recording media are increased. Also, there are many types of the recording media other than the recording paper and the like.

Currently, settings such as the fixing condition and the like related to the image forming apparatus are needed to be set by a user. Thus, the user is required to have knowledge related to the various types of the recording media. Also, if the user needs to set the fixing condition, the user may feel that it is too complex to perform printing or the like. Moreover, if there is an error in the fixing condition set by the user, it is difficult to acquire the high quality image desired by the user.

Thus, technologies have been inspected, related to a sensor for identifying the recording medium such as the recording paper to automatically specify the type of the recording medium, and an image forming apparatus mounting the sensor for identifying the recording medium to automatically specify the type of the recording medium.

For the sensor for identifying the recording medium, Japanese Laid-Open Patent Application No. 2002-340518 discloses a method for detecting friction resistance of a surface by using a stylus type probe. Japanese Laid-open Patent Application No. 2003-292170 discloses a method for detecting stiffness of the recording medium by a pressure sensor or the like. Also, Japanese Laid-open Patent Application No. 2005-156380 discloses a method for imaging the surface of the recording medium by using an image pick up element such as an area sensor or the like, and specifying the type of the recording medium based on the picked up image, as a method for identifying the recording medium without contact with the recording medium.

Also, a method using a reflected light may be considered as another method for identifying the recording medium without contact. In the method using the reflected light, light emitted from a light source such as a light emitting diode (LED) or the like is emitted to the recording medium of a target to be identified, and the name or the like of the recording medium is specified based on a reflected light amount from the recording medium. The following three types of methods are presented, related to the method using the reflected light.

In a first method, as described in Japanese Laid-open Patent Application No. H10-160687, the reflected light amount is detected in a specular reflection direction of a light on a surface of the recording medium, and the name or the like of the recording medium is specified based on the reflected light amount in the specular reflection direction.

In a second method, as described in Japanese Laid-open Patent Application No. 2006-062842, multiple light amount detectors are provided to detect a amount of light reflected in the specular reflection direction of light illuminating the surface of the recording medium, to also detect a light amount of a diffuse reflection, and to identify the name or the like of the recording medium based on the detected light amount in the specular reflection direction and the light amount in the diffuse reflection direction.

In a third method, as described in Japanese Laid-open Patent Application No. H11-249353, light reflected in the specular reflection direction of light illuminating the surface of the recording medium is separated by a polarization beam splitter. Light amount of the separated light is measured and the name or the like of the recording medium is determined based on the measured light amount.

However, Japanese Laid-open Patent Application No. 2002-340518 and No. 2003-292170 disclose a contact method. Thus, there is a problem in which the surface of the recording paper or the like as the recording medium may become damaged. In Japanese Laid-open patent Application 2005-156380, it is possible to determine the smoothness or the like of the recording medium but it is difficult to determine the thickness or the like of the recording medium.

In Japanese Laid-open Patent Applications No. H10-160687, No. 2006-062842, and No. H11-249353, it is possible to roughly determine the recording medium, but it is not possible to determine the thickness or the like of the recording medium in detail. In an apparatus for determining material of a sheet member disclosed in Japanese Laid-open Patent Application No. H10-160687 and apparatuses disclosed in Japanese Laid-open Patent Application No. 2006-062842 and No. H11-249353, it is possible to identify (determine) only a non-coated paper, a coated paper, and an OHP sheet but it is not possible to specify the name of the recording medium for a high quality image formation.

In addition to the above described methods, a sensor or the like using an ultrasound or the like may be mounted to identify the recording medium in detail. By mounting multiple sensors having different schemes, a size of the image forming apparatus is increased, and also, another problem is caused such as higher costs of manufacture.

For the sensor for detecting a surface state of a printing sheet based on the reflected light amount, a semiconductor laser may be used as a light source to improve an S/N (Signal to Noise ratio). In this case, a speckle pattern may occur when a light flux illuminates a rough surface such as the surface of the printing sheet. Since the speckle pattern is different depending on portions illuminated by the light flux, dispersion of detection light at a light receiving part is caused and accuracy of identifying the printing paper may be degraded. Accordingly, the LED or the like has been generally used as the light source.

DISCLOSURE OF THE INVENTION

The present invention solves or reduces one or more of the above problems.

In an aspect of this disclosure, there is provided an optical sensor, including a light emission system configured to omit an irradiated light of a linear polarization in a first polarization direction toward a surface of a target object having a sheet shape from an incident direction which is inclined with respect to a normal direction of the surface; a first light detection system configured to include a first light detector arranged on a first light path of a specular reflected light, which is emitted from the light emission system and is specularly reflected from the target object; and a second light detection system configured to include a second light detector arranged on a second light path of a diffuse reflected light which is diffusely reflected from an incident plane on the target object, the second light detector receiving second light passed by an optical element which passes a linear polarization component of a second polarization direction perpendicular to the first polarization direction.

In another aspect of this disclosure, there is provided an optical sensor, including multiple measurement systems each configured to include a light emission system configured to emit first light of a linear polarization in a first polarization direction to a recording medium; a specular reflected light detection system configured to detect specular reflected light which is specularly reflected from the recording medium in the first light emitted from the light emission system; and a diffuse reflected light detection system configured to include an optical device for passing second light in a second polarization direction perpendicular to the first polarization direction, to detect diffuse reflected light which is diffusely reflected from the recording medium in the first light emitted from the light emission system.

In a further aspect of this disclosure, there is provided an optical sensor, including multiple light emission systems each configured to emit first light of a linear polarization in a first polarization direction to a recording medium; multiple specular reflected light detection systems each configured to detect specular reflected light which is specularly reflected from the recording medium in the first light emitted from a respective light emission system in the multiple light emission systems; and a diffuse reflected light detection system configured to include an optical device for passing second light in a second polarization direction perpendicular to the first polarization direction, to detect diffuse reflected light which is diffusely reflected from the recording medium in the first light emitted from the respective light emission system.

BRIEF DESCRIPTION OF THE DRAWINGS

Other objects, features, and advantages of the present invention will become more apparent from the following detailed description when read in conjunction with the accompanying drawings, in which:

FIG. 56A through 56C are diagrams for explaining a change of a detected light amount due to a displacement between a measurement plane and the surface of the recording paper in the eighth embodiment.

BEST MODE FOR CARRYING OUT THE INVENTION

Figure 1C:
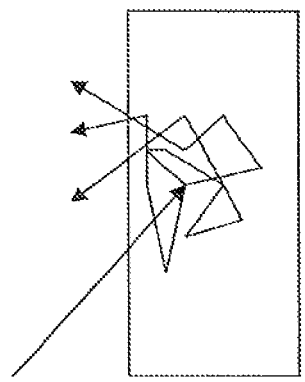
FIG. 1A, FIG. 1B, and FIG. 1C are diagrams for explaining reflected light from a recording paper.

In the following, an embodiment of the present invention will be described with reference to the accompanying drawings. The same component parts and the like are indicated by the same reference numerals and the explanation thereof will be omitted.

First Embodiment

Classification of Reflected Light

Figure 1B:
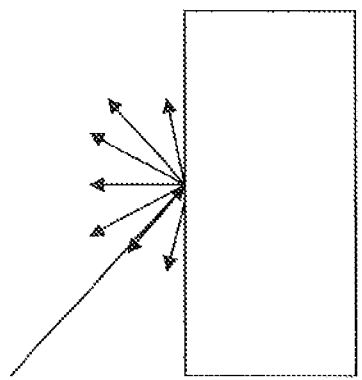
Figure 1A:
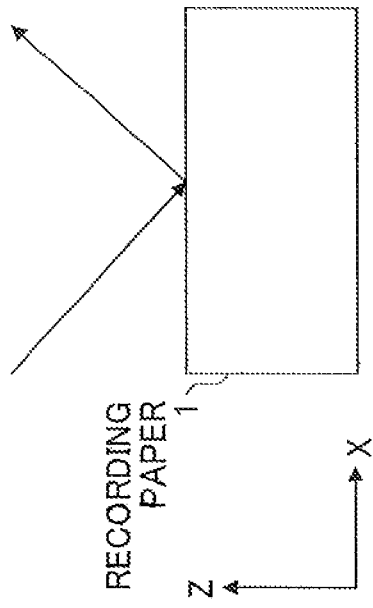

First, reflected light in a case of emitting light onto a recording medium such as a recording paper or the like will be described with reference to FIG. 1A, FIG. 1B, and FIG. 1C. In the case of emitting the light onto a recording paper 1 as the recording medium, it is possible to separate reflected light into light reflected from a surface of the recording paper 1 and light reflected inside the recording medium. Moreover, it is possible to separate the light reflected from the surface of the recording paper 1 into specular reflected light and diffuse reflected light. In the first embodiment, light specularly reflected from the surface of the recording paper 1 illustrated in FIG. 1A is described as a surface specular reflected light. Light diffusely reflected from the surface of the recording paper 1 is illustrated in FIG. 1B. In the first embodiment, a case of the recording medium being the recording paper 1 to which the light is illustrated will be described. Alternatively, the recording medium may be a resin film, a fabric, a skin, and the like. A similar measurement and the like may be performed.

The surface of the recording paper 1 as the recording medium is formed by flat portions and slope portions. Smoothness of the recording paper 1 is determined by a ratio of the flat portions and the slope portions. Light reflected on the flat portions becomes the surface specular reflected light, and light reflected on the slopes becomes the surface diffuse reflected light. The greater the smoothness of the recording medium increases a light amount of the surface specular reflected light.

On the other hand, in a case in which the recording medium is the recording paper 1, light reflected inside the recording paper 1 includes the diffuse reflected light alone due to a multiple reflection caused by fabric formed by the recording paper 1. The light diffusely reflected inside the recording paper 1 illustrated in FIG. 1C is described as internal diffuse reflected light.

As illustrated, light reflected from the recording paper 1 as the recording medium includes the surface specular reflected light, the surface diffuse reflected light, and the internal diffuse reflected light. In the light, a polarization direction of light reflected on the surface of the recording paper 1 is not rotated. That is, the polarization directions of the surface specular reflected light and the surface diffuse reflected light are not changed. In order to rotate the polarization direction of emitted light, the light is needed to be reflected at a slope surface in a rotation direction with respect to a light axis. Accordingly, in a case in which a light source at which the light is emitted, an area illuminated by the light, and a photodetector exist on the same plane, the reflected light in which the polarization direction is rotated is not reflected to a direction in which the photodetector exists. Thus, the photodetector may not detect the reflected light. On the contrary, the internal diffuse reflected light is regarded as light multiplication reflected due to the fabric inside the recording paper 1. Thus, the polarization direction is rotated with respect to light emitted from the light source.

As described above, an optical device for separating lights having different polarization directions is provided in front of the photodetector. The optical device may be a polarizing filter. Thus, it is possible to detect light having a polarization component in a perpendicular direction to a component of a linear polarization emitted from the light source. It is possible to separate and detect the internal diffuse reflected light alone. Based on a detected light amount of the internal diffuse reflected light, it is possible to determine a type and thickness of the recording paper 1 as the recording medium.

Figure 2:
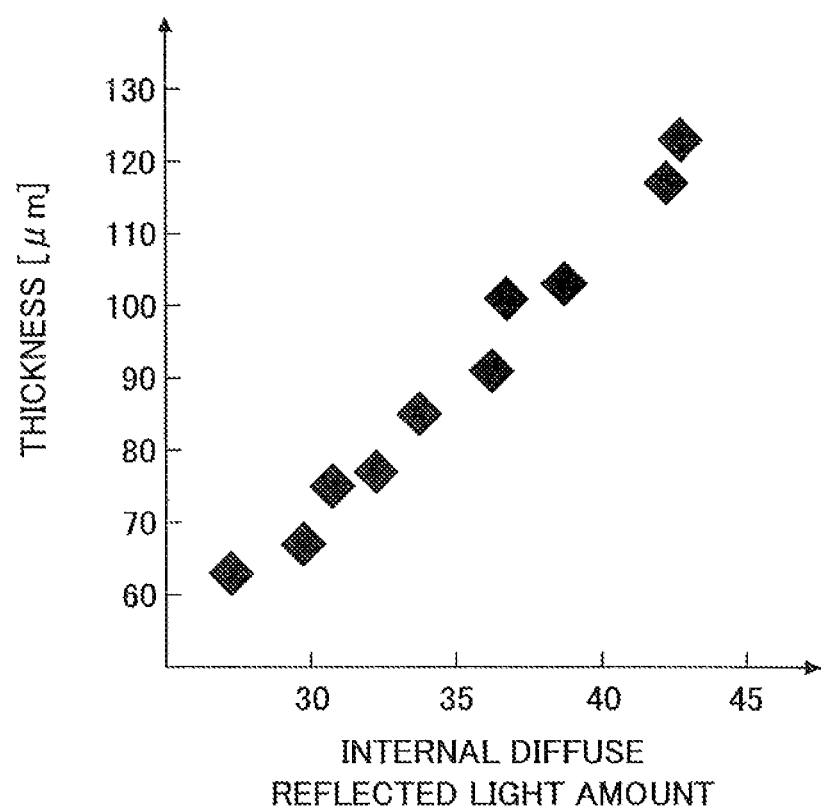
FIG. 2 is a diagram illustrating a correlation between a light amount of an internal diffuse reflection and thickness of the recording paper.
Figure 3:
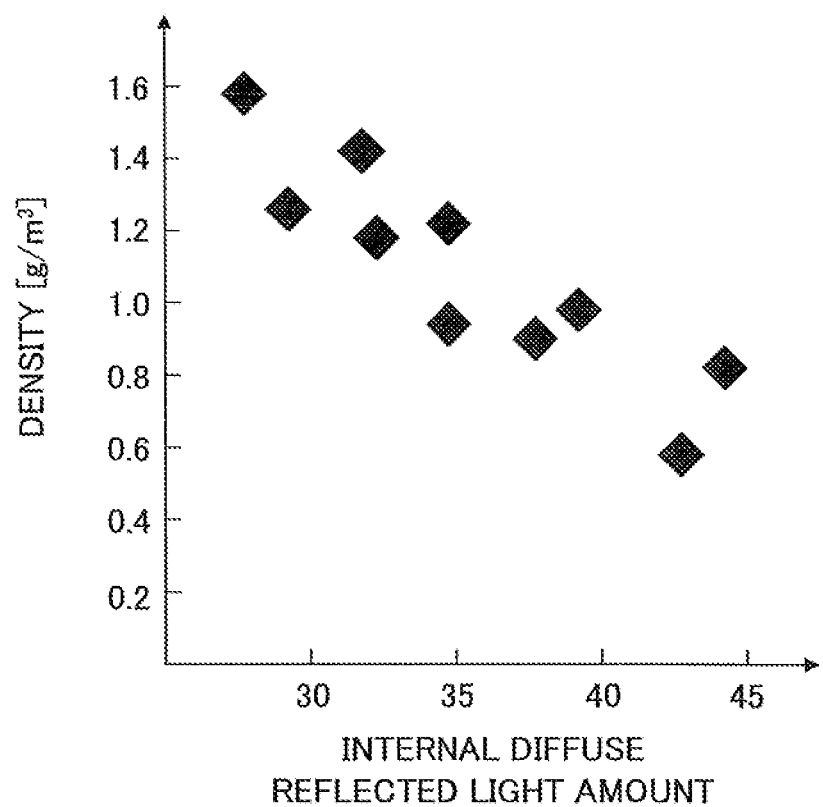
FIG. 3 is a diagram illustrating a correlation between the light amount of the internal diffuse reflection and a density of the recording paper.

In detail, as illustrated in FIG. 2, there is a correlation between the light amount of an internal diffuse reflection and the thickness of the recording paper 1. The thicker the recording paper 1, the increased the light amount of an internal diffuse reflection. Accordingly, it is possible to determine the thickness of the recording paper 1 based on the light amount of the internal diffuse reflection. Moreover, as illustrated in FIG. 3, there is the correlation between the light amount of the internal diffuse reflection and density of the recording paper 1. The higher the density of the recording paper 1, the increased the light amount of the internal diffuse reflection. Accordingly, it is possible to determine the density of the recording paper 1 based on the light amount of the internal diffuse reflection. FIG. 2 illustrates a measurement result in a case of multiple different thicknesses of the recording paper 1. FIG. 3 illustrate another measurement result in a case of multiple different densities of the recording paper 1.

(Grain of Recording Paper)

The recording paper 1 as the recording medium is produced so as to be conveyed in one direction in a production stage. A orientation of the fabric forming the recording paper 1, called a grain, is caused on the recording paper 1. The orientation of the fabric is formed along a direction of conveyance of the recording paper 1 in the production stage. Therefore, based on a direction of emitting the light, it is possible to acquire different reflection features even in a case of the same recording paper 1, and to determine the name or the like of the recording paper 1 based on the different reflection features. That is, it is possible to determine the name of the recording paper 1 based on a difference of the grain.

Figure 4A:
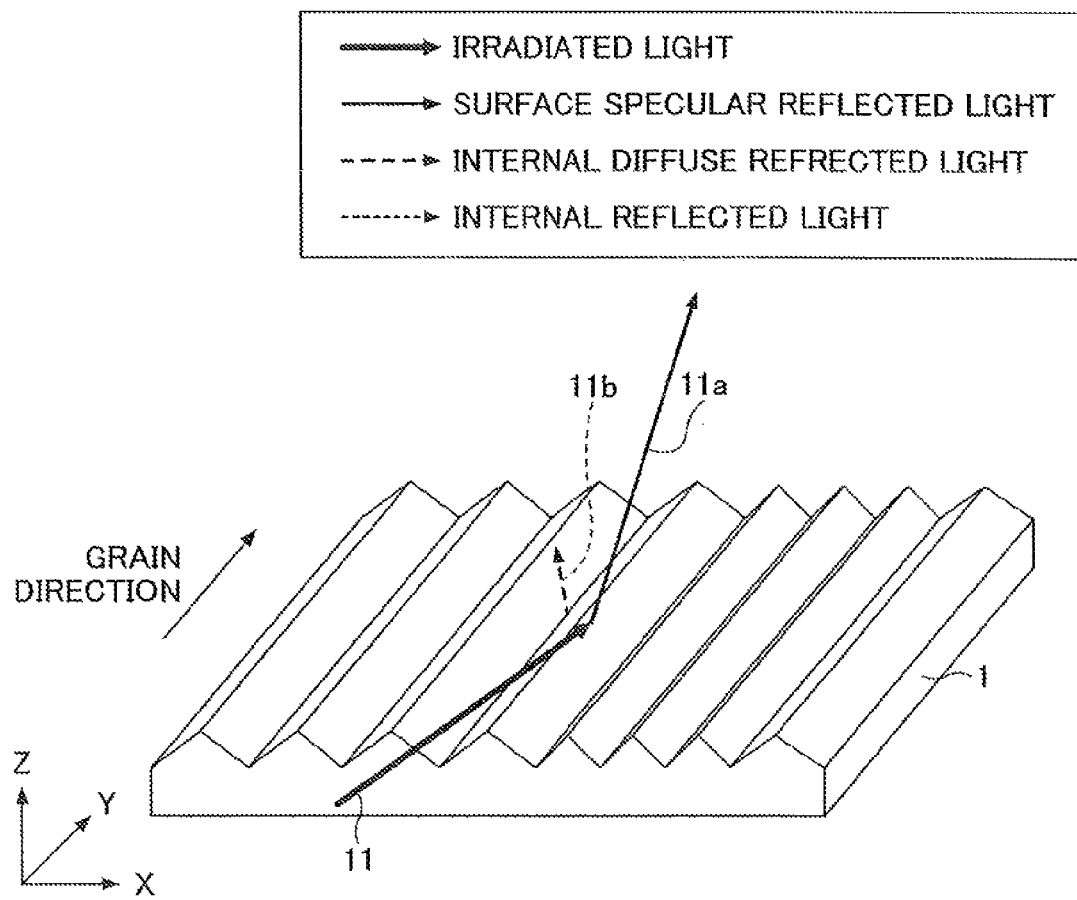
FIG. 4A and FIG. 4B are diagrams for explaining the reflected light in a case of emitting light along a grain of the recording paper.
Figure 4B:
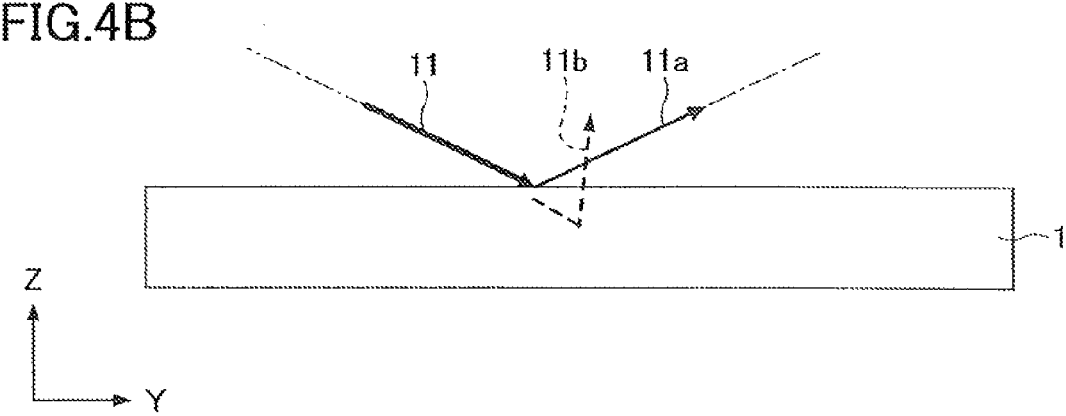

A determination of the recording paper 1 will be described with reference to FIG. 4A and FIG. 4B, and FIG. 5A and FIG. 5B. In FIG. 4A and FIG. 4B, and FIG. 5A and FIG. 5B, it is assumed that an orientation of concavity and convexity due to the grain is 100% for the recording paper 1. The grain is formed according to a Y axis direction. As illustrated in FIG. 4A and FIG. 4B, in a case of emitting light 11 in a direction along the grain of the recording paper 1, that is, in a case in which the grain of the recording paper 1 and a light path of the light 11 are on the same plane, in other words, in a case in which the light path of the light 11 exits on a plane parallel to a YZ plane, a surface of the recording paper 1 may be regarded as a flat and smooth plane, and the surface diffuse reflected light may hardly occur. Also, as the diffuse reflected light, an internal diffuse reflected light 11b, which is diffusely reflected inside the recording paper 1, occurs. Accordingly, in this case, reflected light of the light 11 is almost a surface specular reflected light 11a. FIG. 4A is a perspective diagram illustrating a state in which reflected light of the light 11 illuminating the recording paper 1 is almost the surface specular reflected light 11a. FIG. 4B is a cross-sectional diagram illustrating a surface along the grain of the recording paper 1. That is, in FIG. 4B, a cross-sectional surface in the YZ plane is illustrated.

Figure 5A:
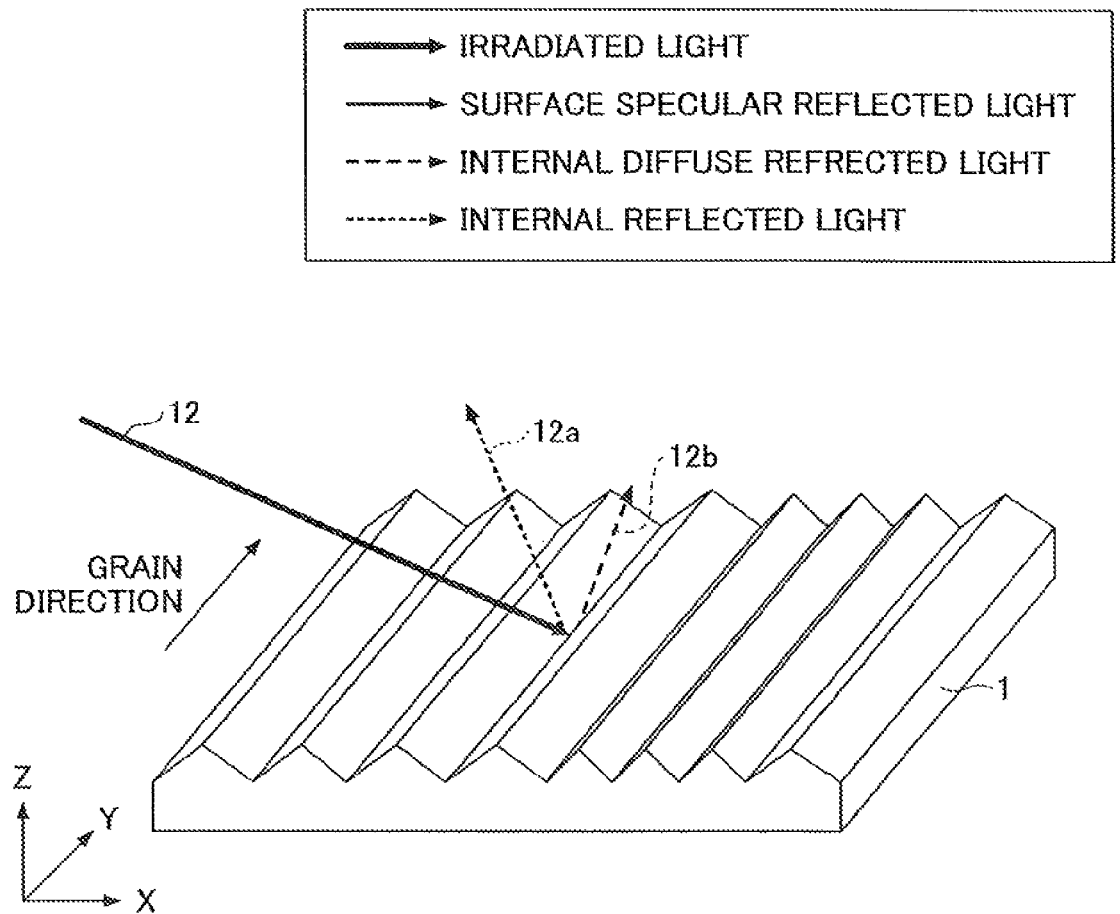
FIG. 5A and FIG. 5B are diagrams for explaining the reflected light in a case of emitting the light perpendicularly to the grain of the recording paper (part 1).
Figure 5B:
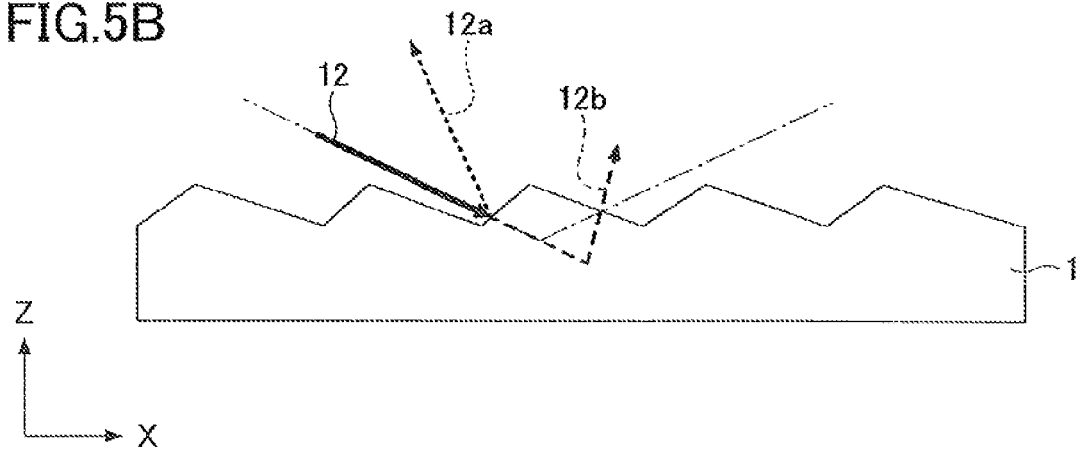

Next, as illustrated in FIG. 5A and FIG. 5B, in a case of emitting light 12 in a perpendicular direction to the grain of the recording paper 1, that is, in a case in which the light path of the light 12 illuminated on the recording paper 1, an illuminated surface may be regarded as a slope portion on an irregular surface of the recording paper 1. Thus, the light 12 is diffusely reflected from the surface and the specular reflection hardly occurs. Thus, the light amount of a surface diffuse reflected light 12a is increased. In this case, also, as the diffuse reflected light, the internal diffuse reflected light 12b, which is diffusely reflected inside the recording paper 1, occurs but the light amount is less. Thus, the reflected light of the light 12 is almost the surface diffuse reflected light 12a. FIG. 5A is a perspective diagram illustrating a state in which the reflected light of the light 12 illuminating the recording paper is mostly the surface diffuse reflected light 12a. FIG. 5B is a cross-sectional sectional diagram illustrating a surface perpendicular to the grain of the recording paper 1. That is, in FIG. 5B, a cross-sectional surface in an XZ plane is illustrated.

Figure 6A:
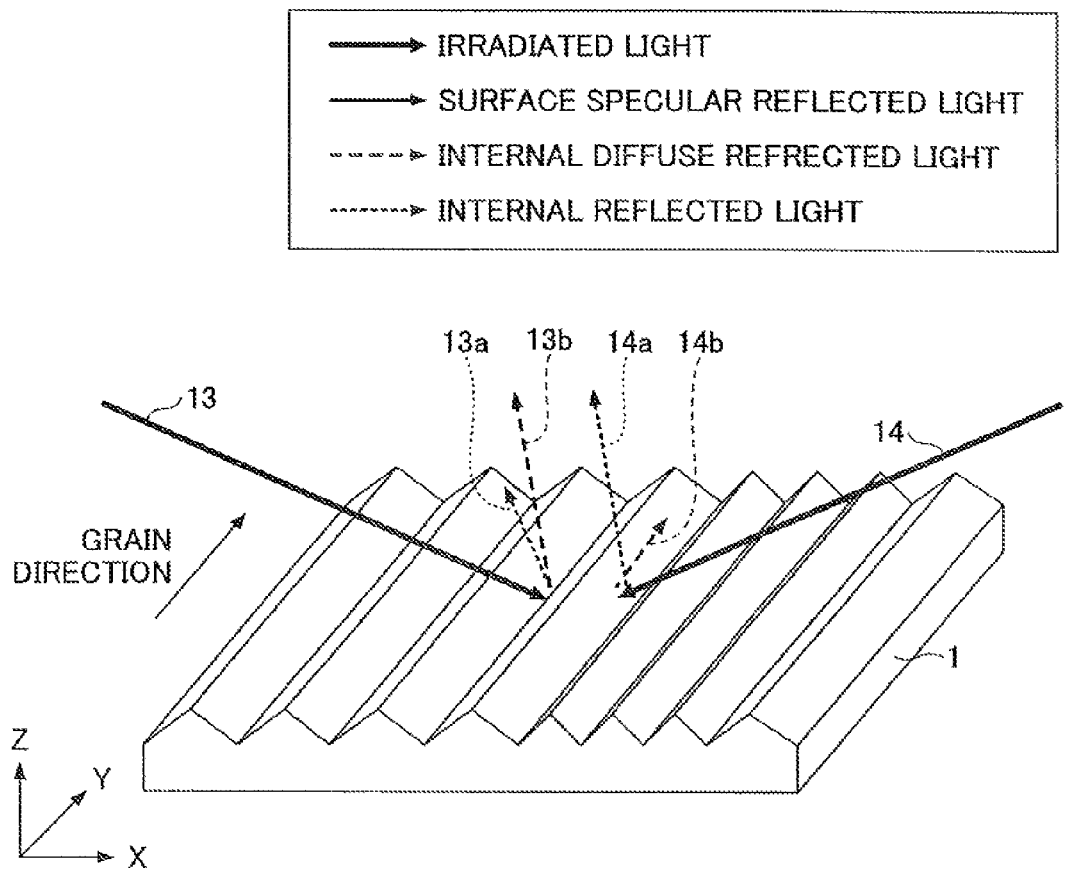
FIG. 6A and FIG. 6B are diagrams for explaining the reflected light in the case of emitting the light perpendicularly to the grain of the recording paper (part 2).
Figure 6B:
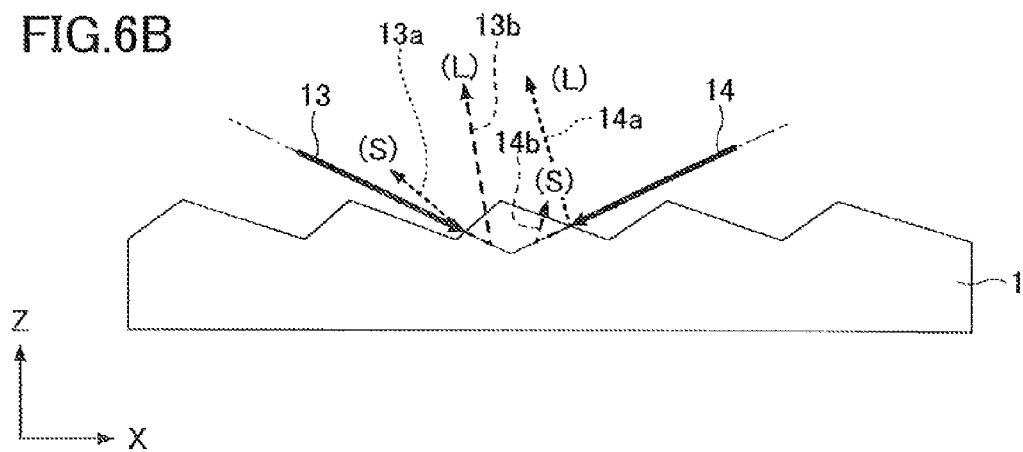

Moreover, in a case of emitting light in the perpendicular direction to the grain of the recording paper 1, the light amounts of the surface diffusion reflected light and the internal diffuse reflected light, which are detected, are varied depending on an incident direction of the light toward the recording paper 1. In detail, as illustrated in FIG. 6A and FIG. 6B, by emitting light 13 and light 14 which are opposite to each other in the perpendicular direction to the grain of the recording paper 1, the light amounts of the surface diffuse reflected light and the internal diffuse reflected light are varied. Variations of the light amounts are caused by different slopes at both ends of the grain of the recording paper 1. The different slopes at both ends of the grain of the recording paper 1 have been investigated.

That is, even in a case of similarly emitting light at approximately the same angle with respect to the recording paper 1 in the perpendicular direction to the grain of the recording paper 1, if the incident direction of the light illuminating the recording paper 1 is changed, an incident angle becomes different due to the slope on the irregular surface of the recording paper 1. In detail, light 13 emitted to the recording paper 1 enters at an angle near a vertical angle with respect to the slope of the recording paper 1. Thus, the light entering inside the recording paper 1 is increased, a surface diffuse reflected light 13a is increased, and an internal diffuse reflected light 13b is increased. Also, since light 14 enters the recording paper 1 at an angle sharper than an angle of the light 13 with respect to the slope of the recording paper 1, light entering inside the recording paper 1 is decreased. Thus, a surface diffuse reflected light 14a is increase and a internal diffuse reflected light 14b is increased. This state occurs in a case in which the light enters perpendicularly to the grain of the recording paper 1. In a case of emitting the light along the grain of the recording paper 1, even if the incident direction of the light is changed, a ratio or the like of the surface specular reflected light and the internal diffuse reflected light may not be varied.

As described above, summarizing a relationship between the incident direction of the light entering the recording paper 1 and the reflected light, the ratio between the surface specular reflected light and the surface diffuse reflected light in light emitted along the grain of the recording paper 1 is different from that in light emitted perpendicularly to the grain of the recording paper 1. Moreover, in a case in which the incident direction of the light entering the recording paper 1 is an opposite direction, that is, in a case in which an angle of the incident direction of entering light is 180°, as long as the light enters along the grain of the recording paper 1, a different incident direction of the entering light may not influence the light amounts of the surface specular reflected light and the internal diffuse reflected light. However, in a case in that the light enters perpendicularly to the grain of the recording paper 1, when the incident direction of the light is changed, the light amounts of the surface specular reflected light and the internal diffuse reflected light are varied.

In the above explanation, it is assumed that the orientation of the grain of the recording paper 1 is 100%. On an actual recording paper, the grain is formed. A degree and the like of the orientation of the grain are different depending on the production stage, a production condition, and the like. Based on characteristics of the actual recording paper, the reflected light of the light entering the recording paper 1 is classified into the surface specular reflected light, the surface diffuse reflected light, and the internal diffuse reflected light, and respective light amounts are measured. By this manner, it is possible to determine the name and the type of the recording paper 1 in detail, and to improve accuracy of determining the recording paper 1.

(Detection Accuracy of Internal Diffuse Reflected Light)

A high accurate detection method of the internal diffuse reflected light will be described. In order to detect the internal diffuse reflected light at higher accuracy, first, it is required to exclude a component of the surface specular reflected light in a detection direction at least. However, it is difficult to completely exclude light other than light of the linear polarization in one direction alone in an actual irradiation system. That is, it is difficult to leave light of the linear polarization in a first polarization direction alone. The reflected light or the surface of the recording paper 1 includes a component in a second polarization direction perpendicular to the first polarization direction.

In detail, in a case in which a photodetector is arranged at a location where the surface specular reflected light is detected and the light amount of the component of the light in the second polarization direction by using an optical filter, if the component of the light in the second polarization direction is included in the light emitted on the recording paper 1, this component is also detected by the photodetector. Thus, the light amount of the internal diffuse reflected light may not be precisely detected. In this case, since the light amount of the internal diffuse reflected light is generally smaller, the light amount of the component of the light in the second polarization direction included in the light emitted onto the recording paper 1 may be greater than that of the internal diffuse reflected light. Also, it may be possible to make the light emitted onto the recording paper 1 be a perfect light in the first polarization direction. In this case, it is required to sue a polarization filter having a higher extinction ratio. Thus, this configuration costs more.

Next, when the internal diffuse reflected light is detected, it is required to perform the detection in a direction approximately perpendicular with respect to the surface of the recording paper 1. Since the internal diffuse reflected light may be regarded as perfectly diffuse reflected light, the light amount of reflection with respect to the detection direction may be approximated to a Lambert distribution. The reflected light amount becomes the greatest in the direction perpendicular to the surface of the recording paper 1. The light amount of the internal diffuse reflected light is a slight amount. In view of improving a S/N, by providing the photodetector to be a light receiving part in the direction perpendicular to the surface of the recording paper 1, it is possible to improve the accuracy. In a case of arranging a light source emitting light to the recording paper 1 in which a radiation direction of the light is changed, and multiple photodetectors, it is required to arrange the multiple photodetectors in the direction perpendicular to the surface of the recording paper 1. It is preferable to arrange the multiple photodetectors in an approximately perpendicular direction so that the multiple photodetectors do not interfere with each other. Also, a beam splitter may be provided to divide the light, or a polarization filter capable of being driven may be provided to reduce the interference.

(Suppression Method of Speckle Nozzle)

As described above, in view of the reflected light amount, it is preferable to user a semiconductor laser as the light source. However, in a case of using the semiconductor laser as the light source of an optical sensor for detecting a surface state of the recording paper 1, since coherent light emitted from the light source is diffusely reflected at points on a rough surface such as the surface of the recording paper 1 and reflected lights at the points interfere with each other, a speckle pattern occurs. In the speckle pattern, the reflected lights interfere with each other in a reflection direction, and noises are caused in an output of each of the photodetectors. Thus, the S/N is degraded. In the first embodiment, a speckle noise is described as the degraded S/N, a measure for this problem will be described in the following.

Figure 7:
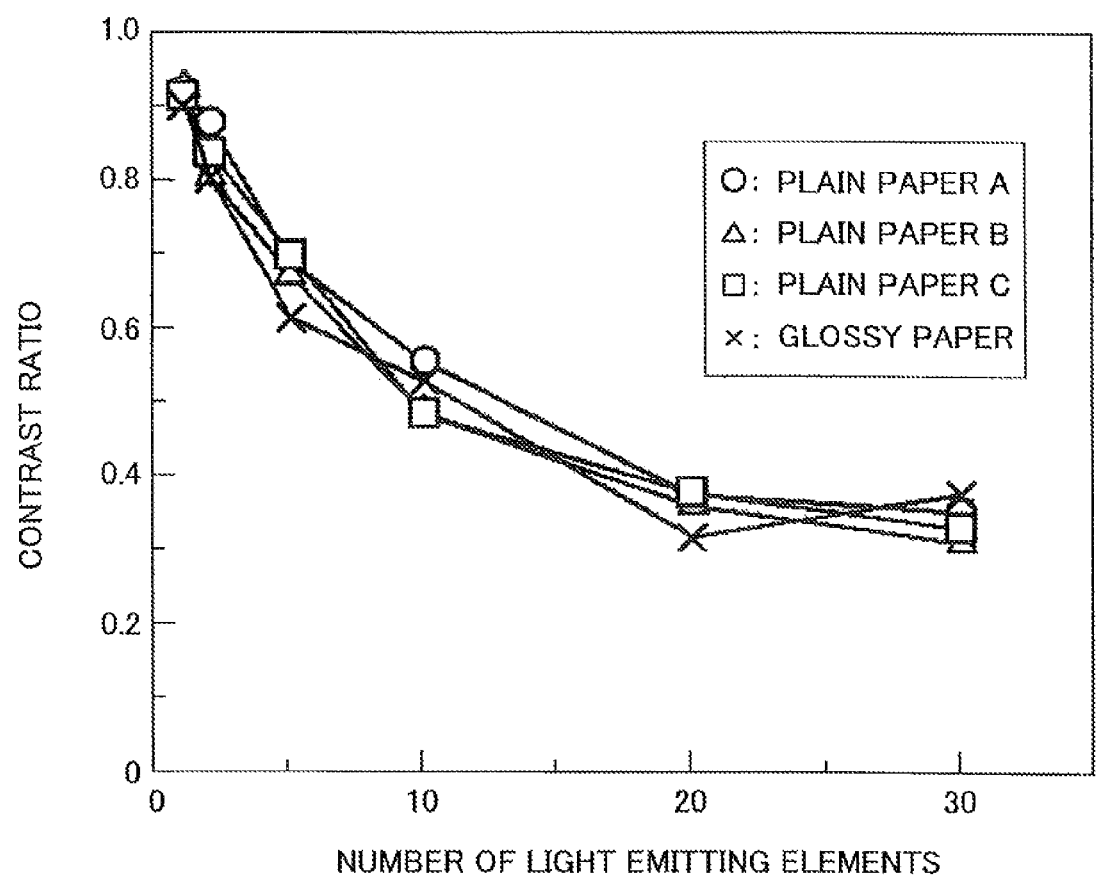
FIG. 7 is a diagram for explaining an influence of a number of light emitting elements, which affects a contrast ratio of a speckle pattern.

Inventors investigated a relationship between a number of the light emitting elements and a contrast ratio of the speckle pattern by using a Vertical-Cavity-Surface-Emitting Laser (VCSEL) as the light source in which multiple light emitting elements are arranged in two dimensions. An investigation result is illustrated in FIG. 7. In the first embodiment, the contrast ratio of the speckle pattern is defined as a value in which a difference between a maximum value and a minimum value in observation intensity is normalized.

Observation of the speckle pattern is performed by using a beam profiler, regarding a Y-axis direction (diffuse direction). The contrast ratio of the speckle pattern is calculated based on an observation result acquired by the beam profiler. As samples for observation targets, three types of plain papers (a plain paper A, a plain paper B, and a plain paper B) having different smoothness degrees and a glossy paper is used. The plain paper A is a paper in which an Oken type smoothness indicated 33 sec. The plain paper B is a paper in which the Oken type smoothness indicated 50 sec. The plain paper C is a paper in which the Oken type smoothness indicates 100 sec.

As illustrated in FIG. 7, when the number of the light emitting elements is increased, the contrast ratio of the speckle pattern tends to decrease. Also, this tendency does not depend on the type of a paper.

Moreover, the inventors performed an experimentation to confirm that an effect of decreasing the contrast ratio of the speckle pattern originated in an increase of the number of the light emitting elements but did not originated in an increase of a total light amount. An experimentation result is illustrated in FIG. 8.

Figure 8:
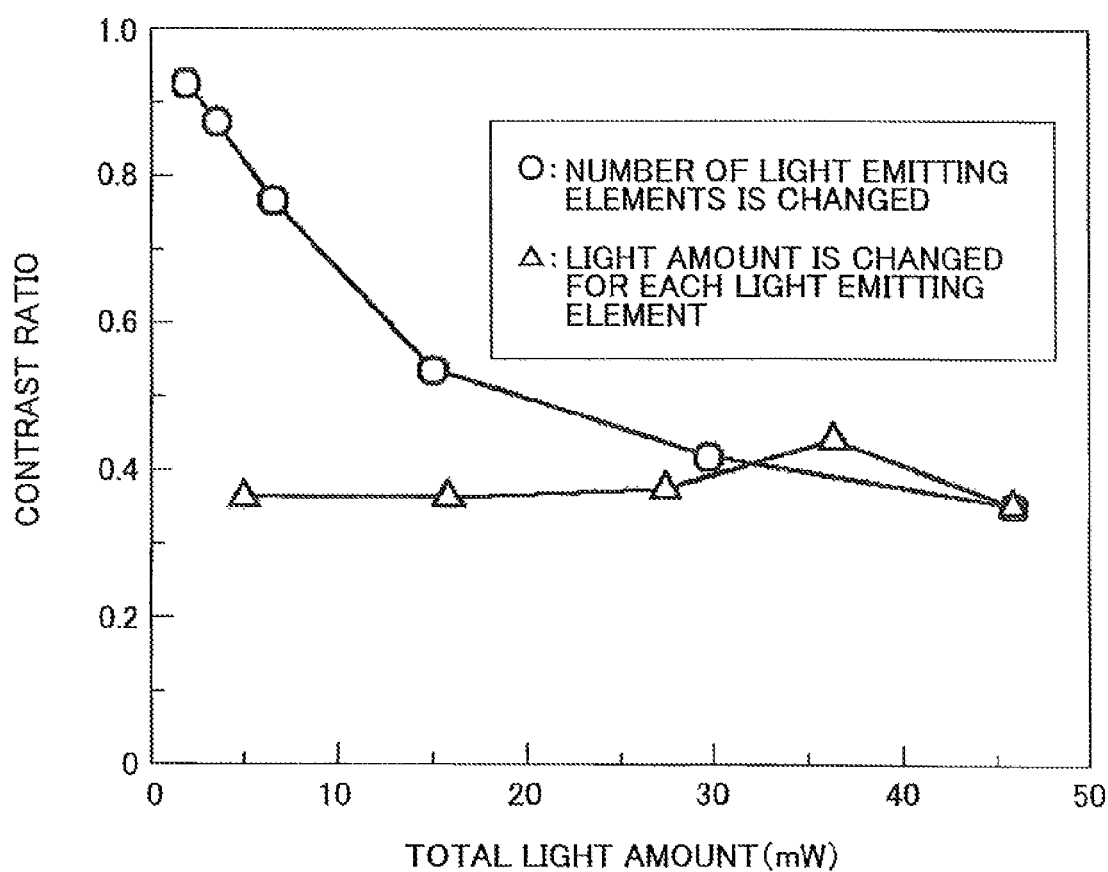
FIG. 8 is a diagram illustrating a relationship between the contrast ratio of the speckle pattern and a total light amount in a case of charging the number of light emitting elements and in a case of changing the light amount for each of the light emitting elements.

FIG. 8 illustrates a change of the contrast ratio with respect to the total light amounts in a case of changing the number of the light emitting elements while each light amount of the light emitting elements is fixed (for example, 1.66 mW) and in a case of charging the light amount for each of the light emitting elements while the number of the light emitting elements is fixed to 30 elements.

In the case of changing the light amount for each of the light emitting elements while the number of the light emitting elements is fixed, the contrast ratio is approximately constant. On the contrary, in the case of changing the number of the light emitting elements while each light amount of the light emitting elements is fixed, if the light amount is less, that is, the number of the light emitting elements is small, the contrast ratio is high. When the number of the light emitting elements is increased, the contrast ratio gradually decreases. Accordingly, it has confirmed that the effect of decreasing the contrast ratio in the speckle pattern depends on the increase of the number of the light emitting elements, but does not depend on the increase of the light amount.

Also, the inventors investigated whether it is possible to suppress the speckle pattern by varying a wavelength of the light emitted from the light source.

In the surface emitting laser (VCSEL), it is possible to control the wavelength of the light emitted by a driving current. When the driving current is changed, heat is generated in the VCSEL, and a refraction index is varied. Then, an effective resonator length is changed.

Figure 9:
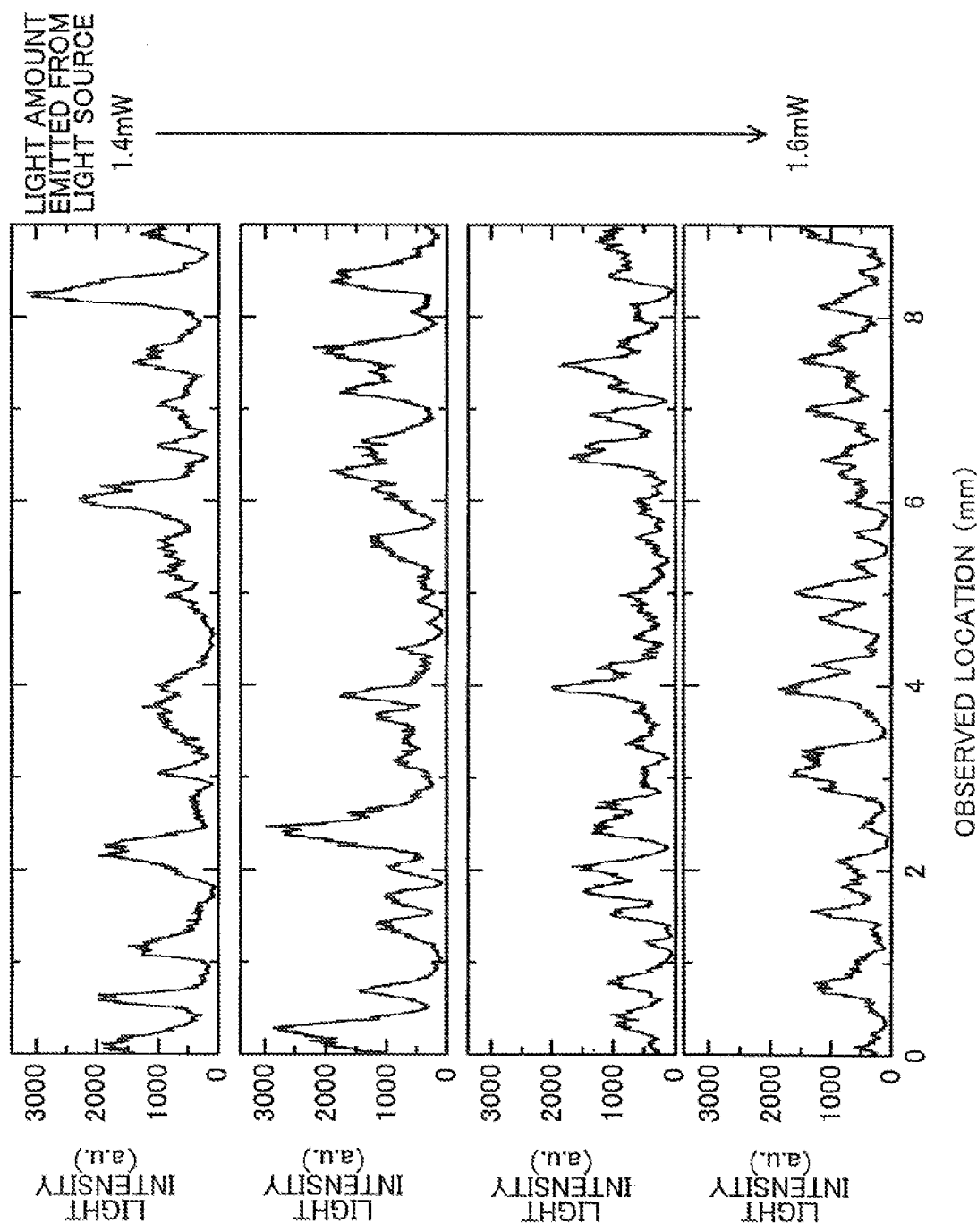
FIG. 9 is a diagram for explaining light intensity distribution of the speckle pattern in a case of changing a driving current of a light source.

FIG. 9 illustrates light intensity distribution acquired by observing the speckle pattern by the beam profiler in a case in which the VCSE is applied as the light source and an emitted light amount is changed from 1.4 mW to 1.6 mW by changing the driving current. As illustrated in FIG. 9, depending on the change of the driving current, the wavelength of the light emitted from the light source is changed. Thus, it is confirmed that the light intensity distribution is changed.

Figure 10:
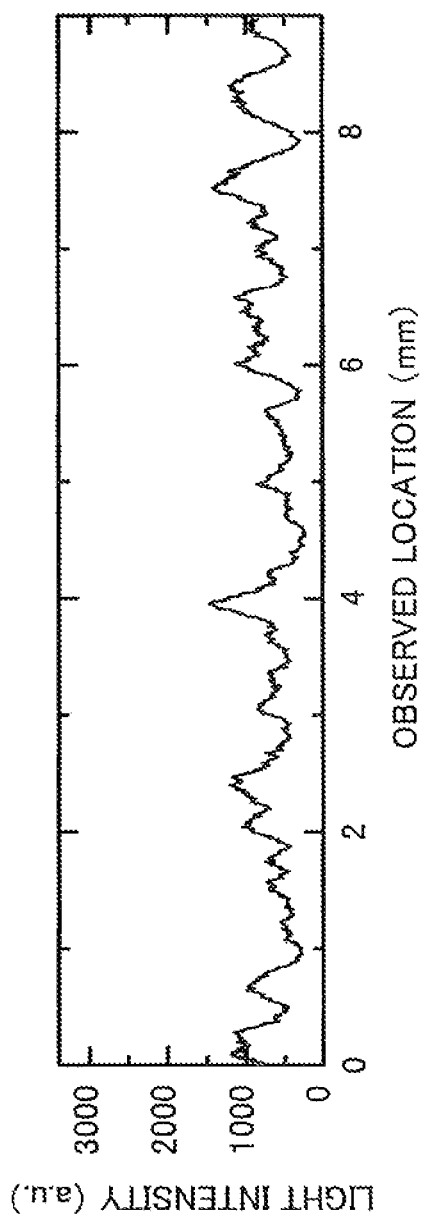
FIG. 10 is a diagram for explaining an effective light intensity distribution of the speckle pattern in a case of changing the driving current of the light source at high speed.

FIG. 10 illustrates an effective light intensity distribution in a case of charging the driving current at high speed. The light intensity distribution is the same as an average value of the light intensity distribution in multiple driving currents illustrated in FIG. 9. Thus, it is confirmed that a change of the light intensity is suppressed. The contrast ratio of the speckle pattern in the case of changing the driving current indicates 0.72, and the contrast ratio of the speckle pattern in the case of fixing the driving current indicates 0.96. Thus, the contrast ratio in the former case is suppressed to be lower that that in the latter case.

Accordingly, in a case of driving the surface emitting laser (VCSEL), for example, flow of the driving current may be controlled so as that a current value forms a triangular waveform in a temporal response. Therefore, it is possible to suppress the contrast ratio to be lower.

(Optical Sensor)

Next, an optical sensor in the first embodiment will be described. In the first embodiment, light illuminating on the recording paper 1 is regarded as linear polarized light and an S-wave, and a reflected light amount is described as a SP intensity in a case in which the photodetector arranged in an approximately perpendicular direction to the surface of the recording paper detects a P-wave. The reflected light amount indicates the light amount of the internal diffuse reflected light. Similarly, the light illuminating the recording paper 1 is regarded as light of the linear polarized light and the P-wave, and the reflected light amount is described as a PS intensity in a case in which the photodetector arranged in the approximately perpendicular direction to the surface of the recording paper 1 detects the S-wave.

Also, the light illuminating the recording paper 1 is regarded as the linear polarized light and the S-wave. The polarizing filter is not provided for the photodetector for detecting light specularly reflected on the surface of the recording paper 1, that is, the photodetector for detecting light reflected at an approximately the same angle as an incident angle of the light illuminating the recording paper 1. Thus, the photodetector detects light including components of both S-wave and P-wave. The reflected light amount detected by the photodetector is described as a SN intensity. An incident angle $\theta$ or the like of the light illuminating the recording paper 1, that is, incident light entering the recording paper 1 indicates an angle with respect to a normal line of the surface of the recording paper 1. An angle for arranging the photodetector may be denoted by an angle $\phi$, $\phi$, or the like with respect to the surface of the recording paper 1 in which a location for the light to enter the recording paper 1 is set as a reference. In the first embodiment, a case, in which the light illuminating the recording paper 1 is the S-wave, is described. However, the first embodiment is not limited to this case but the light illuminating the recording paper 1 may be the P-wave.

Figure 11:
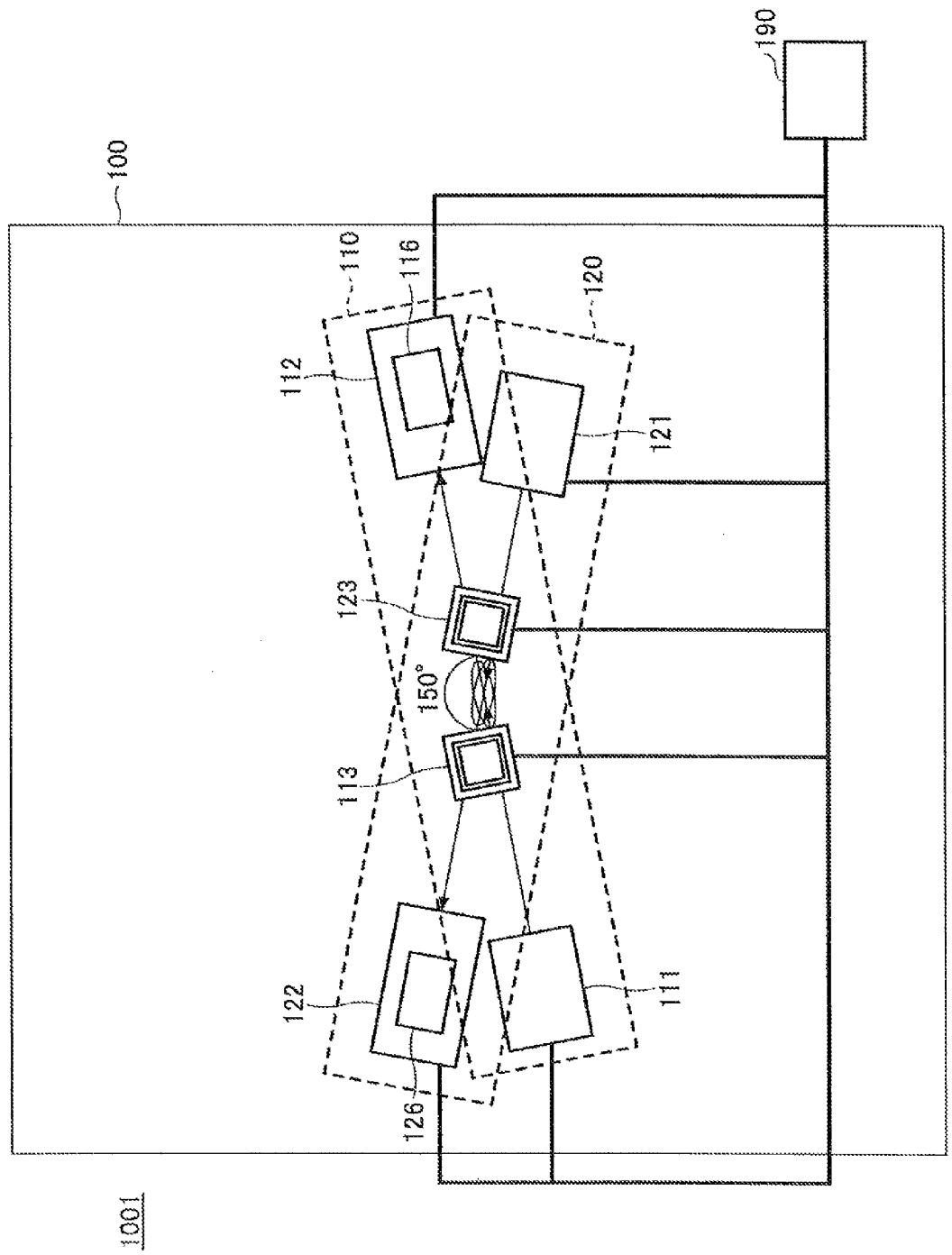
FIG. 11 is a top view of an optical sensor in a first embodiment.
Figure 12:
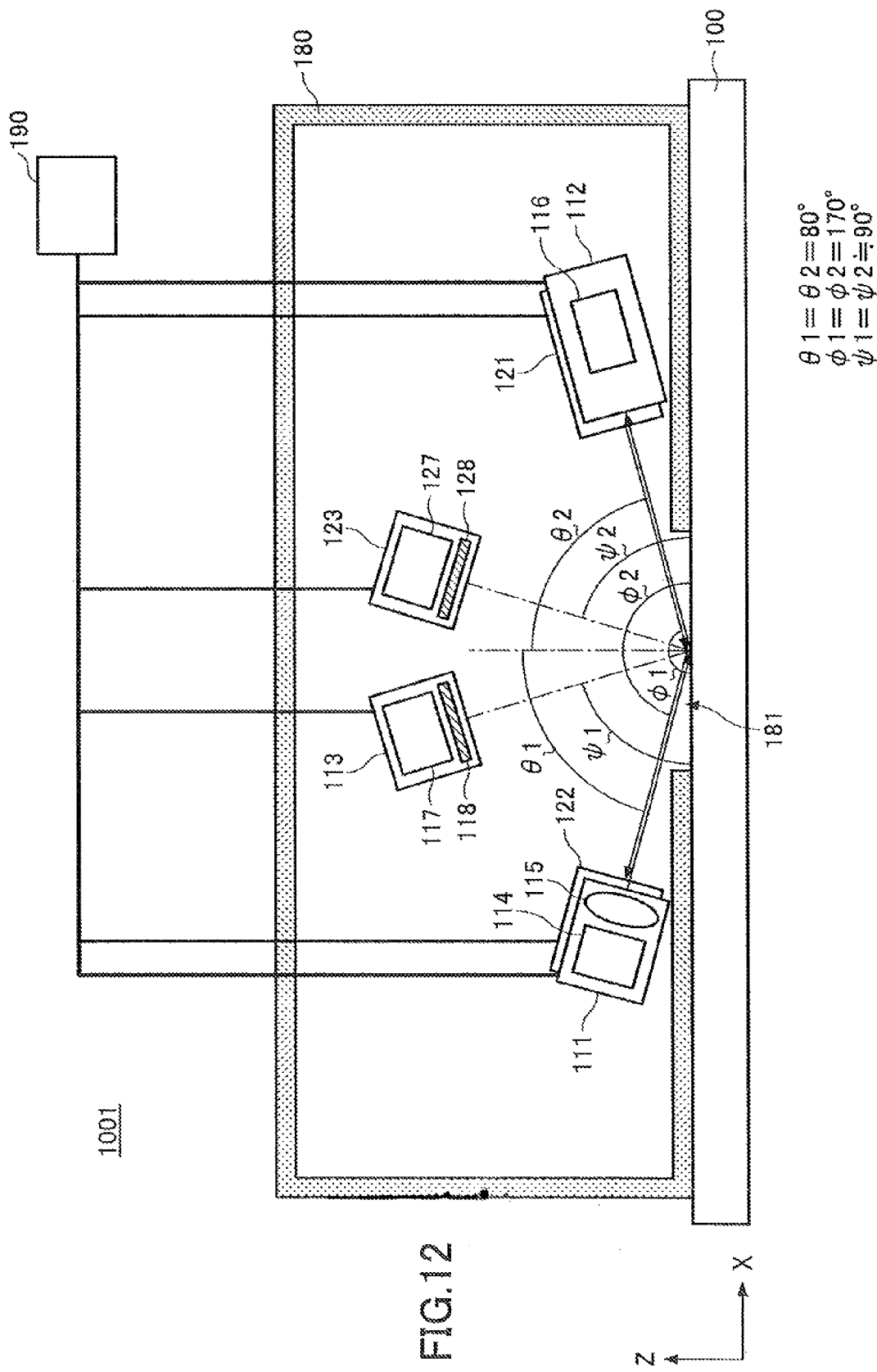
FIG. 12 is a lateral view of the optical sensor in the first embodiment.

Next, an optical sensor 1001 in the first embodiment will be described with reference to FIG. 11 and FIG. 12. The optical sensor 1001 includes two measurement systems: a first measurement system 110 and a second measurement system 120. The first measurement system 110 includes a first light emission system 111, a first specular reflected light detection system 112, and a first diffuse reflected light detection system 113. Also, the second measurement system 120 includes a second light emission system 121, a second specular reflected light detection system 122, and a second diffuse reflected light detection system 123.

The first measurement system 110 and the second measurement system 120 are covered with a dark box 180. An opening part 181 is provided to the dark box 180 to illuminate light onto the surface of a recording paper 100. The first measurement system 110 and the second measurement system 120 are enclosed by the dark box 180 and the recording paper 100. External light and the like do not entered from the outside. Thus, it is possible to perform a precise measurement. Also, the first light emission system 111, the first specular reflected light detection system 112, the first diffuse reflected light detection system 113, the second light emission system 121, the second specular reflected light detection system 122, and the second diffuse reflected light detection system 123 are connected to the control part 190.

Also, in the first embodiment, the first measurement system 110 and the second measurement system 120 are arranged so that an angle, which is formed by a light path or light emitted from the first light emission system 111 and another light path of light emitted from the second light emission system 121, becomes 150° on a XY plane. That is, an angle, which is formed by a component parallel to the recording paper 100 in the light emitted from the first light emission system 111 and another component parallel to the recording paper 10 in the light emitted from the second light emission system 121, becomes 150° on the XY plane. It is preferable for this angel to be more than 90° and less than 180°. In a case in which the angle is more than 90° and less than 180°, the light emitted from the second light emission system 121 includes a component emitted from an opposite direction as illustrated in FIG. 6 with respect to the light emitted from the first light emission system 111. Therefore, it is possible to identify the recording medium at higher accuracy. Also, in the first embodiment, "emitting light on the XY plane" indicates a state of projection on the XY plane.

The first light emission system 111 includes a light source 114, a collimating lane 115, and the like. A configuration of the second light emission system 121 is the same as the configuration of the first light emission system 111. The first light emission system 111 is arranged at a location where the light enters at an angle θ1 with respect to the normal line of the recording paper 100. The second light emission system 121 is arranged at a location where the light enters at an angle θ2 with respect to the normal line of the recording paper 100. In the first embodiment, the angle θ1 and the angle θ2 are the same and approximately 80°. The angle θ1 is regarded as an angle formed by a direction of the light emitted from the first light emission system 111 to the recording paper 100 and the normal line of the surface of the recording paper 100. The angle θ2 is regarded as an angle formed by a direction of the light emitted from the second light emission system 121 to the recording paper 100 and the normal line of the surface of the recording paper 100.

The first specular reflected light detection system 112 is used to detect the surface specular reflected light in the light emitted from the first light emission system 111 to the recording paper 100, and includes a photodetector 116 formed by a light receiving element such as a photo diode or the like. The second specular reflected light detection system 122 is used to detect the surface specular reflected light in the light emitted from the second light emission system 121 to the recording paper 100, and includes a photodetector 126 formed by a light receiving element such as a photo diode or the like.

The first diffuse reflected light detection system 113 is used to detect the surface diffuse reflected light an the internal diffuse reflected light in the light emitted from the first light emission system 111 to the recording paper 100, and includes a photodetector 117 formed by a light receiving element such as a photo diode or the like. A polarizing filter 118 is provided in front of the photodetector 117. The second diffuse reflected light detection system 123 is used to detect the surface diffuse reflected light and the internal diffuse reflected light in the light emitted from the second light emission system 121 to the recording paper 100, and includes a photodetector 127 formed by a light receiving element such as a photo diode or the like. A polarizing filter 128 is provided in front of the photodetector 127.

The dark box 180 is formed by material such as aluminum. For a surface, that is, an exterior surface and an interior surface of the dark box 180, a black alumite process is performed to prevent influence due to disturbing light and stray light. The recording paper 100 is provided to be parallel to the XY plane. The optical sensor 1001 in the first embodiment is provided at a positive side of a Z axis with respect to the recording paper 100.

In the first light emission system 111, the light source 114 includes multiple light emitting elements. Each of the light emitting elements is regarded as a Vertical Cavity Surface Emitting Laser (VCSEL) formed on the same substrate. That is, the light source 114 includes a surface emitting laser array (VCSEL array). Also, a similar configuration is formed in the second light emission system 121.

Figure 13:
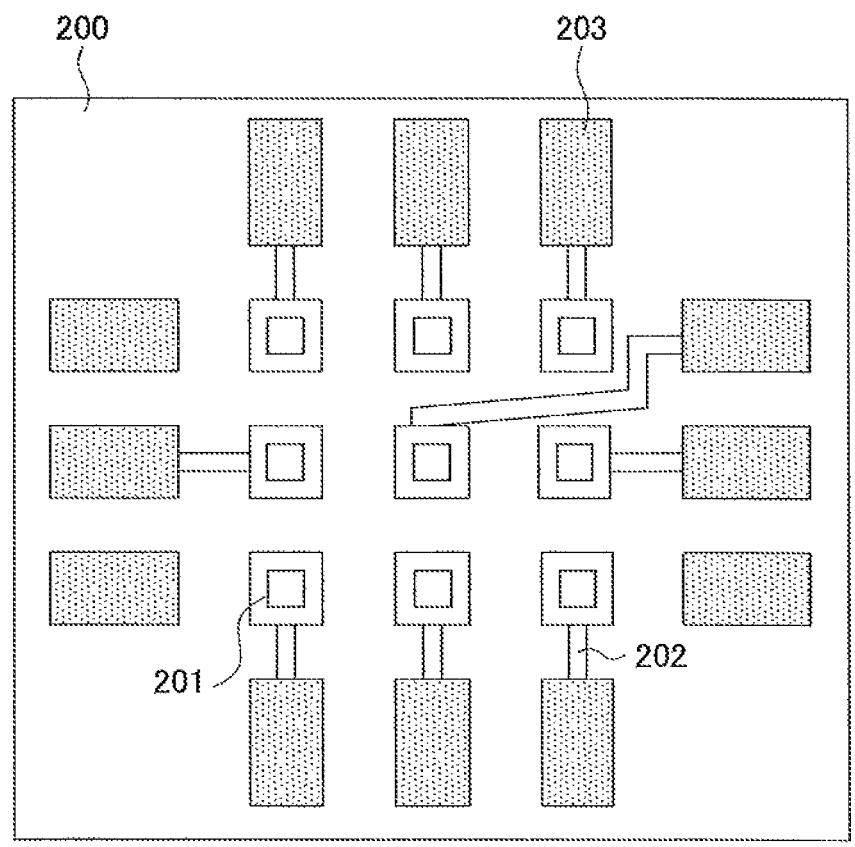
FIG. 13 is a diagram illustrating a configuration of a surface emitting laser array.

As illustrated in FIG. 13, a surface emitting laser array 200 includes light emitting elements 201 each formed by the VCSEL, wirings 202 connected to respective light emitting elements 201, and electrode pads 203 connected to respective wirings 202. In FIG. 13, as an example, in the surface emitting laser array 200, nine (ch1 to ch9) light emitting elements 201 are arrayed in two dimensions.

Also, in the first embodiment, a CPU (Central Processing Unit) regarded as a controller supplies the driving current to the surface emitting laser array 200 so that the current value forms the triangular waveform in a temporal response. By this configuration, the speckle pattern is suppressed, and it is possible to detect an accurate reflected light amount of the recording paper 100. Thus, it is possible to improve accuracy of identifying the recording paper 100. That is, by temporally changing the driving current to be the triangular waveform, it is possible to perform a time varying of the wavelength of the light emitted from the light source 114. Therefore, it is possible to suppress the speckle pattern.

Moreover, in a case of using the surface emitting laser, it is possible to easily adjust the light illuminating the recording paper 100 to be parallel light. Thus, it is possible to reduce the size of the optical sensor 1001 and realize lower expense of the optical sensor 1001.

The first light emission system 111 and the second light emission system 121 are formed so that light of a S-polarization is emitted to the recording paper 100. In a case of using a non-polarized light source of a LED (Light Emitting Diode), white light, or the like as the light source 114 and the like, a polarizing filter is arranged for the light omitted from the light source 114 and the like to be light of the S-polarization. The light emitted from the light source 114 and the like is needed to be the light of the S-polarization, by passing through the polarizing filter. Also, light is emitted from the first light emission system 111 at the angle θ1, and the light is emitted from the second light emission system 121 at the angle θ2. The angle θ1 and the angle θ2 are 80°. However, greater angles related to the angle θ1 and the angle θ2 of respective incident light are preferable to specify the type or the like of the recording paper 100.

In the first light emission system 111, the collimating lens 115 is arranged on the light path of a light flux emitted from the light source 114, and collimates the light flux to be approximately parallel light. The parallel light collimated by the collimating lens 115 illuminates the recording paper 100 at the opening part 181 provided to the dark box 180. A similar configuration is formed in the second light emission system 121. In the first embodiment, an area illuminated by the parallel light on the surface of the recording paper 100 may be described as an irradiation area, and a central position of the irradiation area may be described as an "illumination center". Light passing the collimate lens 115 may be described as an "irradiated light". In the first embodiment, the illumination center of the light emitted from the first light emission system 111 is located at approximately the same position as the illumination center of the light emitted from the second light emission system 121. Also, dimensions of both irradiation areas are approximately the same.

When a light enters an interface of a medium, a surface including an irradiated light and the normal line of the interface at an incident point is called an "incident surface". In a case in which the irradiation light is formed by multiple light beams such as the surface emitting laser array 200 (VCSEL array) including the nine light emitting elements 201 illustrated in FIG. 13, the incident surface may exist for each light beam. However, in the first embodiment, the incident surface of the light emitted from the light emitting element 201 arranged in a center of the surface emitting laser array 208 (VCSEL array) is represented as the incident surface to the recording paper 100.

The first specular reflected light detection system 112 is arranged at a position where specular reflected light is received in reflection of the light emitted from the first light emission system 111 to the recording paper 100. That is, the first specular reflected light detection system 112 is arranged in a direction in which an angle $\phi 1$ is 170° with respect to the surface of the recording paper 100, and on a surface which includes the first light emission system 111 and the illumination center. The second specular reflected light detection system 122 is arranged at a position where the specular reflected light is received in the reflection of the light emitted from the second light emission system 121 to the recording paper 100. That is, the second specular reflected light detection system 122 is arranged in a direction in which an angle $\phi 2$ is 170° with respect to the surface of the recording paper 100, and on a surface which includes the second light emission system 121 and the illumination center.

For each of the photodetector 116 in the first specular reflected light detection system 112 and the photodetector 126 in the second specular reflected light detection system 122, a photodiode including the same light receiving diameter is used. Also, the photodetector 116 and photodetector 126 are arranged at positions of the same distance from the illuminator center. Condensing lens may be provided between the illumination center and the photodetector 116, and between the illumination center and photodetector 126. In this case, a distance between the illumination center and each of the condensing lens may be uniform.

The first diffuse reflected light detection system 113 is used to detect the diffuse reflected light in the light emitted from the first light emission system 111, and is arranged in a direction in which an angle $\phi 1$ indicates 90° with respect to the surface of the recording paper 100 at the illumination center. The second diffuse reflected light detection system 123 is used to detect the diffuse reflected light in the light emitted from the second light emission system 121, and is arranged in a direction in which an angle $\psi 2$ indicates 90° with respect to the surface of the recording paper 100 at the illumination center. The angles $\psi 1$ and $\psi 2$ may be 90° preferably. Since each of the first diffuse reflected light detection system 113 and the second diffuse reflected light detection system 123 includes a predetermined size, location thereof may be cause of interference with each other. Accordingly, it is preferable in that the first diffuse reflected light detection system 113 and the second diffuse reflected light detection system 123 are arranged at angles not to mutually interfere, the angle close to 90° as possible, that is, approximately 90°.

The polarizing filter 118 provided in the first diffuse reflected light detection system 113 passes light of the P-polarization and shields light of the S-polarization. The polarizing filter 128 provided in the second diffuse reflected light detection system 123 also passes light of the P-polarization and shields light of the S-polarization. Instead of using the polarizing filter 118 and polarizing filter 128, a polarizing beam splitter having an equivalent function may be used. The first diffuse reflected light detection system 113 and the second diffuse reflected light detection system 123 are arranged at positions of the same distance from the illuminator center so that angles $\psi 1$ and $\psi 2$ are approximately the same angles.

In the first embodiment, in the first measurement system 110, a center of the light source 114 of the first light emission system 111, the illumination center, a center of the photodetector 116 of the first specular reflected light detection system 112, a center of the photodetector 117 of the first diffuse reflected light detection system 113, and a center of the polarizing filter 118 are located on the same plane. Similarly, in the second measurement system 120, a center of the light source of the second light emission system 121, the illumination center, a center of the photodetector 126 of the second specular reflected light detection system 122, a center of the photodetector 127 of the second diffuse reflected light detection system 123 are located on the same plane.

In addition, the photodetector 116 of the first specular reflected light detection system 112, the photodetector 117 of the first diffuse reflected light detection system 113, the photodetector 126 of the second specular reflected light detection system 122, and the photodetector 127 of the second diffuse reflected light detection system 123 output electronic signals (photoelectric conversion signals), respectively. In the first embodiment, in a case of omitting the light from the first light emission system 111 onto the recording paper 100, a signal level of an output signal of the photodetector 116 of the first specular reflected light detection system 112 is denoted by "S11", and a signal level of an output signal of the photodetector 117 of the first diffuse reflected light detection system 113 is denoted by "S12". Similarly, in a case of emitting the light from the second light emission system 121, a signal level of an output signal of the photodetector 126 of the second specular reflected light detection system 122 is denoted by "S21", and a signal level of an output signal of the photodetector 127 of the second diffuse reflected light detection system 123 is denoted by "S22".

Figure 14:
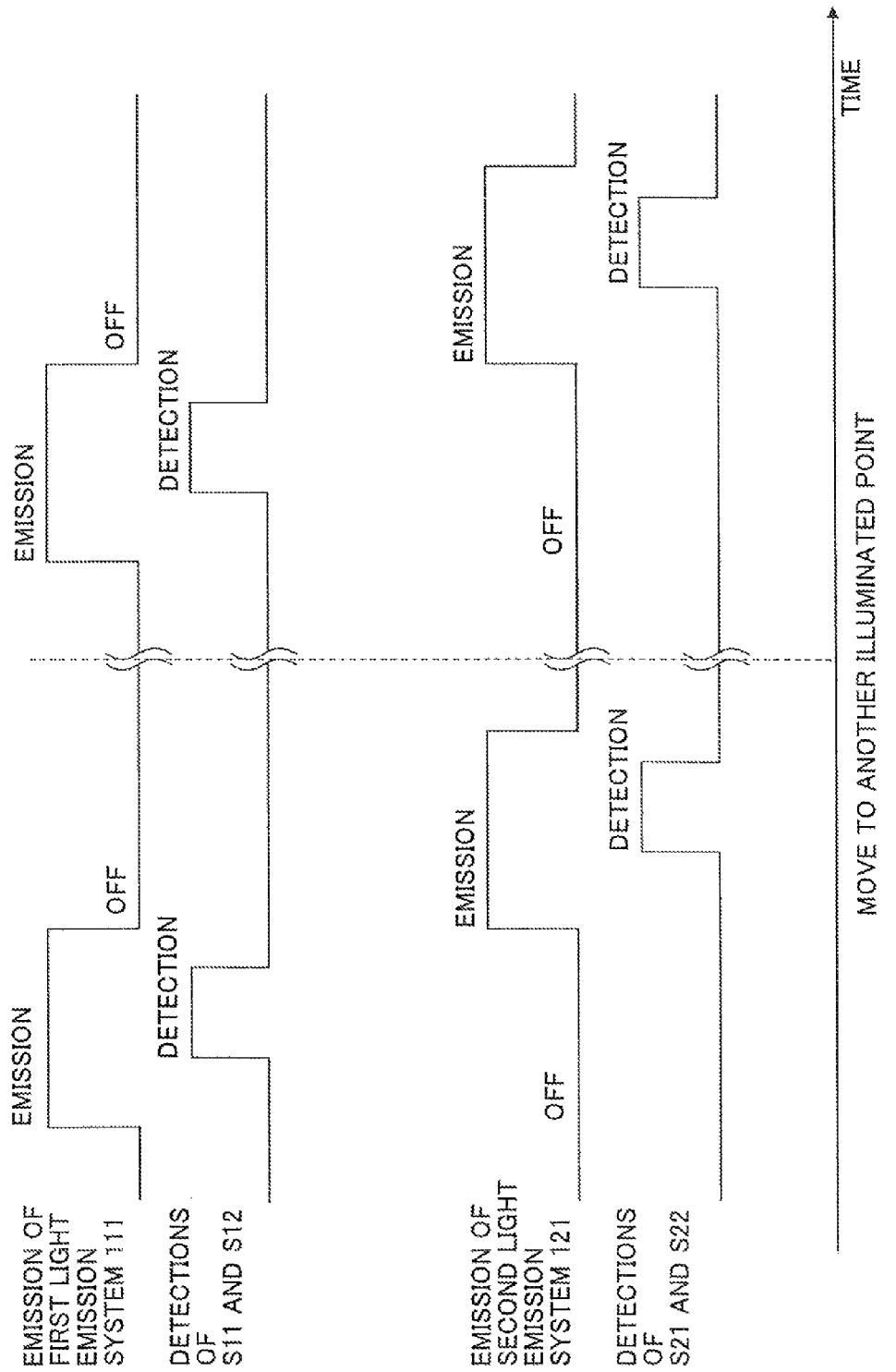
FIG. 14 is a diagram for explaining a method for controlling the optical sensor in the first embodiment.

In the first embodiment, a measurement by the first measurement system 110 and a measurement by the second measurement system 120 are separately performed. The control part 190 controls light emissions of the light source 114 and the like so that timing of the light emission by the first light emission system 111 is not overlapped with timing of the light emission by the second light emission system 121. The light amount detected by the photodetector 117 of the first diffuse reflected light detection system 113 may be regarded as the light amount of diffused light alone in the light emitted from the first light emission system 111. The light amount detected by the photodetector 127 of the second diffuse reflected light detection system 123 may be regarded as the light amount of diffused light alone in the light emitted from the second light emission system 121. In detail, as illustrated in FIG. 14, the timing of the light emission by the first light emission system 111 may be hardly overlapped with the timing of the light emission by the second light emission system 121. Moreover, the signal level S11 and the signal level S12 are detected while the first light emission system 111 emits the light. The signal level S21 and the signal level S22 are detected while the second light emission system 121 emits the light.

Based on the signal levels S11, S12, S21, and S22, the name, the smoothness, the thickness, and the density related to the type of the recording paper 100 are determined. In detail, the signal levels S11, S12, S21, and S22 are measured beforehand for each of various types of the recording papers 100 used for an image forming apparatus such as a color printer or the like. Based on the measurement result, a "recording paper determination table" is created in which output ranges for the signal levels S11, S12, S21, and S22 correspond to the types of the recording papers 100. The recording paper determination table is stored in the control part 190 or the image forming apparatus before the image forming apparatus is shipped.

In a case of printing the recording paper 100 by the image forming apparatus, the signal levels S11, S12, S21, and S22 are measured by the optical sensor 1001 in the first embodiment. Based on the signal levels S11, S12, S21, and S22, the name, the smoothness, the thickness, and the density related to the type of the recording paper 100 are determined by referring to the recording paper determination table. This determination is performed by an adjustment device, or the control part 190 in the image forming apparatus.

Figure 15:
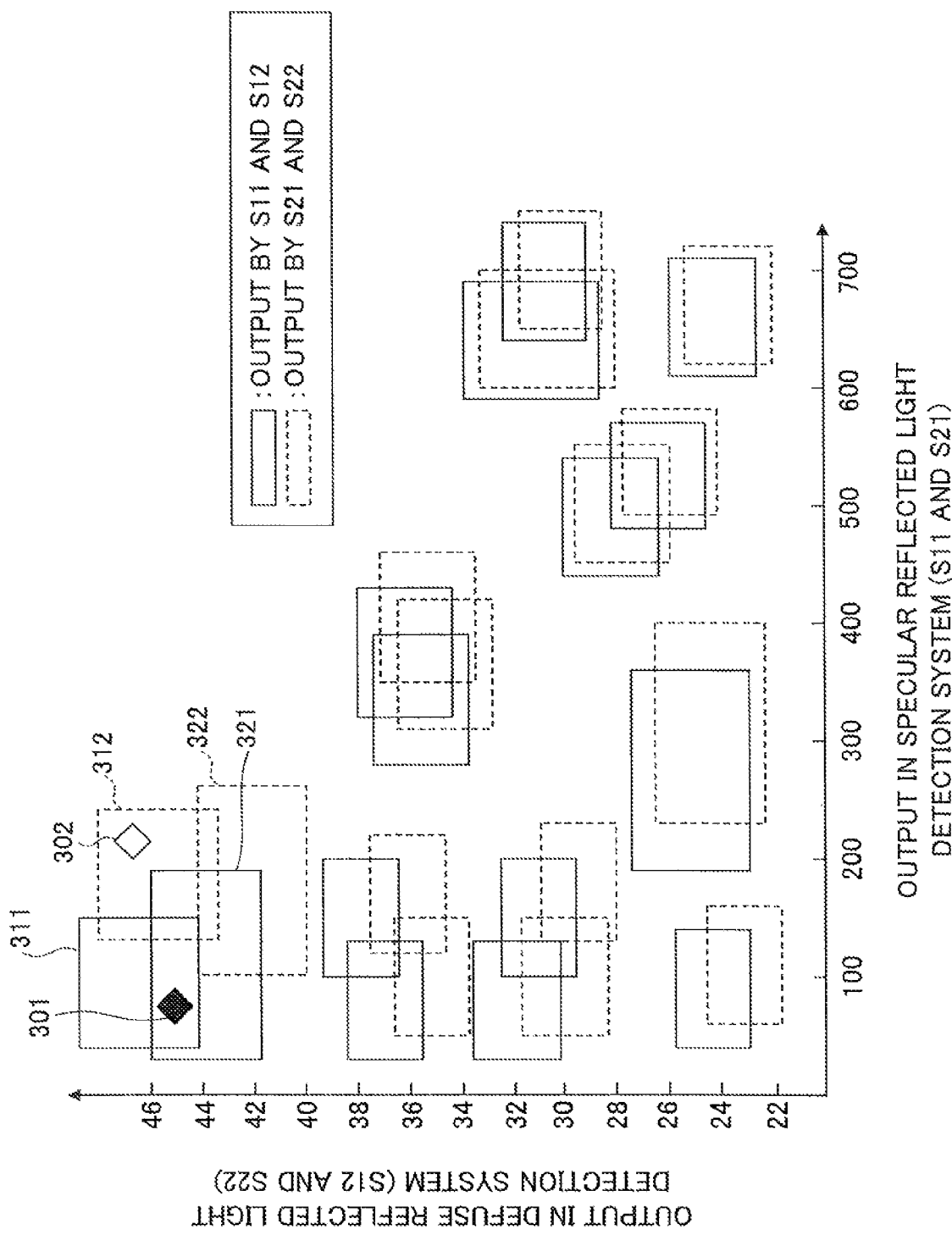
FIG. 15 is a diagram illustrating a relationship a type of the recording medium and outputs of the specular reflected light detection system and the diffuse reflected light detection system (part 1).

In detail, as illustrated in FIG. 15, the recording paper determination table indicated ranges of the signal levels S11 and S12 and ranges of the signal levels S21 and S22, which correspond to each of the types of the recording papers 100. Based on the recording paper determination table, the type, the name, and the like of the recording paper 100 are determined based on the ranges of the signal levels S11 and S12 and ranges of the signal levels S21 and S22.

In a case illustrated in FIG. 15, if a location based on the signal levels S11 and S12 detected by the first measurement system 110 for the recording paper 100 indicates a point 301, the point 301 is included in both a range 311 (regarded as an output range by the signal levels S11 and S12 of a name A) and a range 321 (regarded as an output range by the signal levels S11 and S12 of a name B). The recording paper 100 may be the name A or the name B. However, it is not possible to specify which name A or B is that of the recording paper 100. If a location based on the signal levels S21 and S22 detected by the second measurement system 120 for the recording paper 100 indicates a point 302, the point 302 exists in a range 312 (regarded as an output range by the signal levels S21 and S22 of the name A) but does not exist in a range 322 (regarded as an output range by the signal levels S21 and S22 of the name B). Accordingly, it is possible to determine the recording paper 100 as the name A.

Figure 16:
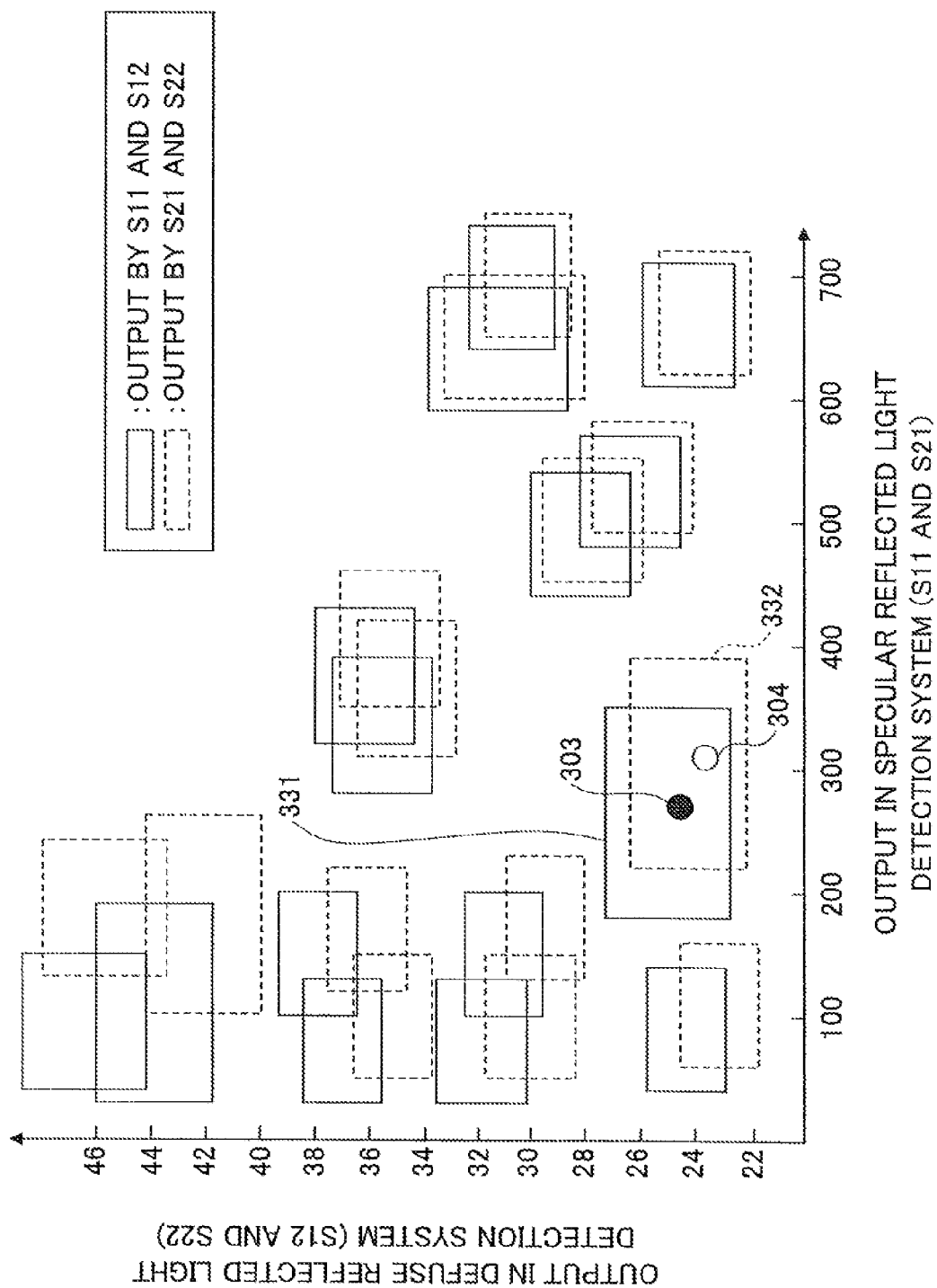
FIG. 16 is a diagram illustrating the relationship a type of the recording medium and the outputs of the specular reflected light detection system and the diffuse reflected light detection system (part 2).

Also, in a case illustrated in FIG. 16, if a location based on the signal levels S11 and S12 detected by the first measurement system 110 for the recording paper 100 indicates a point 303, the point 303 exists in a range 331 (regarded as an output range by the signal levels S11 and S12 of a name C). Accordingly, the recording paper 100 may be determined as the name C. Moreover, a location based on the signal levels S21 and S22 detected by the second measurement system 120 indicates a point 304, the point 304 exists in a range 332 (regarded as an output range by the signal levels S21 and S22 of the name C). Accordingly, it is possible to determine the recording paper 100 as the name C.

In addition to the above described determination, it is possible to determine a direction of the grain of the recording paper 100 based on a value calculated by deducting the signal level S11 from the signal level S21 (S21−S11) and another value calculated by deducting the signal level S12 from the signal level S22 (S22−S12). In the case illustrated in FIG. 16, based on the point 303 and the point 304, the value of S21−S11 indicates a positive value and the value of S22−S12 indicates a negative value. Accordingly, it may be considered that the grain of the recording paper 100 is near a direction along a light path in the second measurement system 120. That is, it may be considered that the grain of the recording paper 100 indicates a direction near a component parallel to the recording paper 100 on the light path in the second measurement system 120. As described above, in a case of emitting the light along the grain of the recording paper 100, the light amount of the specular reflected light is increased. In a case of emitting the light perpendicular to the grain, the light amount of the diffuse reflected light is increased. Based on this observation, since the value of S21−S11 indicates a positive value and the value of S22−S12 indicates a negative value, it may be determined that the grain of the recording paper 100 is near the direction along the light path in the second measurement system 120.

In the first embodiment, a case of emitting the light focused on one point on the recording paper 100 is described. The light may be emitted toward multiple locations on the recording paper 100, and the reflected light from each of the multiple locations is detected. An average of the light amounts respective to the multiple locations is calculated, and the type and the like of the recording paper 100 may be determined.

Since the optical sensor 1001 in the first embodiment includes two measurement systems, compared to a single measurement system, it is possible to improve the accuracy of determining the recording paper 100.

Also, in a method for identifying the recording paper 100 in the first embodiment, a paper type identifying method, which applies an internal rotatory light amount including information related to inside the recording paper 100 which has not been conventionally separated and detected, is provided in addition to an identifying method in a related art. By detecting a polarization direction at a proper location in view of information of the recording paper 100 included in a polarization component of diffused light, it is possible to acquire information of the thickness, the density, and the like, in addition to a conventional glossiness (smoothness) degree of the surface of the recording paper 100. Therefore, it is possible to segment a name identification level of the recording paper 100.

Also, since the light source includes the multiple light emitting elements, it is possible to increase the light amount of a P-polarization component included in the internal diffuse reflected light. Furthermore, compared to a configuration in which the light source includes one light emitting element, it is possible to reduce the contrast ratio of the speckle pattern, and to improve the accuracy of identifying the recording paper 100.

Moreover, since the surface emitting laser is driven by the driving current in which a current value changes temporally, it is possible to further reduce the contrast ratio of the speckle pattern.

Second Embodiment

Figure 17:
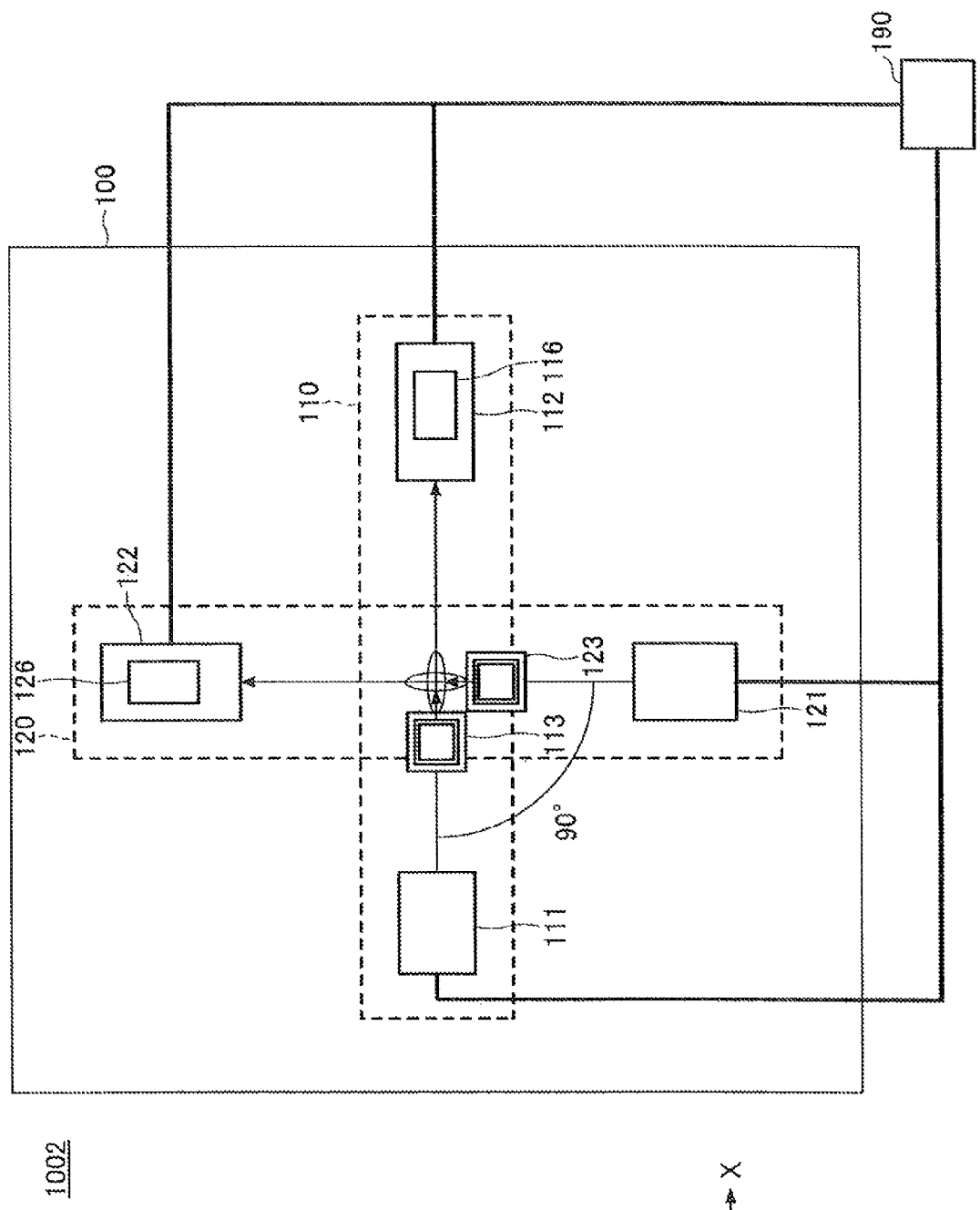
FIG. 17 is a top view of the optical sensor in a second embodiment.
Figure 18:
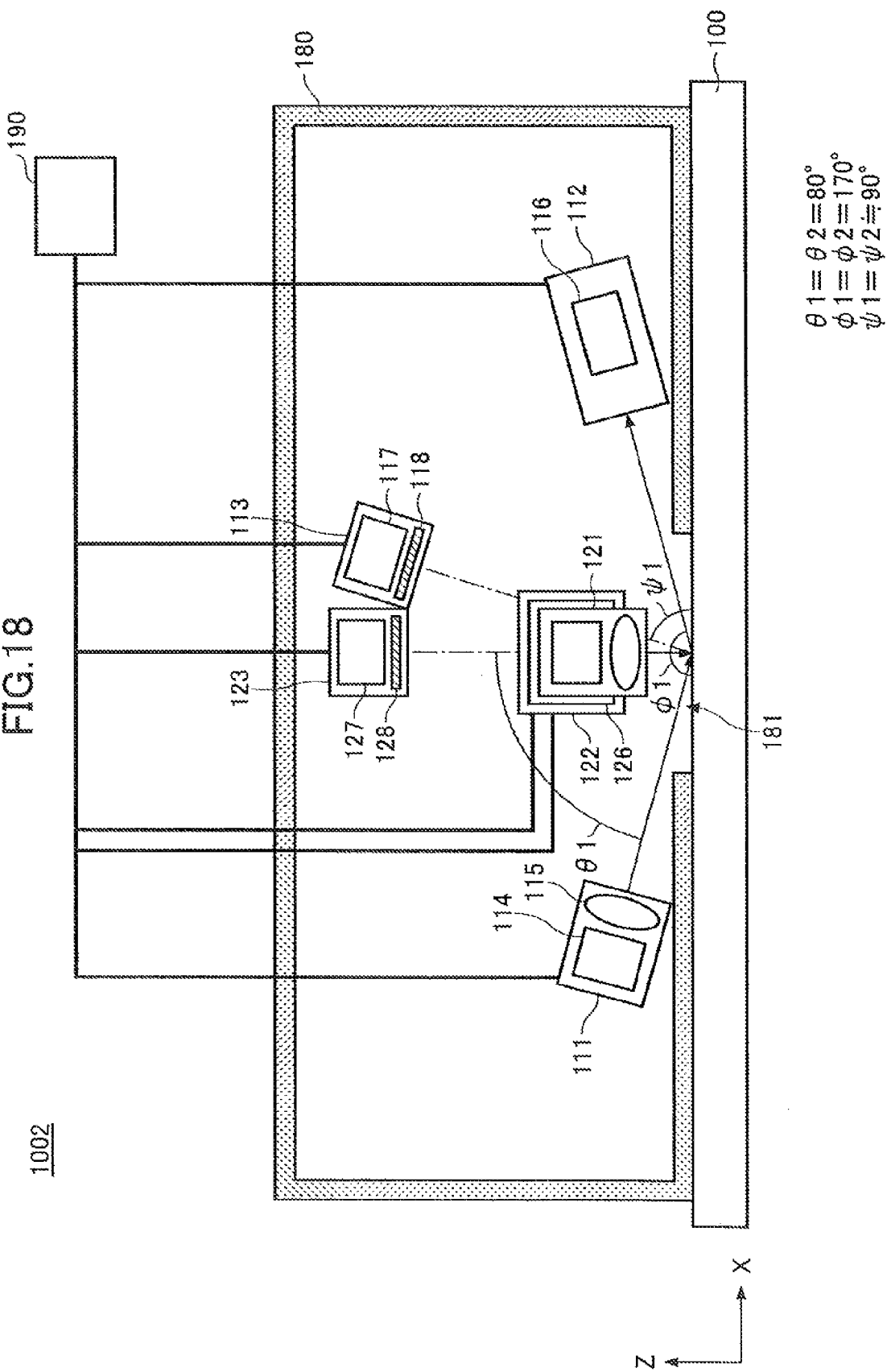
FIG. 18 is a lateral view of the optical sensor in the second embodiment.

Next, a second embodiment will be described with reference to FIG. 17 and FIG. 18. An optical sensor 1002 in the second embodiment includes two measurement systems similar to the optical sensor 1001 in the first embodiment. That is, the optical sensor 1002 includes the first measurement system 110 and the second measurement system 120. However, different from the first embodiment, the first measurement system 110 and the second measurement system 120 are arranged so that an angle between the light path of the light emitted from the first light emission system 111 and the light path of the light emitted from the second light emission system 121 is formed to be 90° on the XY plane. In other words, the systems 110 and 120 are arranged so that an angle between a component of the light emitted from the first light emission system 111 in which the component is parallel to the recording paper 100 and a component of the light emitted from the second light emission system 121 in which the component is parallel to the recording paper 100 is formed to be 90°.

In a direction perpendicular to the orientation direction of the recording paper 100, a difference between two specular reflected lights detected in respective measurement systems 110 and 120 becomes maximum. Also, a difference between two internal diffuse reflected lights detected in respective measurement systems 110 and 120 becomes maximum. Accordingly, the first measurement system 110 and the second measurement system 120 are arranged so that an angle between the light path of the light emitted from the first light emission system 111 and the light path of the light emitted from the second light emission system 121 is formed to be 90° on the XY plane. Accordingly, it is possible to determine the recording paper 100 at higher accuracy.

In general, a rectangular shape of the recording paper 100 is mostly used. In the first embodiment, the light path of the light emitted from the first light emission system 111 exists on a plane parallel to one side of the recording paper 100 and the light path of the light emitted from the second light emission system 121 exists on a plane parallel to another side of the recording paper 100. That is, on the XY plane, the light path of the light emitted from the first light emission system 111 is parallel to the one side of the recording paper 100. Also, the light path of the light emitted from the second light emission system 121 is parallel to another side of the recording paper 100. In other words, the one side of the recording paper 100 is approximately parallel to a component in the light emitted from the first light emission system 111 in which the component is parallel to the recording paper 100. Also, another side of the recording paper 100 is approximately parallel to a component in the light emitted from the second light emission system 121 in which the component is parallel to the recording paper 100. In a case of a square shape of the recording paper 100, the same manner is applied.

In general, fabric taken from pulp is streamed in one direction in a production apparatus and the recording paper 100 is produced. By streaming in one direction in the production apparatus, the fabric forming the recording paper 100 is aligned toward a streaming direction. Accordingly, a streaming direction of the recording paper 100 becomes the orientation direction of the fabric. As described above, the irregular surface is formed by oriented fabric. In general, a paper is out in a parallel direction and in a perpendicular direction to the stream of the fabric, thereby multiple recording papers 100 are produced in a predetermined size in the production stage.

Accordingly, the first light emission system 111 and the second light emission system 121 are arranged, so that the path of the light emitted from the first light emission system 111 exists a surface parallel to one side of the recording paper 100, and the light path of the light emitted from the second light emission system 121 exists a surface parallel to another side of the recording paper 100. The difference between the specular reflected light detected in the first light emission system 111 and the specular reflected light detected in the second light emission system 121 becomes maximum. Also, the difference of the internal diffuse reflected light becomes maximum.

Configurations other than the above described configuration in the second embodiment are the same as the configurations in the first embodiment, and the explanation thereof will be omitted.

Third Embodiment

Figure 19:
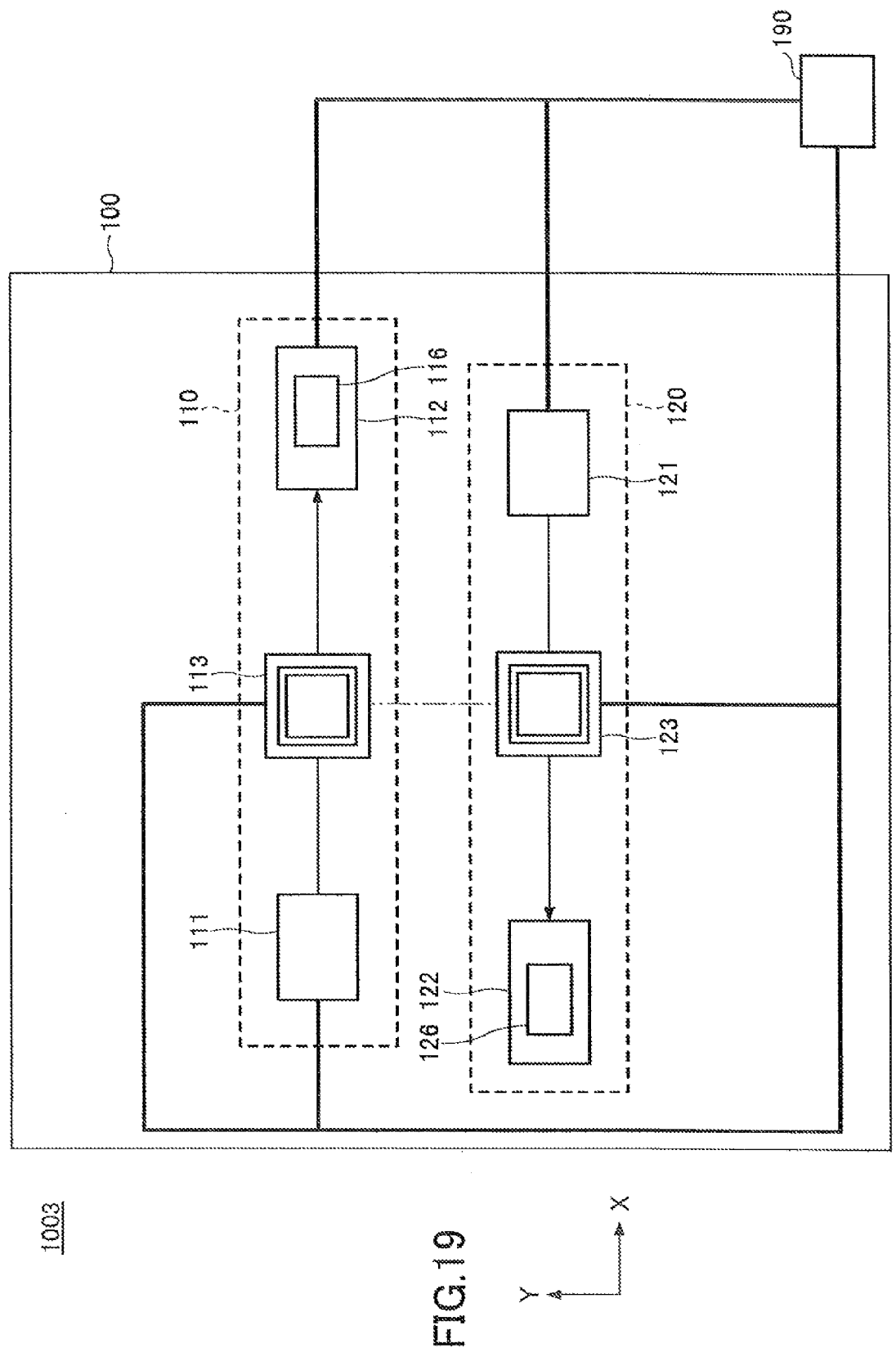
FIG. 19 is a top view of the optical sensor in a third embodiment.

Next, a third embodiment will be described. The third embodiment will be described with reference to FIG. 19. An optical sensor 1003 in the third embodiment includes two measurement systems similar to the first embodiment. That is, the optical sensor 1003 includes the first measurement system 110 and the second measurement system 120. However, different from the first embodiment, the first measurement system 110 and the second measurement system 120 are arranged so that the angle between the light path of the light emitted from the first light emission system 111 and the light path of the light emitted from the second light emission system 121 is formed to be 180° on the XY plane. In other words, the systems 110 and 120 are arranged so that an angle between a component of the light emitted from the first light emission system 111 in which the component is parallel to the recording paper 100 and a component of the light emitted from the second light emission system 121 in which the component is parallel to the recording paper 100 is formed to be 180°.

As described above, the first measurement system 110 and the second measurement system 120 are arranged so that the illumination center by the first measurement system 110 is positioned differently from the illumination center by the second measurement system 120. The recording paper 100 is illuminated so that the light emitted from the first light emission system 111 is directed opposite to the light emitted from the second light emission system 121 on the XY plane. In detail, the recording paper 100 is illuminated in a state illustrated in FIG. 6A and FIG. 6B.

Moreover, in the optical sensor 1003 in the third embodiment, it is possible to arrange the first diffuse reflected light detection system 113 to be perpendicular to the recording paper 100 at the illumination center by the first measurement system 110, and also, it is possible to arrange the second diffuse reflected light detection system 123 to be perpendicular to the recording paper 100 at the illumination center by the second measurement system 120. Even in the above described arrangement, the first diffuse reflected light detection system 113 does not interfere with the second diffuse reflected light detection system 123 in the optical sensor 1003.

Configurations other than the above described configuration in the third embodiment are the same as the configurations in the first embodiment, and the explanation thereof will be omitted.

Fourth Embodiment

Figure 20:
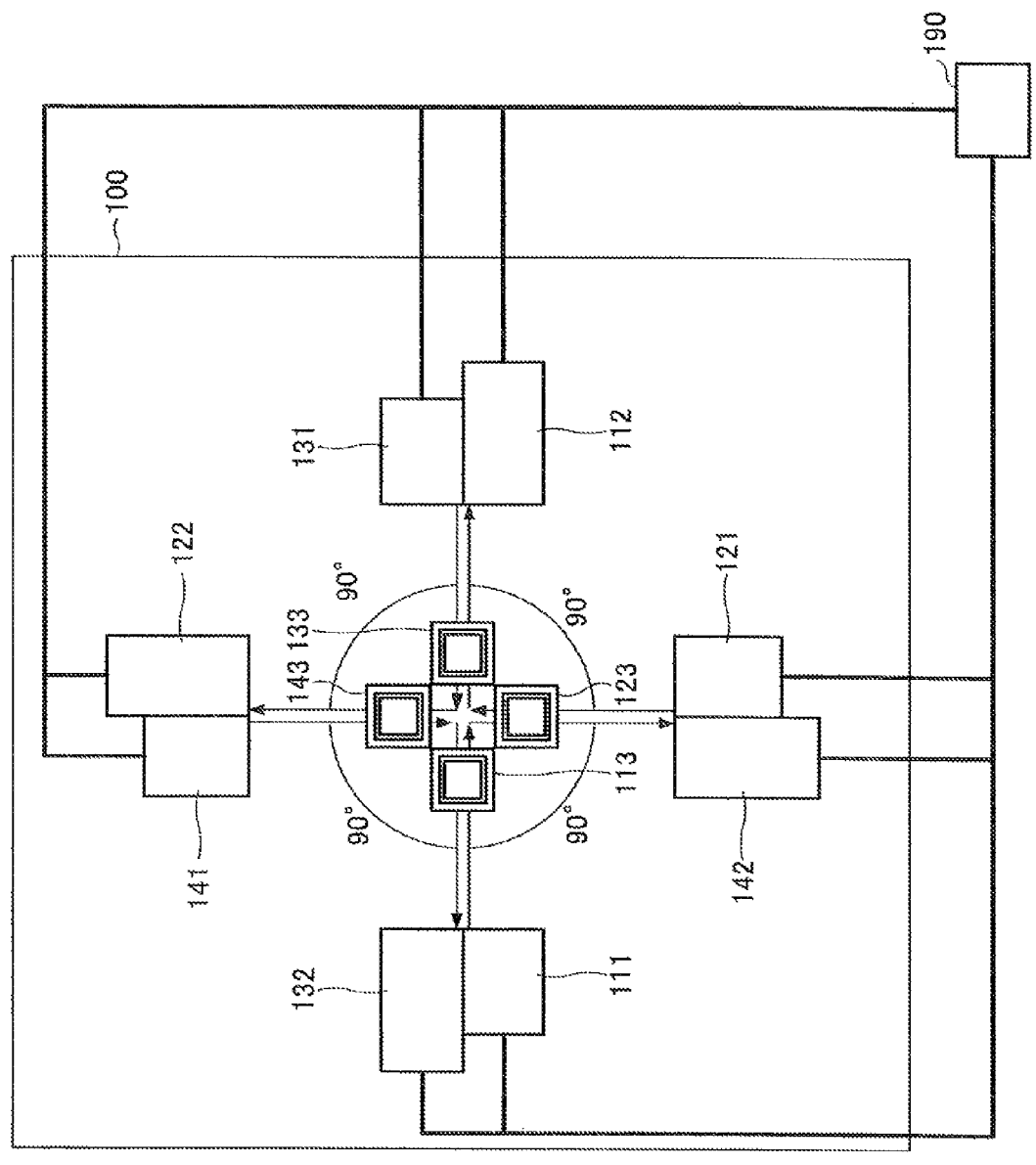
FIG. 20 is a top view of the optical sensor in a fourth embodiment.

Next, a fourth embodiment will be described. The fourth embodiment will be described with reference to FIG. 20. An optical sensor 1004 in the fourth embodiment includes four measurement systems similar to the first measurement system 110 and the second measurement system 120.

In the optical sensor 1004 in the fourth embodiment, light paths respective to the four measurement systems are arranged to mutually form angles of 90° on the XY plane. In detail, a first measurement system and a second measurement system are arranged so that the light path of the light emitted from the first light emission system 111 and the light path of the light emitted from the second light emission system 121 form an angle of 90° on the XY plane. That is, the first measurement system and the second measurement system are arranged so that an angle between a component of the light emitted from the first light emission system 111 in which the component is parallel to the recording paper 100 and a component of the light emitted from the second light emission system 121 in which the component is parallel to the recording paper 100 is formed to be 90°.

Moreover, a third measurement system is formed by a third light emission system 131, a third specular reflected light detection system 132, and a third diffuse reflected light detection system 133. The third measurement system is arranged so that the light path of the light emitted from the first light emission system 131 forms an angle of 180° on the XY plane with the light path of light emitted from the third light emission system 131. That is, the third measurement system is arranged so that an angle between the component of the light emitted from the first light emission system 111 in which the component is parallel to the recording paper 100 and a component of the light emitted from the third light emission system 131 in which the component is parallel to the recording paper 100 is formed to be 180°.

Furthermore, a fourth measurement system is formed by a fourth light emission system 141, a fourth specular reflected light detection system 142, and a fourth diffuse reflected light detection system 143. The fourth measurement system is arranged so that the light path of the light emitted from the second light emission system 121 forms an angle of 180° on the XY plane with light path of light emitted from the fourth light emission system 141. That is, the fourth measurement system is arranged so that an angle between the component of the light emitted from the second light emission system 121 in which the component is parallel to the recording paper 100 and a component of the light emitted from the fourth light emission system 141 in which the component is parallel to the recording paper 100 is formed to be 180°.

The third light emission system 131 and the fourth light emission system 141 are equivalent to the first light emission system 111. The third specular reflected light detection system 132 and the fourth specular reflected light detection system 142 are equivalent to the first specular reflected light detection system 112. The third diffuse reflected light detection system 133 and the fourth diffuse reflect light detection system 143 are equivalent to the first diffuse reflected light detection system 113.

In the fourth embodiment, the first light emission system 111 interferes with the third specular reflected light detection system 132 in their locations. The second light emission system 121 interferes with the fourth specular reflected light detection system 142 in their locations. The third light emission system 131 interferes with the first specular reflected light detection system 112 in their locations. The fourth light emission system 141 interferes with the second specular reflected light detection system 123 in their locations. In order to prevent location interference, a distances from the first light emission system 111 to its illumination center is set to be a different distance from the third specular reflected light detection system 132 to its illumination center. Alternatively, the light emitted from the first light emission system 111 is reflected by a mirror or the like to illuminate its illumination center. The similar manner is applied to other location interferences.

In the fourth embodiment, in a case of emitting the light from the third light emission system 131 onto the recording paper 100, a signal level of an output signal of a photodetector of the third specular reflected light detection system 132 is denoted by "S31", and a signal level of an output signal of a photodetector of the third diffuse reflected light detection system 133 is denoted by "S32". Also, in a case of emitting the light from the fourth light emission system 141 onto the recording paper 100, a signal level of an output signal of a photodetector of the fourth specular reflected light detection system 142 is denoted by "S41", and a signal level of an output signal of a photodetector of the fourth diffuse reflected light detection system 143 is denoted by "S42".

In this case, as described above, the signal levels S11 and S31 may be the same, and the signal levels S21 and S41 may be the same. In the fourth embodiment, the signal levels S11, S21, S12, and S22 in the first embodiment are replaced with the signal levels S11 (or S31), S21 (or S41), an average value of the signal levels S12 and S32, and an average value of the signal levels S22 and S42. Thus, it is possible to perform a method for identifying the recording paper 100 similarly to that in the first embodiment.

Configurations other than the above described configuration in the fourth embodiment are the same as the configurations in the first embodiment and the second embodiment, and the explanation thereof will be omitted.

Fifth Embodiment

Figure 21:
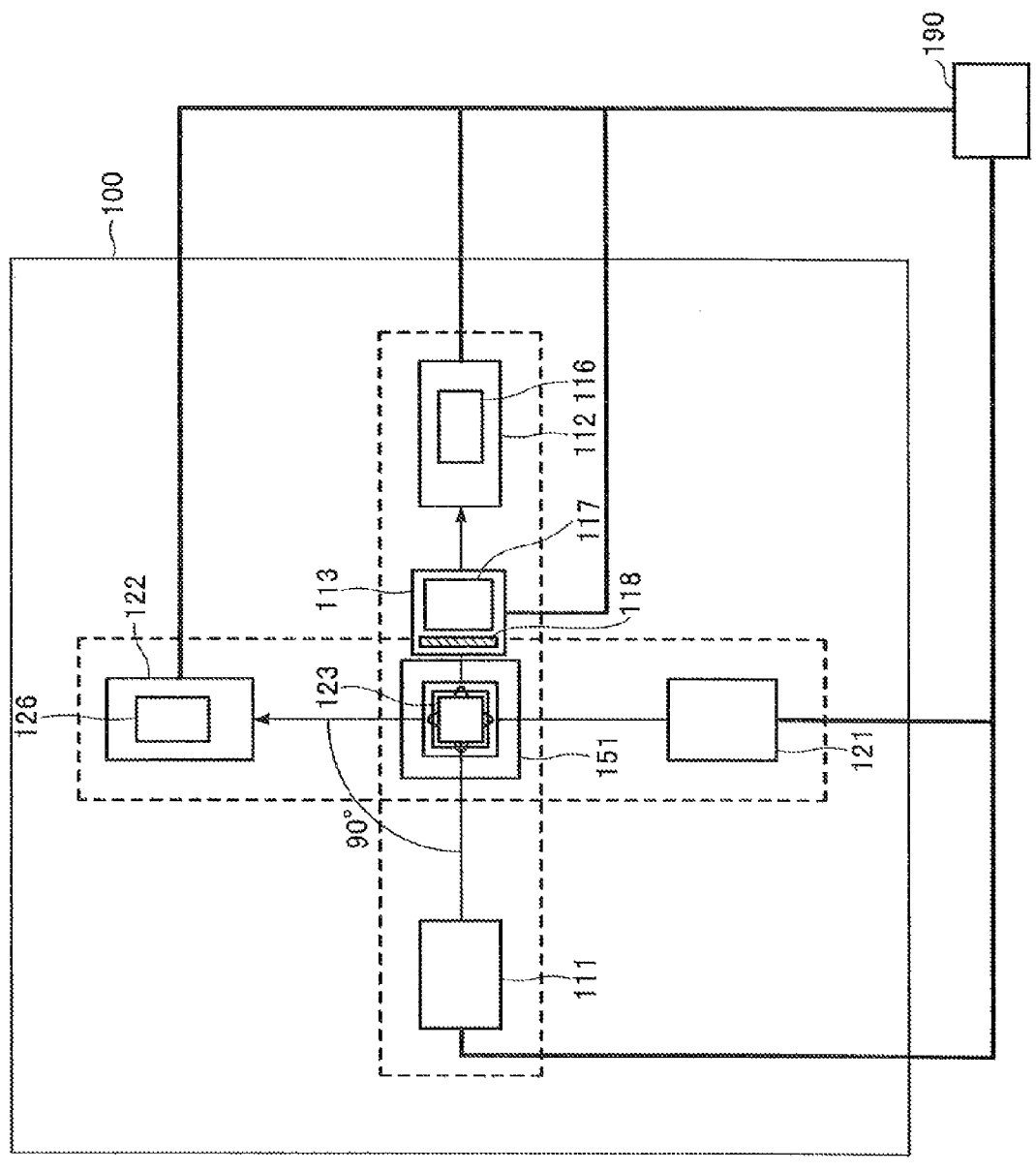
FIG. 21 is a top view of the optical sensor in a fifth embodiment.
Figure 22:
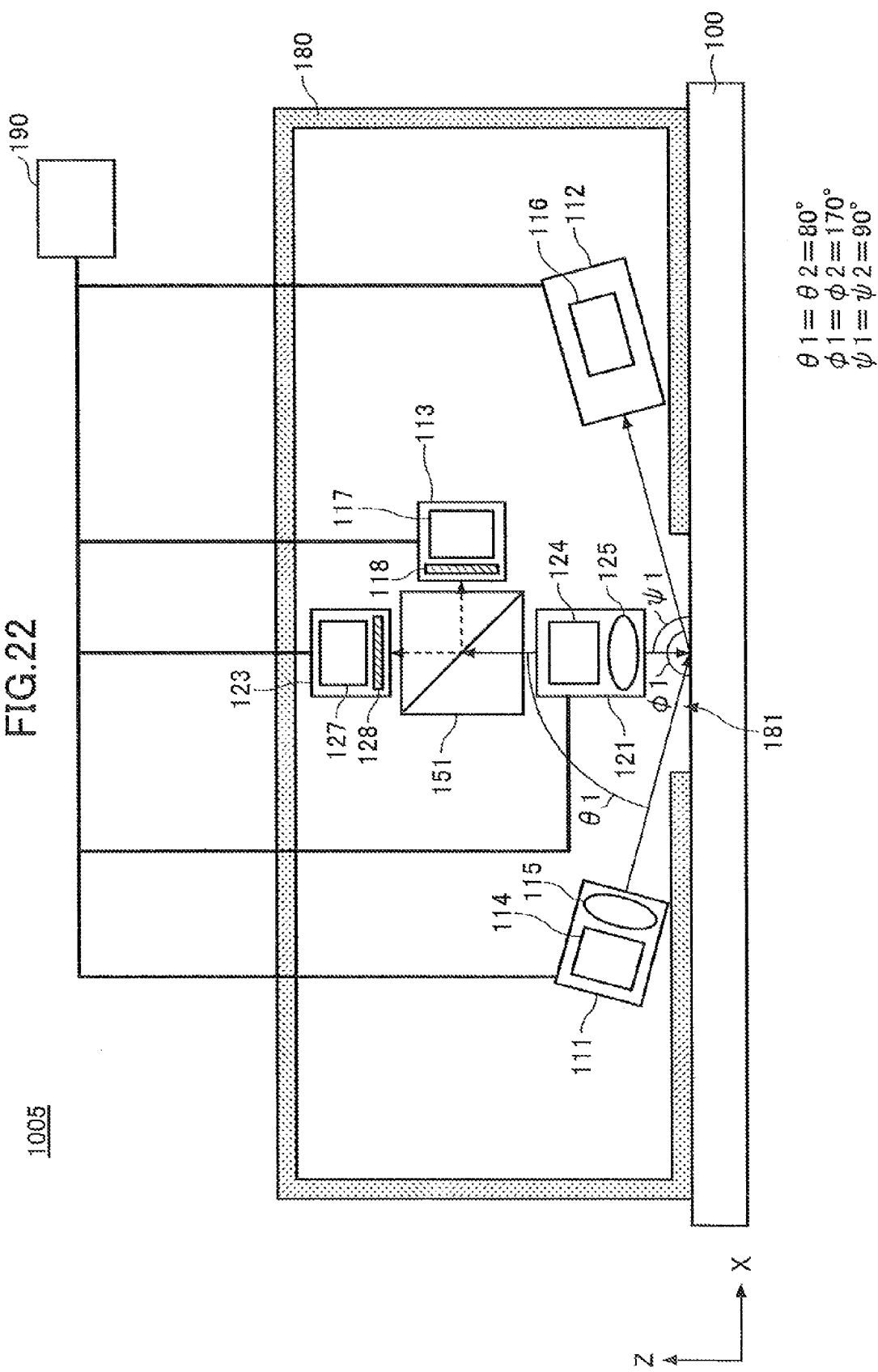
FIG. 22 is a lateral view of the optical sensor in the fifth embodiment.

Next, a fifth embodiment will be described. An optical sensor 1005 in the fifth embodiment includes two measurement systems. In the optical sensor 1005, light divided by a beam splitter enters the first diffuse reflected light detection system 113 and the second diffuse reflected light detection system 123. The optical sensor 1005 in the fifth embodiment will be described with reference to FIG. 21 and FIG. 22.

In the optical sensor 1005 in the fifth embodiment, the first light emission system 111 and the first specular reflected light detection system 112 are located similarly to those in the second embodiment. Also, the second light emission system 121 and the second specular reflected light detection system 122 are located similarly to those in the second embodiment. In the fifth embodiment, a beam splitter 151 is provided perpendicularly to the surface of the recording paper 100 at the radiation center. By using the beam splitter 151, light entering the beam splitter 151 may be divided into light straight through the beam splitter 151 and light polarized by the beam splitter 151. The light polarized by the beam splitter 151 enters the first diffuse reflected light detection system 113, and the light straight through the beam splitter 151 enters the second diffuse reflected light detection system 123. By this configuration, it is possible to detect the diffuse reflected light in which the light amount of the diffuse reflected light becomes maximum in a direction perpendicular to the surface of the recording paper 100.

Polarization directions of the lights emitted from the first light emission system 111 and the second light emission system 121 are regarded as predetermined directions, respectively. The lights are emitted at predetermined timing by the first light emission system 111 and the second light emission system 121. Thus, a polarization beam splitter may be applied as the beam splitter 151. In this case, the polarizing filter 118 (FIG. 21) in the first diffuse reflected light detection system 133 and the polarizing filter 128 (FIG. 22) in the second diffuse reflected light detection system 123 may not be provided.

Configuration other than the above described configuration in the fifth embodiment are the same as the configurations in the first embodiment and the second embodiment, and the explanation thereof will be omitted.

Sixth Embodiment

Figure 23:
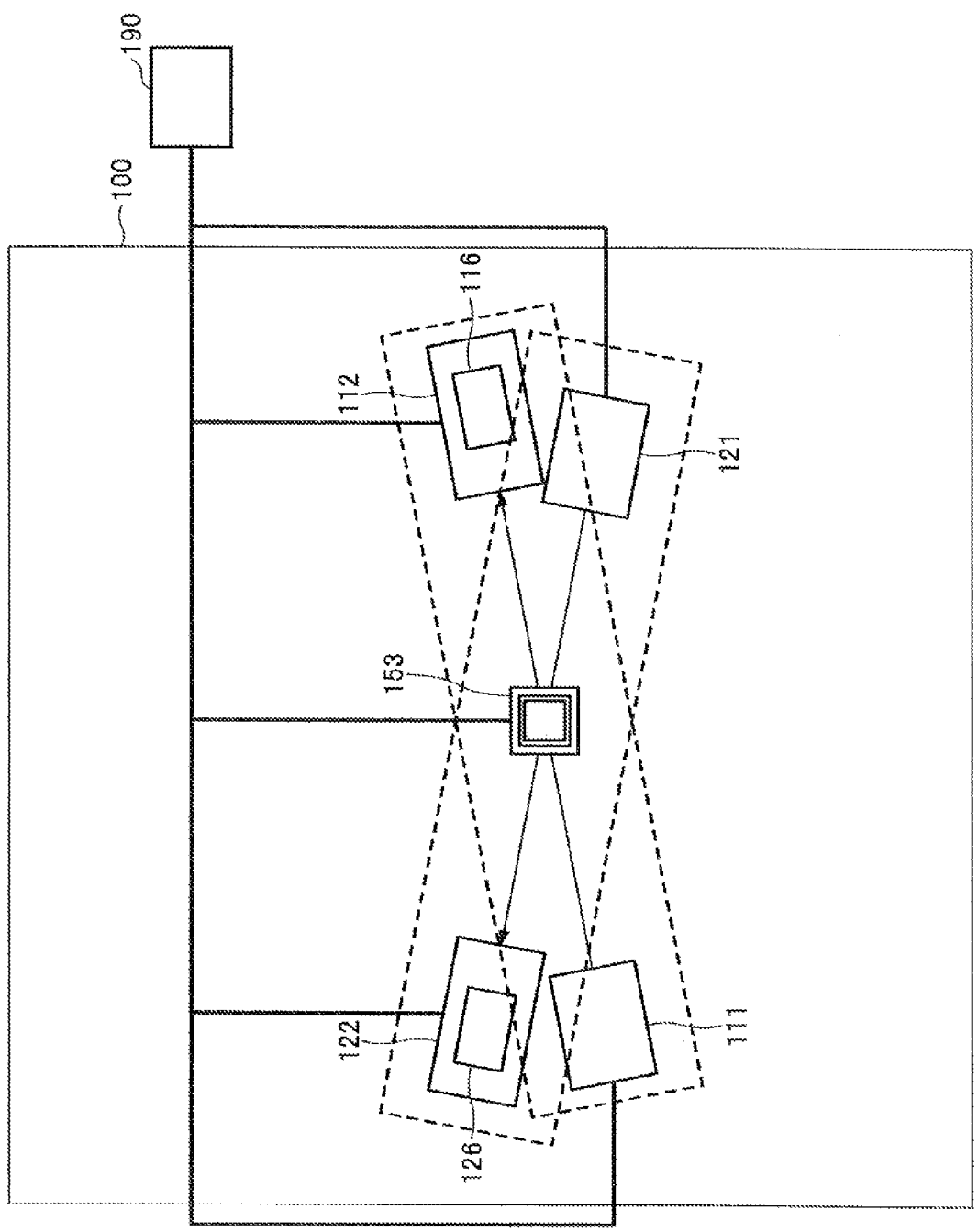
FIG. 23 is a top view of the optical sensor in a sixth embodiment.

Next, a sixth embodiment will be described. An optical sensor 1006 in the sixth embodiment includes two measurement systems. In the optical sensor 1006, the first diffuse reflected light detection system 113 and the second diffuse reflected light detection system 123 are formed as one detection system. The optical sensor 1006 in the sixth embodiment will be described with reference to FIG. 23 and FIG. 24.

In the optical sensor 1006 in the sixth embodiment, the first light emission system 111 and the first specular reflected light detection system 112 are located similarly to those in the first embodiment. Also, the second light emission system 121 and the second specular reflected light detection system 122 are located similarly to those in the first embodiment.

In the sixth embodiment, a diffuse reflected light detection system 153 is arranged in a perpendicular direction at the illumination center on the recording paper 100. The diffuse reflected light detection system 153 includes a photodetector 157 formed by a light receiving element such as the photo diode or the like, and a polarizing filter 158 in front of the photodetector 157. The photodetector 157 is the same as the photodetector 117 or the like. The polarizing filter 158 is the same as the polarizing filter 118.

Figure 24:
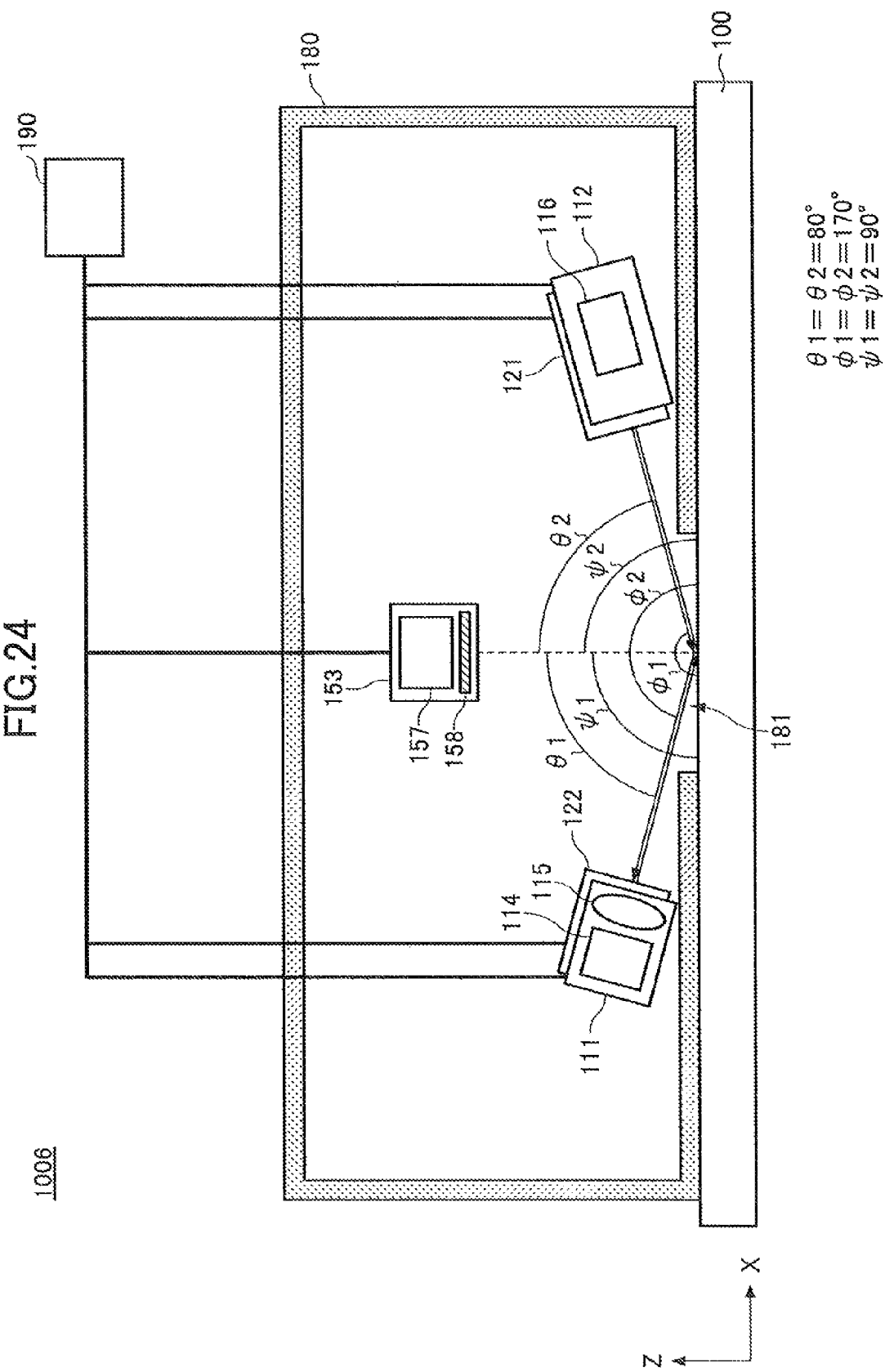
FIG. 24 is a lateral view of the optical sensor in the sixth embodiment.

In the sixth embodiment, as illustrated in FIG. 24, light emissions of the first light emission system 111 and the second light emission system 121 are controlled. The control part 190 controls the diffuse reflected light detection system 153 to detect timing. It is possible to separately detect the signal levels S12 and S22. By this configuration, the diffuse reflected light detection system 153 may be formed as one system. Thus, it is possible to realize the optical sensor 1006 of which the size is reduced and to realize a further lowered cost.

Configurations other than the above described configuration in the sixth embodiment are the same as the configurations in the first embodiment and the second embodiment, and the explanation thereof will be omitted. Also, the sixth embodiment may be applied to the second embodiment.

Seventh Embodiment

Figure 25:
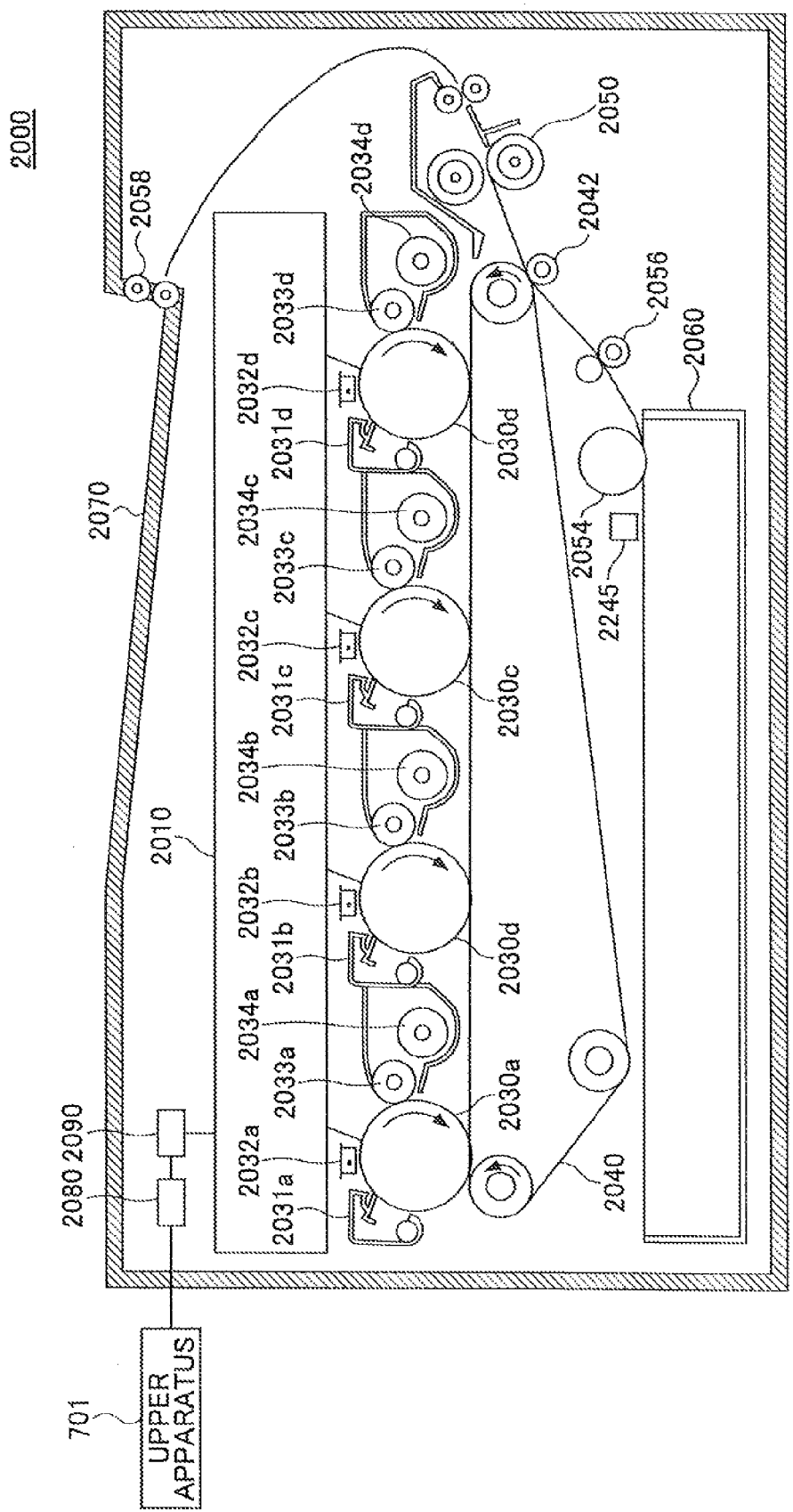
FIG. 25 is a diagram illustrating a configuration of a color printer in a seventh embodiment.

Next, a seventh embodiment will be described. In the seventh embodiment, an image forming apparatus, which includes any one of the optical sensor 1001 through 1006 described in the first through sixth embodiments, is included. As illustrated in FIG. 25, the image forming apparatus in the seventh embodiment is regarded as a color printer 2000.

The color printer 2000 may be a multicolor printer of a tandem system to form a full-color image by overlapping four colors (black, cyan, magenta, and yellow). The color printer 2000 includes an optical scanner 2010, four photosensitive drums 2030a, 2030b, 2030c, and 2030d, four cleaning units 2031a, 2032b, 2032c, and 2032d, four charging devices 2032a, 2032b, 2032c, and 2032d, four developing rollers 2033a, 2033b, 2033c, and 2033d, four toner cartridges 2034a, 2034b, 2034c, and 2034d, a transfer belt 2040, a transfer roller 2042, a fixing device 2050, a feeding roller 2054, a pair of registration rollers 2056, a pair of paper ejection rollers 2058, a paper feed tray 2060, an ejection tray 2070, a communication control device 2080, an optical sensor 2245, and a printer control device 2090.

The communication control device 2080 controls communication with an upper apparatus 701 (for example, a personal computer) through a network.

The printer control device 2090 includes a CPU (Central Processing Unit), a ROM (Read-Only Memory), a RAM (Random Access Memory), and at A/D converter, and the like. The ROM stores a program described in code interpretable by the CPU and various data used to execute the program. The RAM is regarded as a memory used as a working area. The A/D convertor converts analog data into digital data. Thus, the printer control device 2090 controls each of component parts in response to a request sent from the upper apparatus 701, and sends image information sent from the upper apparatus 701 to the optical scanner 2010.

The photosensitive drum 2030a, the charging device 2032a, the developing roller 2033a, the toner cartridge 2034a, and the cleaning unit 2031a are used as one unit, and form an image formation station for forming a black image (hereinafter, may be called "K station").

The photosensitive drum 2030b, the charging device 2032b, the developing roller 2033b, the toner cartridge 2034b, and the cleaning unit 2031b are used as one unit, and form an image formation station for forming a cyan image (hereinafter, may be called "C station").

The photosensitive drum 2030c, the charging device 2032c, the developing roller 2033c, the toner cartridge 2034c, and the cleaning unit 2031c are used as one unit, and form an image formation station for forming a magenta image (hereinafter, may be called "M station").

The photosensitive drum 2030d, the charging device 2032d, the developing roller 2033d, the toner cartridge 2034d, and the cleaning unit 2031d are used as one unit, and form an image formation station for forming a yellow image (hereinafter, may be called "Y station").

On each surface of the photosensitive drums 2030a, 2030b, 2030c, and 2030d, a photosensitive layer is formed. That is, each surface of the photosensitive drums 2030a, 2030b, 2030c, and 2030d is a target to be scanned. The photosensitive drums 2030a, 2030b, 2030c, and 2030d are rotated by a rotation mechanism (not shown) in directions indicated by arrows, as illustrated in FIG. 25.

The charging devices 2032a, 2032b, 2032c, and 2032d uniformly charge surfaces of the photosensitive drums 2030a, 2030b, 2030c, and 2030d, respectively.

The optical scanner 2010 illuminates the surfaces of the photosensitive drums 2030a, 2030b, 2030c, and 2030d with light fluxes modulated for individual colors based on multicolor image information (black image information, cyan image information, magenta image information, and yellow image information) sent from the upper apparatus 701. By this configuration, electric charges extinct only on portions illuminated by light on the surfaces of the photosensitive drums 2030a, 2030b, 2030c, and 2030d. Latent images for individual image information are formed on the surfaces of the photosensitive drums 2030a, 2030b, 2030c, and 2030d. The formed latent images are moved toward the developing rollers 2033a, 2033b, 2033c, and 2033d, respectively, along rotations of the photosensitive drums 2030a, 2030b, 2030c, and 2030d.

The toner cartridge 2034a stores black toner, and the black toner is supplied to the developing roller 2033a. The toner cartridge 2034b stores cyan toner, and the cyan toner is supplied to the developing roller 2033b. The toner cartridge 2034c stores magenta toner, and the magenta toner is supplied to the developing roller 2033c. The cartridge toner 2034d stores yellow toner, and the yellow toner is supplied to the developing roller 2033d.

Along a rotation of the developing roller 2033a, toner supplied from respective toner cartridge is applied thinly and uniformly on a surface thereof. Thus, when the toner on the surface of the developing roller 2033a contacts the photosensitive drum 2030a, toner is transferred and adhered onto portions alone illuminated by the light. That is, the toner is adhered by the developing roller 2033a onto the latent image formed on the surface of the photosensitive drum 2030a, to be visualized. An image (toner image), where the toner is adhered, is moved toward the transfer belt 2040 along the rotation of the photosensitive drum 2030a. Operations of the photosensitive drums 2030b, 2030c, and 2030d and the developing rollers 2033b, 2033c, and 2033d are the similar to the above described operations of the photosensitive drum 2030a and the developing roller 2033a.

Toner images for yellow, magenta, cyan, and black are sequentially transferred onto the transfer belt 2040 at a predetermined timing, and are overlapped with each other, thereby a multicolor image is formed.

The paper feed tray 2060 stores a plurality of the recording papers 100. In vicinity of the paper feed tray 2060, the feeding roller 2054 is arranged. The feeding roller 2054 picks out each of the recording papers 100 one by one to convey to the pair of the registration rollers 2056. The pair of the registration rollers 2056 sends out the recording paper 100 toward a gap between the transfer belt 2040 and the transfer roller 2042 at a predetermined timing. By this configuration, a color image formed on the transfer belt 2040 is transferred to the recording paper 100. The recording paper 100, on which the color image is transferred, is carried to the fixing device 2050.

The fixing device 2050 applied heat and pressure to the recording paper 100. Then, the toner is fixed on the recording paper 100. The recording paper 100 is carried to the ejection tray 2070 through the pair of paper ejection rollers 2058, and is stacked on the ejection tray 2070.

The cleaning unit 2031a removes residual toner on the surface of the photosensitive drum 2030a. After the residual toner is removed, the surface of the photosensitive drum 2030a returns to a position facing the charging device 2032a. The cleaning units 2031b, 2031c, and 2031d operate similar to the cleaning unit 2031a.

The optical sensor 2245 is used to specify the name, the smoothness, the thickness, the density, and the like of the recording papers 100 accommodated in the paper feed tray 2060. In detail, in a configuration of specifying the name, the smoothness, the thickness, the density, and the like of the recording papers 100 inside the color printer 2000, these items are specified based on information such as numeric values and the like acquired by the optical sensor 2245. Accordingly, the printer control device 2090 and the like may include a function as the adjustment device for adjusting an image formation condition.

The optical sensor 2245 corresponds to one of the optical sensors 1001 through 1006 in the first through sixth embodiment. Since the image forming apparatus in the seventh embodiment mounts one of the optical sensors 1001 through 1006 in the first through sixth embodiment, it is possible to identify the recording paper 100 at higher accuracy with a lower cost. Accordingly, it is possible to realize the image forming apparatus capable of identifying the recording paper 100 at higher accuracy with the lower cost. Also, since the optical sensors 1001 through 1006 in the first through sixth embodiment are small size, the size of the entirety of the image forming apparatus may not be larger.

Also, in the seventh embodiment, in a case in which an identification level of the optical sensor 2245 is sufficient to specify the non-coated paper, the coated paper, or the OHP sheet, the polarizing filter in each of the diffuse reflected light detection system may not be provided. By using the surface emitting laser array, compared to the case of one light emitting element, it is possible to illuminate the recording paper 100 with a greater light amount of the light. It is possible to improve the S/N in the reflected light amount, and to improve the identification accuracy of the recording paper 100. By simultaneously lighting on multiple light emitting elements, the contrast ratio of the speckle pattern can be reduced, and the reflected light amount at the recording paper 100 can be accurately detected. Thus, it is possible to further improve the accuracy of identifying the recording paper 100. Furthermore, in the case of using the surface emitting laser array, it becomes possible to realize a higher integration, which has been difficult to realize by using the LED in the related art. That is, since all laser beams are condensed in a vicinity of an optical axis of a collimate lens, it is possible to approximately collimate multiple light fluxes with a constant incident angle. Thus, it is possible to easily realize a collimate optical system.

Figure 26:
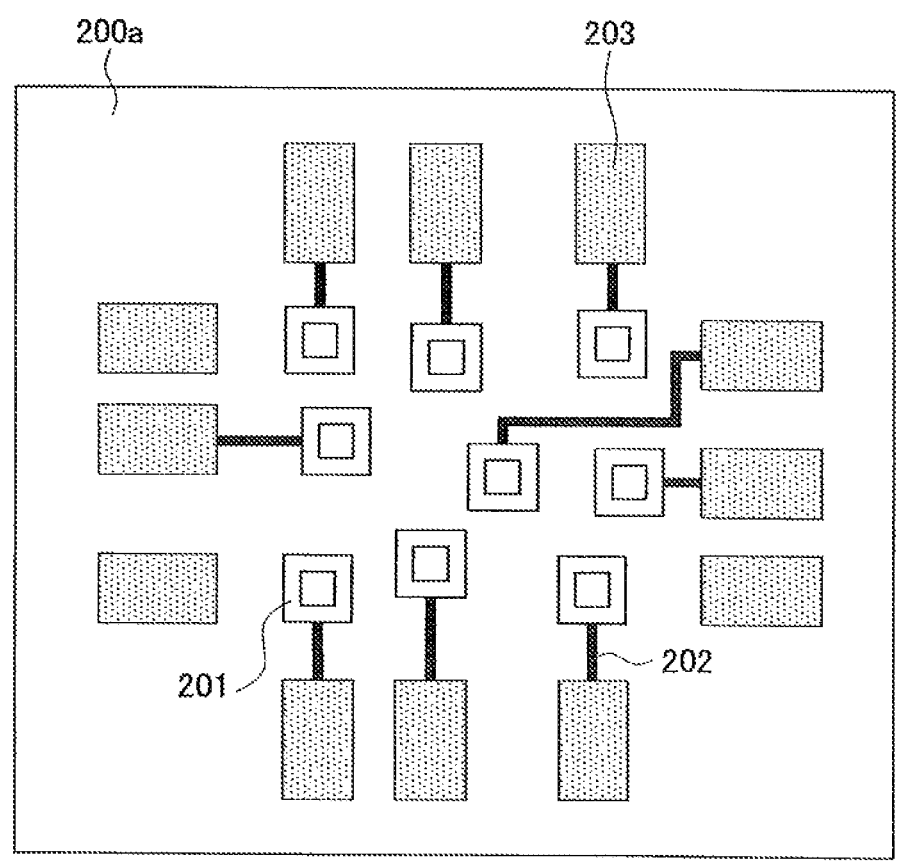
FIG. 26 is a diagram for explaining a surface emitting laser array in which light emitting elements are not equally spaced.

In the seventh embodiment, as illustrated in FIG. 26, in multiple of light emitting elements 201 in a surface emitting laser array 200a, one of intervals among the light emitting elements 201 may be different from other intervals. In this case, regularity of the speckle pattern is disturbed, and it is possible to further reduce the contrast ratio of the speckle pattern. In other words, in the seventh embodiment, it is preferable that the intervals among the light emitting elements 201 are different from each other.

Figure 27:
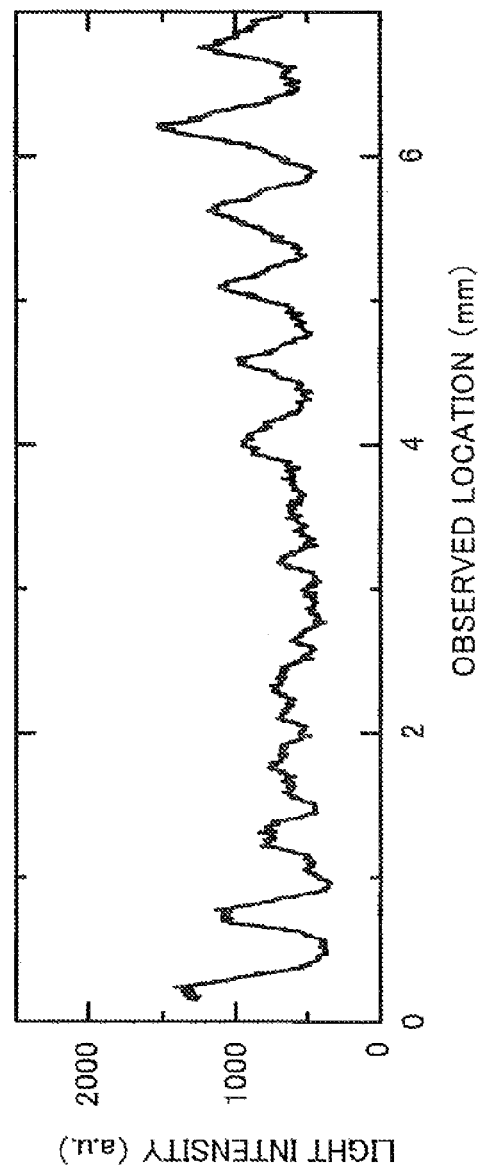
FIG. 27 is a diagram for explaining a light intensity distribution of the speckle pattern in a case in which the light emitting elements are equally spaced.

In a light source including a surface emitting laser array in which five light emitting elements are arrayed in one dimension and the five light emitting elements are equally spaced, a light intensity distribution, which is acquired by observing the speckle pattern with a beam profiler, is illustrated in FIG. 27. In this case, a periodical change of the light intensity distribution, which corresponds to the regularity of an arrangement of the light emitting elements, is confirmed. The contrast ratio indicates 0.64 in this case.

Figure 28:
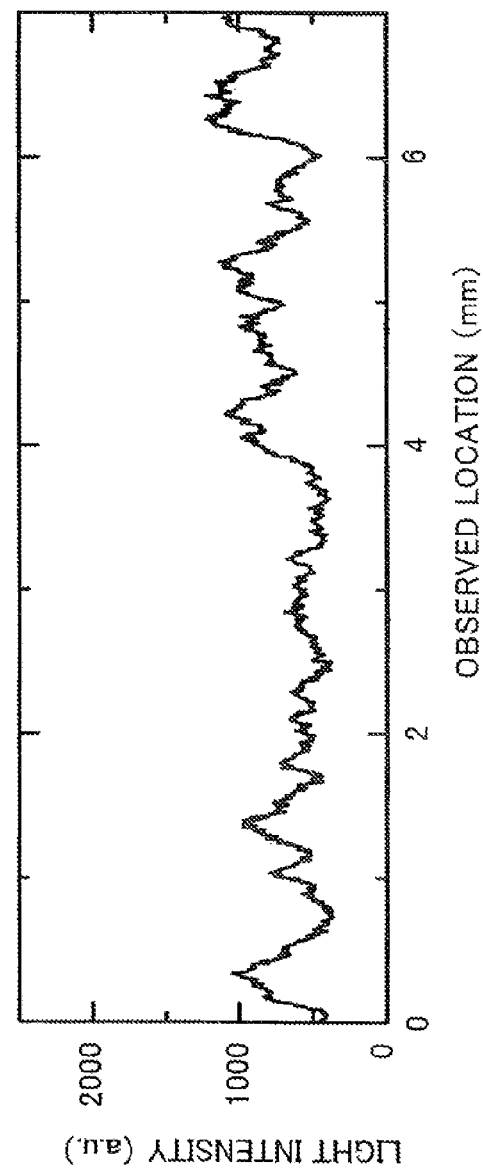
FIG. 28 is a diagram for explaining a light intensity distribution of the speckle pattern in a case in which the light emitting elements are not equally spaced.

Also, in the light source including the surface emitting laser array in which the five light emitting elements are arrayed in one dimension and the five light emitting elements are irregularly arranged with a ratio of 1.0:1.9:1.3:0.7, the light intensity distribution, which is acquired by observing the speckle pattern with the beam profiler, is illustrated in FIG. 28. In this case, it is confirmed that the periodical change of the light intensity distribution is suppressed. In this case, the contrast ratio indicates 0.56, and is reduced more than the case of arranging the light emitting elements with an equal interval.

As described above, for the surface emitting laser or the like including the multiple light emitting elements, the multiple light emitting elements are not equally spaced and are irregularly arranged. Thus, it is possible to further suppress the speckle pattern.

In the seventh embodiment, it is preferable to arrange a condensing lens in front of each light receiving part in the photodetector. By this configuration, it is possible to reduce a change of a detected light amount by condensing light.

In an optical sensor for identifying the recording paper 100 based on the light amount of reflection, reproducibility of measurement is important. In the optical sensor for identifying the recording paper 100 based on the light amount of reflection, each measurement system is provided on an assumption on which a measurement plane and the surface of the recording paper 100 are on the same plane. However, due to arcuation, vibration, or the like, the surface of the recording paper 100 may incline with respect to the measurement plane or may depart from the measurement plane. Thus, a case, in which the measurement plane and the surface of the recording paper 100 may not be on the same plane, may be caused. In an actual measurement, since the reflected light amount changes, it is not possible to stably identify the recording paper 100. As an example, the specular reflection will be described.

Figure 29C:
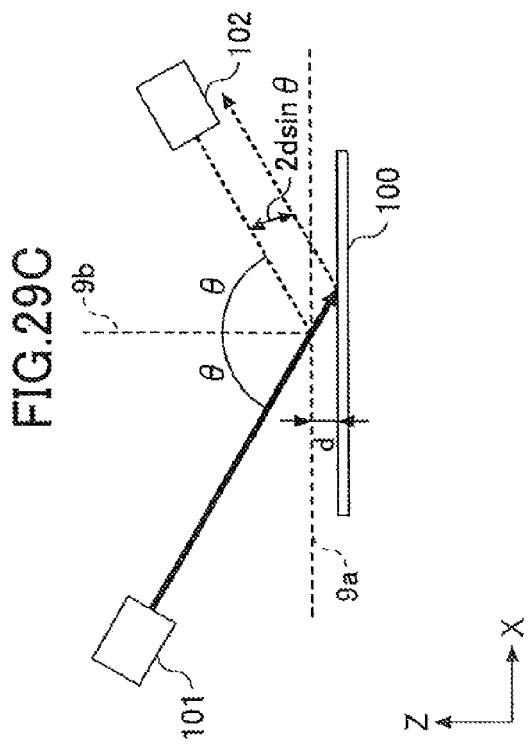
FIG. 29A, FIG. 29B, and FIG. 29C are diagrams for explaining a change of a detected light amount due to a displacement between a measurement plane and a surface of the recording medium.
Figure 29A:
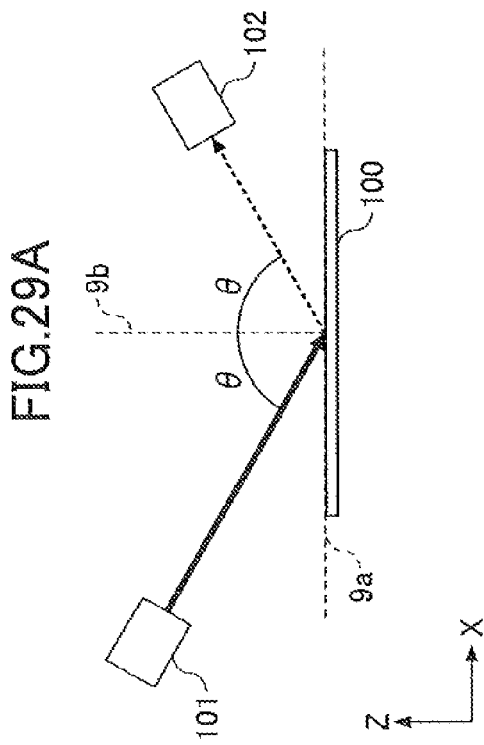

As illustrated in FIG. 29A, in a case in which a measurement plane 9a and the surface of the recording paper 100 are on the same plane, since radiation light emitted from a light emitting system 101 is specularly reflected at the recording paper 100, a specular reflection detection system 102 can receive and detect a specular reflected light.

Figure 29B:
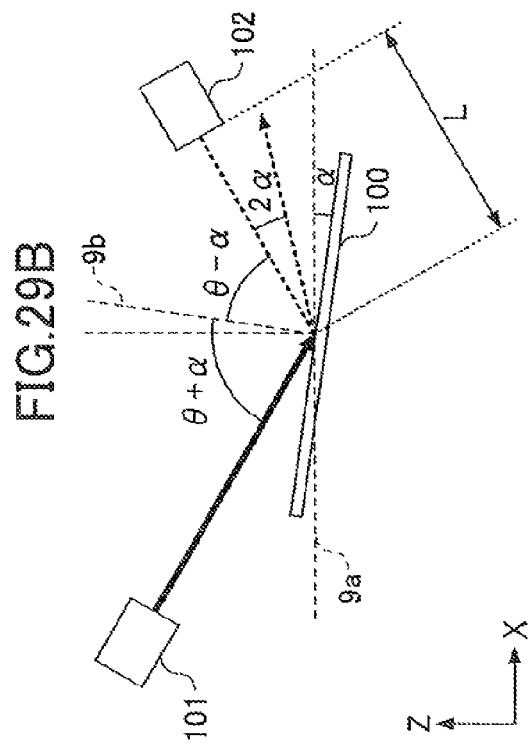

On the contrary, as illustrated in FIG. 29B, in a case in which the surface of the recording paper 100 inclines at an angle α alone with respect to the measurement plane 9a, similar to the case illustrated in FIG. 29A, when the light emitting system 101 and the specular reflection detection system 102 are arranged, light specularly reflected at the recording paper 100 advances to a direction displaced by an angle of 2α with respect to a light path of a predetermined reflected light. Thus, light received by the specular reflection detection system 102 is displaced by the angle of 2α with respect to a light path of the specularly reflected light at the recording paper 100. That is, when L denotes a distance between a center of the irradiation area and the specular reflection detection system 102, the specular reflection detection system 102 detects light at a location displace by L×tan 2α. Since an actual incident angle is displaced by α from a predetermined incident angle θ with respect to a perpendicular line 9b, a reflectance on the recording paper 100 also changes. Accordingly, the light amount detected by the specular reflected light detection system 102 changes, it becomes difficult to identify the recording paper 100 in detail.

Also, FIG. 29C illustrates a case in which the surface of the recording paper 100 is displaced by d in height with respect to the measurement plane 9a, that is, a case the surface of the recording paper 100 is displaced in a Z-axis direction. In this case, if the light emitting system 101 and the specular reflection detection system 102 are arranged similar to an arrangement in FIG. 29A, the light path of the specular reflected light is displaced by 2d×sin θ. Accordingly, for the light path of the specular reflected light from the recording paper 100, the specular reflected light detection system 102 detects the light at a location displaced by 2d×sin θ. As a result, the light amount detected by the specular reflected light detection system 102 is changed. Thus, it may be difficult to identify the recording paper 100 in detail.

Accordingly, in order to certainly detect the specular reflected light from the recording paper 100 at the specular reflected light detection system 102, the condensing lens is arranged in front of the light receiving part of the specular reflected light detection system 102. By this configuration, the measurement plane 9a is displaced with the recording paper 100. Thus, even if the light path of the specular reflected light is displaced, it is possible to certainly enter the specular reflected light to the light receiving part of the specular reflected light detection system 102.

Also, by using the photo diode (PD), in which a light receiving area is sufficiently large, even if the light path of the specular reflected light is displaced, it may be formed to receive the specularly reflected light in the light receiving area. Also, a beam diameter of the irradiated light may be made to be narrower.

Also, by using the photo diodes being arrayed to the light receiving part of the specular reflected light detection system 102, for a displacement of the light path of the specular reflected light, the light receiving area may be formed to be sufficiently large. In this case, even if the light of the specular reflected light is displaced, the greatest light signal may be regarded as a signal of the specular reflected light in light signals detected by each of the photo diodes. Also, in a case of arraying the photo diodes, it is possible to form the light receiving area to be smaller for each of the photo diodes. Thus, it is possible to reduce fluctuation of an output to a displacement between the specular reflected light and the center of the light receiving area, and it is possible to realize a further precise detection.

Also, in the above, the specular reflected light is described. In the surface diffuse reflection and the internal diffuse reflection, a displacement between the measurement plane 9a and the surface of the recording paper 100 is caused. It is possible to apply the same manner to the surface diffuse reflection and the internal diffuse reflection.

In the above described embodiments, the optical sensor, in which the light illuminating the recording paper 100 is the S-polarization, is described. The seventh embodiment is not limited to the case of the S-polarization but may be applied to a case in which the light illuminating the recording paper 100 is the P-polarization. In this case, instead of the polarizing filter, the polarizing filter for passing the S-polarization may be used.

Moreover, if the recording paper 100 may be erroneously identified due to the disturbing light and the stray light, the number of the light detection system may be increased. A light detection system for receiving the surface diffuse reflected light may be additionally arranged, and an output signal may be used to identify the recording paper 100.

Furthermore, in the optical sensors 1001 through 1006 in the above described embodiments, the light paths of the irradiated light and the reflected light may be bent by a mirror. In this case, a center point of the photodetector is arranged on the bent light path. In this case, a member is not needed to support the light source and the photodetector which are inclined, and it is possible to simplify an electric circuit. It is also possible to reduce the size of the optical sensor with a lower cost.

Also, the optical sensors 1001 through 1006 in the above described embodiments may be arranged to target the recording paper 100 layered in the paper feed tray 2060. Alternatively, the name of the recording paper 100 may be specified while being conveyed. In this case, the optical sensors 1001 through 1006 may be arranged in a vicinity of a conveying path.

Moreover, a target object identified by the optical sensors 1001 through 1006 in the above described embodiments may not be limited to the recording paper 100.

In the above, the first through seventh embodiments are described. However, the above described contents are not limited to contents of the present invention.

Eighth Embodiment

Figure 30:
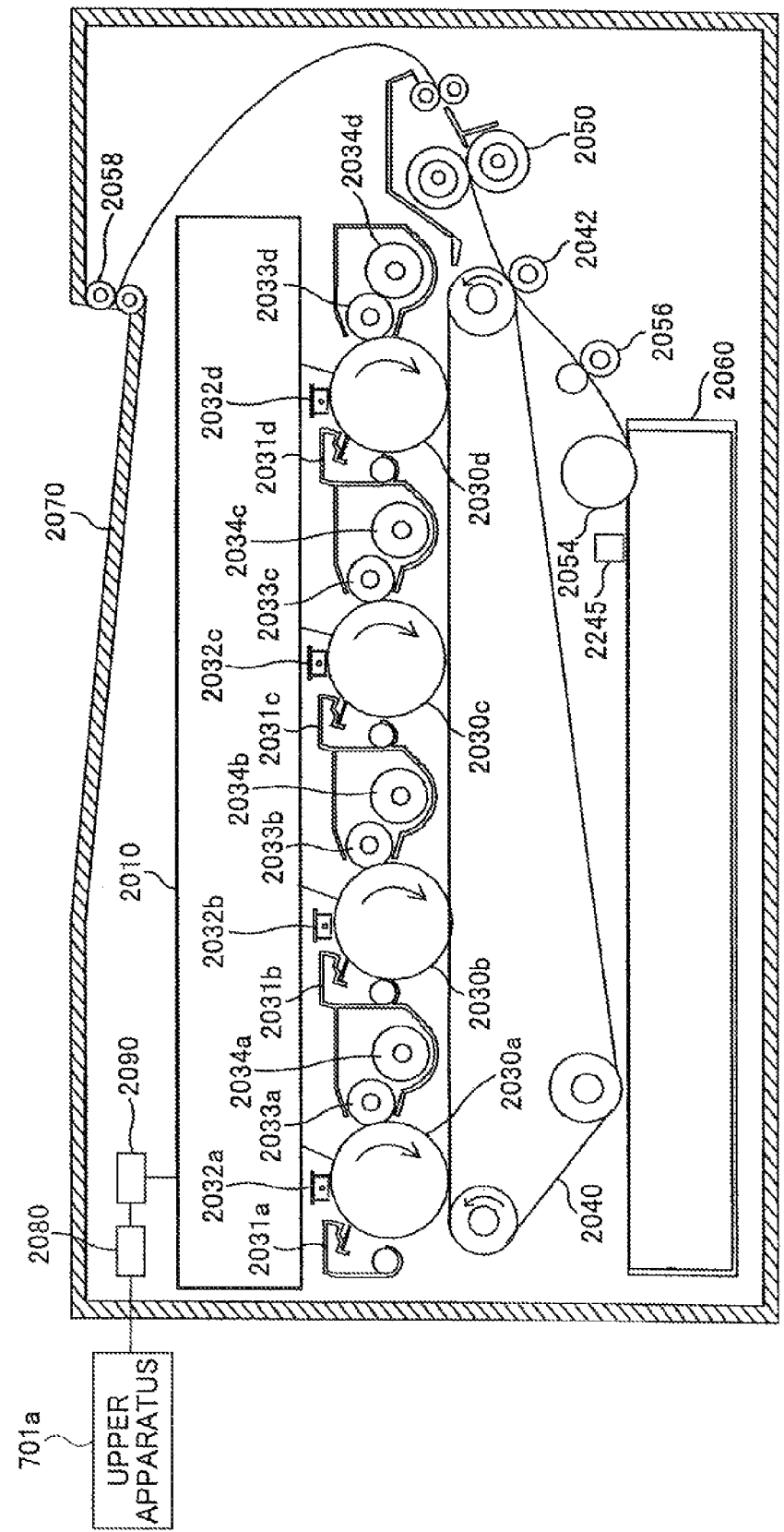
FIG. 30 is a diagram for briefly explaining a configuration of a color printer according to an eighth embodiment.

In the following, an eighth embodiment will be described with reference to FIG. 30 through FIG. 41. FIG. 30 briefly illustrates a configuration of a color printer 2000a as an image forming apparatus according to the eighth embodiment.

In FIG. 30, the color printer 2000a may be a multicolor printer of a tandem system to form a full-color image by overlapping four colors (black, cyan, magenta, and yellow). The color printer 2000a includes an optical scanner 2010, four photosensitive drums 2030a, 2030b, 2030c, and 2030d, four cleaning units 2031a, 2031b, 2031c, and 2032d, four charging devices 2032a, 2032b, 2032c, and 2032d, four developing rollers 2033a, 2033b, 2033c, and 2033d, four toner cartridges 2034a, 2034b, 2034c, and 2034d, a transfer belt 2040, a transfer roller 2042, a fixing device 2050, a feeding roller 2054, a pair of registration rollers 2056, a pair of paper ejection rollers 2058, a paper feed tray 2060, an ejection tray 2070, a communication control device 2080, an optical sensor 2245, and a printer control device 2090.

The communication control device 2080 controls communication with an upper apparatus 701 (for example, a personal computer) through a network.

The printer control device 2090 includes a CPU (Central Processing Unit), a ROM (Read-Only Memory), a RAM (Random Access Memory), and an A/D converter, and the like. The ROM stores a program described in code interpretable for the CPU and various data used to execute the program. The RAM is regarded as a memory used as a working area. The A/D convertor converts analog data into digital data. Thus, the printer control device 2090 controls each of component parts in response to a request sent from the upper apparatus 701, and sends image information sent from the upper apparatus 701 to the optical scanner 2010.

The photosensitive drum 2030a, the charging device 2032a, the developing roller 2033a, the toner cartridge 2034a, and the cleaning unit 2031a are used as one unit, and form an image formation station for forming a black image (hereinafter, may be called "K station").

The photosensitive drum 2030b, the charging device 2032b, the developing roller 2033b, the toner cartridge 2034b, and the cleaning unit 2031b are used as one unit, and form an image formation station for forming a cyan image (hereinafter, may be called "C station").

The photosensitive drum 2030c, the charging device 2032c, the developing roller 2033c, the toner cartridge 2034c, and the cleaning unit 2031c are used as one unit, and form an image formation station for forming a magenta image (hereinafter, may be called "M station").

The photosensitive drum 2030d, the charging device 2032d, the developing roller 2033d, the toner cartridge 2034d, and the cleaning unit 2031d are used as one unit, and form an image formation station for forming a yellow image (hereinafter, may be called "Y station").

On each surface of the photosensitive drums 2030a, 2030b, 2030c, and 2030d, a photosensitive layer is formed.

That is, each surface of the photosensitive drums 2030a, 2030b, 2030c, and 2030d is a target to be scanned. The photosensitive drums 2030a, 2030b, 2030c, and 2030d are rotated by a rotation mechanism (not shown) in directions indicated by arrows, as illustrated in FIG. 30.

The charging devices 2032a, 2032b, 2032c, and 2032d uniformly charge surfaces of the photosensitive drums 2030a, 2030b, 2030c, and 2030d, respectively.

The optical scanner 2010 illuminates the surfaces of the photosensitive drums 2030a, 2030b, 2030c, and 2030d with light fluxes modulated for individual colors based on multicolor image information (black image information, cyan image information, magenta image information, and yellow image information) sent from the upper apparatus 701a. By this configuration, electric charges extinct only on portions illuminated by light on the surfaces of the photosensitive drums 2030a, 2030b, 2030c, and 2030d. Latent images for individual image information are formed on the surfaces of the photosensitive drums 2030a, 2030b, 2030c, and 2030d. The formed latent images are moved toward the developing rollers 2033a, 2033b, 2033c, and 2033d, respectively, along rotations of the photosensitive drums 2030a, 2030b, 2030c, and 2030d.

The toner cartridge 2034a stores black toner, and the black toner is supplied to the developing roller 2033a. The toner cartridge 2034b stones cyan toner, and the cyan toner is supplied to the developing roller 2033b. The toner cartridge 2034c stores magenta toner, and the magenta toner is supplied to the developing roller 2033c. The toner cartridge 2034d stores yellow toner, and the yellow toner is supplied to the developing roller 2033d.

Along a rotation of the developing roller 2033a, toner supplied from the respective toner cartridge is applied thinly and uniformly on a surface thereof. Thus, when the toner on the surface of the developing roller 2033a contacts the photosensitive drum 2030a, toner is transferred and adhered only onto portions illuminated by the light. That is, the toner is adhered by the developing roller 2033a onto the latent image formed on the surface of the photosensitive drum 2030a, to be visualized. An image (toner image), where the toner is adhered, is moved toward the transfer belt 2040 along the rotation of the photosensitive drum 2030a. Operations of the photosensitive drums 2030b, 2030c, and 2030d and the developing rollers 2033b, 2033c, and 2033d are the similar to the above described operations of the photosensitive drum 2030a and the developing roller 2033a.

Toner images for yellow, magenta, cyan, and black are sequentially transferred onto the transfer belt 2040 at a predetermined timing, and are overlapped with each other, thereby the multicolor image is formed.

The paper feed tray 2060 stores a plurality of the recording papers 100. In vicinity of the paper feed tray 2060, the feeding roller 2054 is arranged. The feeding roller 2054 picks out each of the recording papers 100 one by one to convey to the pair of the registration rollers 2056. The pair of the registration rollers 2056 sends out a recording paper 1 toward a gap between the transfer belt 2040 and the transfer roller 2042 at a predetermined timing. By this configuration, a color image formed on the transfer belt 2040 is transferred to the recording paper 1. The recording paper 1, on which the color image is transferred, if carried to the fixing device 2050.

The fixing device 2050 applies heat and pressure to the recording paper 1. Then, the toner is fixed on the recording paper 1. The recording paper 1 is carried to the ejection tray 2070 through the pair of paper ejection rollers 2058, and is stacked on the ejection tray 2070.

The cleaning unit 2031a removes residual toner on the surface of the photosensitive drum 2030a. After the residual toner is removed, the surface of the photosensitive drum 2030a returns a position facing the charging device 2032a. The cleaning units 2031b, 2033c, and 2031d operate similar to the cleaning unit 2031a.

The optical sensor 2245 is used to specify the name and the like of the recording papers 100 accommodated in the paper feed tray 2060.

Figure 31:
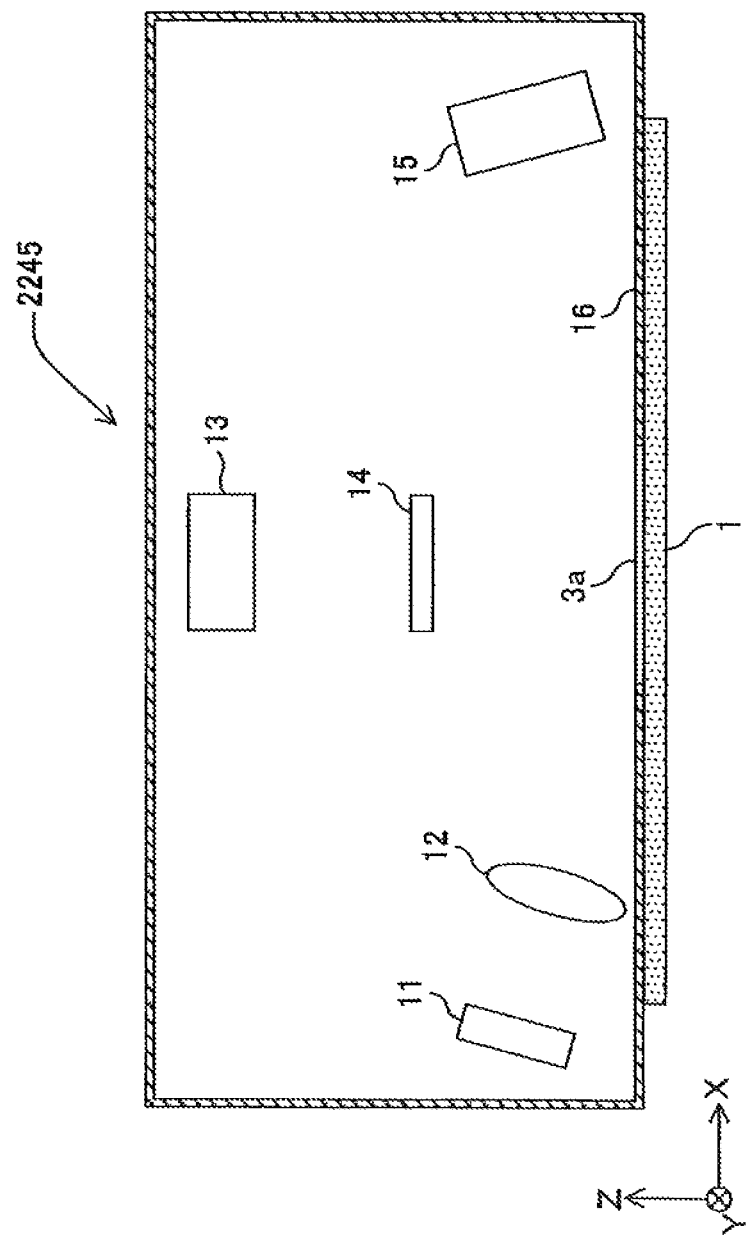
FIG. 31 is a diagram for explaining a configuration of an optical sensor in FIG. 30 in the eighth embodiment.

The optical sensor 2245 may include a light source 11, a collimate lens 12, two light receivers 13 and 15, a polarizing filter 14, and a dark box 16 for accommodating these component parts 12 through 15, as illustrated in FIG. 31.

The dark box 16 is regarded as a box member made of metal. The dark box 16 may be a box of aluminum. A black alumite process is performed on a surface of the dark box 16 to prevent influence due to disturbing light and stray light.

In an XYZ three dimensional orthogonal coordinate system, a direction orthogonal to a surface of the recording paper 1 corresponds to a Z-axis direction, and a plane parallel to the surface of the recording paper 1 corresponds to a XY plane. Thus, the optical sensor 2245 is arrange at +Z side of the recording paper 1.

Figure 32:
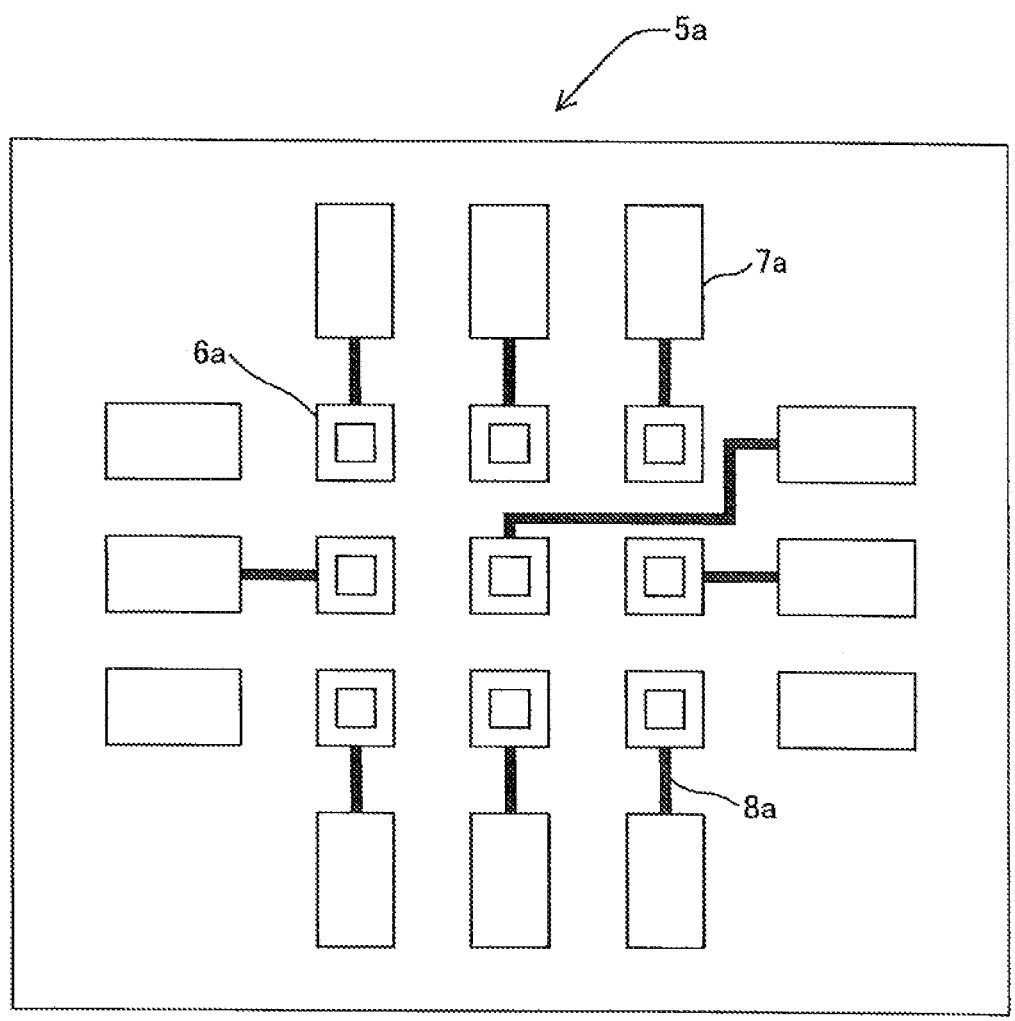
FIG. 32 is a diagram for explaining a surface emitting laser array in the eighth embodiment.

The light source 11 includes multiple emitting elements 6a. Each of the multiple emitting elements 6a may be a Vertical Cavity Surface Emitting Laser (VCSEL). That is, the light source 11 includes a surface emitting laser array (VCSEL array) 5a. As illustrated in FIG. 32, nine light emitting elements 6a (ch1 through ch9) are arranged in two dimensions, and are connected to electrode pads 7a by wiring members 8a.

Figure 33:
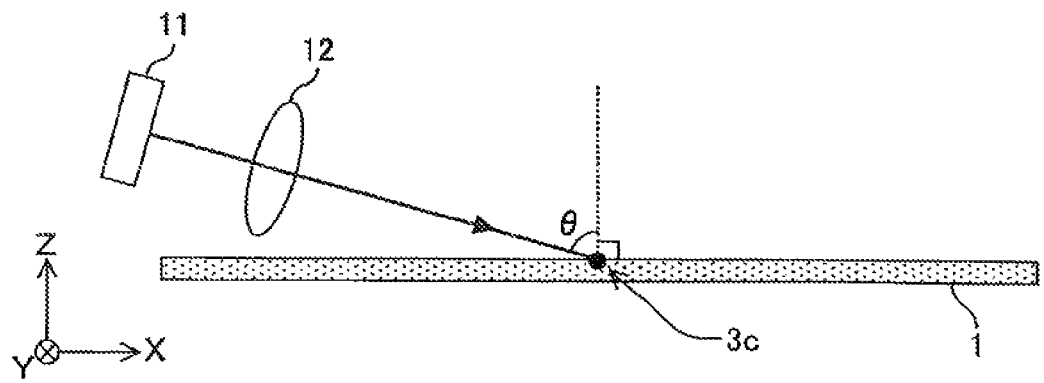
FIG. 33 is a diagram for explaining an incident angle of an incident light to a recording paper in the eighth embodiment.

The light source 11 is arranged so as to emit light of S-polarization to the recording paper 1. Also, as illustrated in FIG. 33, an incident angle θ of light flux from the light source 11 is 80° at an illumination center 3c on the recording paper 1. For a simplified explanation, the dark box 16 is omitted in FIG. 33.

The collimate lens 12 is arranged on a light path of the light flux emitted from the light source 11, and collimates the light flux to be parallel light. The light flux passing the collimate lens 12 illuminates the recording paper 1 through an opening part 3a provided to the dark box 16. In the following, a center in an illuminated area on the surface of the recording paper 1 is simply described as the illumination center 3c. Also, the light flux passing the collimate lens 12 is described as the irradiated light.

When the light enters an interface of a medium, a surface including the irradiated light and the normal line of the interface at an incident point is called an "incident surface". In a case in which the irradiated light is formed by multiple light beams, the incident surface exists for each of the multiple light beams. Accordingly, the incident surfaces, in which the multiple light beams are entered at the illumination center 3c, are simply called an incident surface of the recording paper 1. That is, planes parallel to an XZ-plane and including the illumination center 3c is regarded as the incident surface of the recording paper 1.

The polarizing filter 14 is arranged at +Z side of the illumination center 3c. The polarizing filter 14 is used to pass a P-polarized light and shield a S-polarized light. That is, instead of the polarizing filter 14, a polarization beam splitter including a equivalent function may be used.

Figure 34:
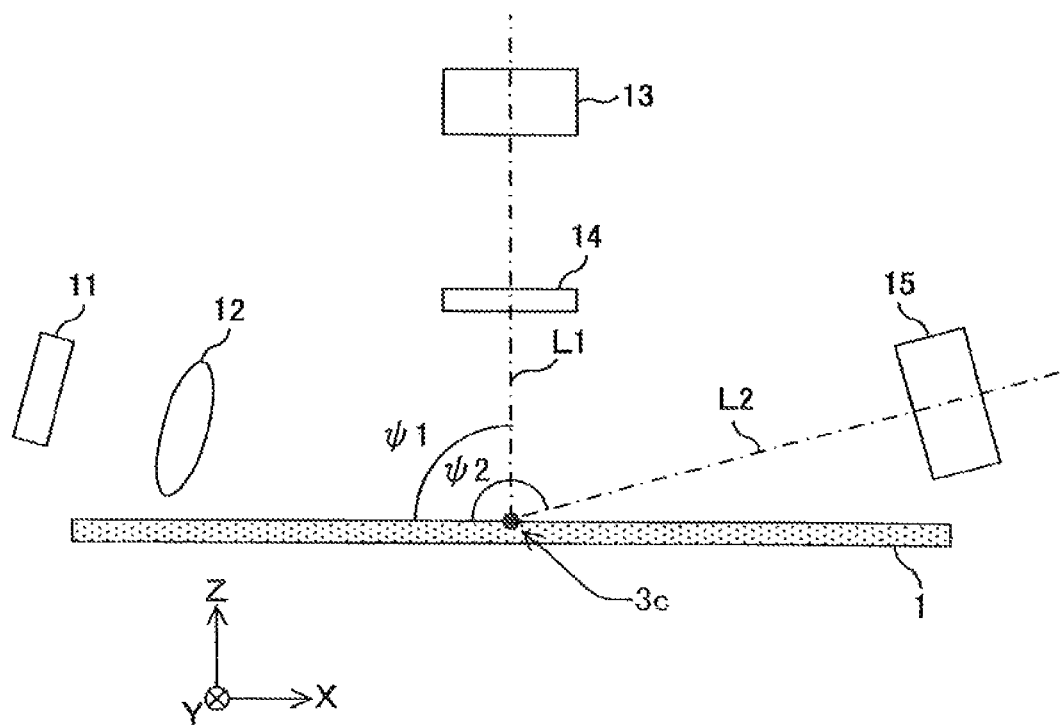
FIG. 34 is a diagram for explaining an arrangement location of two light receivers in the eighth embodiment.
Figure 35A:
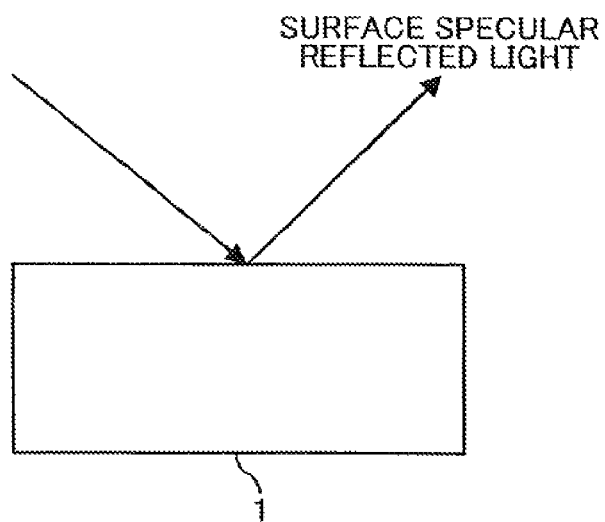
FIG. 35A is a diagram for explaining a surface specular reflected light in the eighth embodiment.
Figure 35B:
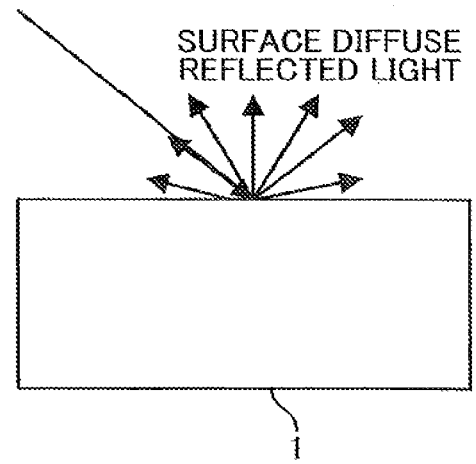
FIG. 35B is a diagram for explaining a surface diffuse reflected light in the eighth embodiment.
Figure 35C:
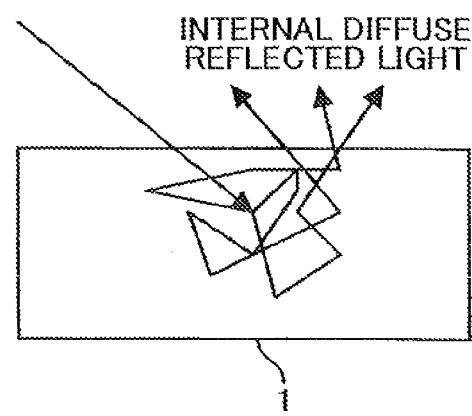
FIG. 35C is a diagram for explaining an internal diffuse reflected light in the eighth embodiment.
Figure 36:
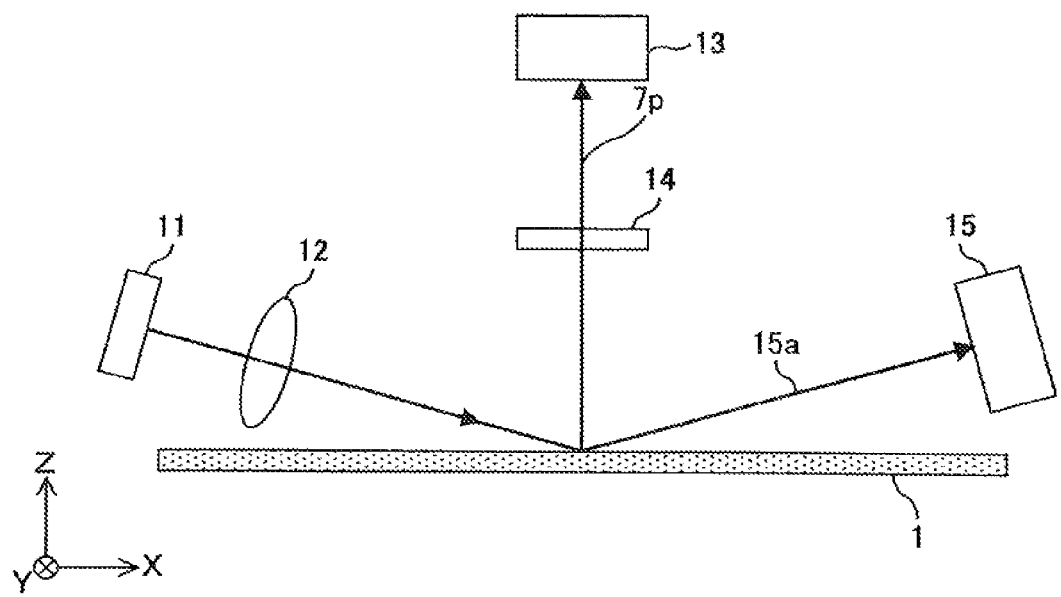
FIG. 36 is a diagram for explaining light respectively received by light receivers in the eighth embodiment.

The light receiver 13 is arranged at the +Z side of the polarizing filter 14. As illustrated in FIG. 34, an angle ψ1 formed by a line L1 and the surface of the recording paper 1 is 90°. The line L1 connects the illumination center 3c with a center between the polarizing filter 14 and the light receiver 13.

The light receiver 15 is arranged at +X side of the illumination center 3c in a X-axis direction. Accordingly, an angle ψ2 formed by a line L2 and the surface of the recording paper 1 is 170°. The line L2 connects the illumination center 3c and a center of the light receiver 15.

The centers of the light source 11, the polarizing filter 14, the light receivers 13 and 15, and the illumination center 3c exist on approximately the same plane.

The reflected light from the recording paper 1 when the recording paper 1 is illuminated may be considered to be separated into reflected light which is reflected at the surface of the recording paper 1 and reflected light which is reflected inside the recording paper 1. In the following, the reflected light regarded as light specularly reflected on the surface of the recording paper 1 corresponds to the surface specular reflected light, and the reflected light regarded as light diffusely reflected on the surface of the recording paper 1 corresponds to the surface diffuse reflected light (refer to FIG. 35A and FIG. 35B).

The surface of the recording paper 1 may be formed by flat portions and slope portions. Smoothness of the recording paper 1 is determined by a ratio of the flat portions and the slope portions. Light reflected on the flat portions becomes the surface specular reflected light, and light reflected on the slopes becomes the surface diffuse reflected light. The surface diffuse reflected light may be regarded as light completely reflected diffusely from the surface of the recording paper 1. It is considered that the surface diffuse reflected light may have isotropy in a reflected direction. The higher the smoothness, increases the light amount of the surface specular reflected light.

On the other hand, in a case in which the recording paper 1 is a general purposed print sheet, since reflected light from inside the recording paper 1 is multiply scattered in fabric inside the recording paper 1 and is the diffuse reflected light alone. In the following, the reflected light from inside the recording paper 1 may be called the internal diffuse reflected light (refer to FIG. 35C). Similar to the surface diffuse reflected light, the internal diffuse reflected light is also the reflected light which is completely reflected diffusely from the recording paper 1. It is considered that the surface diffuse reflected light may have isotropy in a reflected direction.

Polarization directions of the surface specular reflected light and the surface diffuse reflected light may be the same as a polarization direction of the incident light. In order to rotate the polarization directions on the surface of the recording paper 1, the incident light may be needed to be reflected on a surface inclined toward a rotation direction with respect to an optical axle of the incident light. Referring to FIG. 33 and FIG. 34, a center of the light source 11, the illumination center 3c, centers of the light receivers 13 and 15 are on the same place. The reflected light, in which the polarization directions are rotated on the surface of the recording paper 1, may not be directed to either of the light receivers 13 and 15.

On the other hand, the polarization direction of the internal diffuse reflected light is rotated with respect to the polarization direction of the incident light. It is considered that the light may be passed through the fabric optically rotated, and the polarization direction may be rotated.

Thus, the surface diffuse reflected light and the internal diffuse reflected light enter the polarizing filter 14. The polarization direction of the surface diffuse reflected light is regarded as the same S-polarization as the polarization direction of the incident light. Thus, the surface diffuse reflected light is shielded by the polarizing filter 14. On the other hand, the polarization direction of the internal diffuse reflected light is rotated with respect to the polarization direction of the incident light. Thus, a P-polarized component 7p is included in the internal diffuse reflected light passed at the polarizing filter 14. That is, the P-polarized component 7p included in the internal diffuse reflected light is received by the light receiver 13 (refer to FIG. 36).

The inventors have confirmed that the light amount of the P-polarized component 7p included in the internal diffuse reflected light has a correlation with the thickness or the density of the recording paper 1. The light amount of the P-polarized component 7p depends on a path length for the light to pass in the fabric of the recording paper 1.

The surface specular reflected light, and a portion of the surface diffuse reflected light and the internal diffuse reflected light enter the light receiver 15. That is, the surface specular reflected light mainly enters the light receiver 15.

Each of the light receiver 13 and the light receiver 15 outputs an electronic signal (photoelectric transfer signal) corresponding to a received light amount to the printer control device 2050. In the following, in a case of emitting the light flux from the light source 11 to the recording paper 1, a signal level in an output signal of the light receiver 13 is called "S1", and a signal level in an output signal of the light receiver 15 is called "S2".

Figure 37:
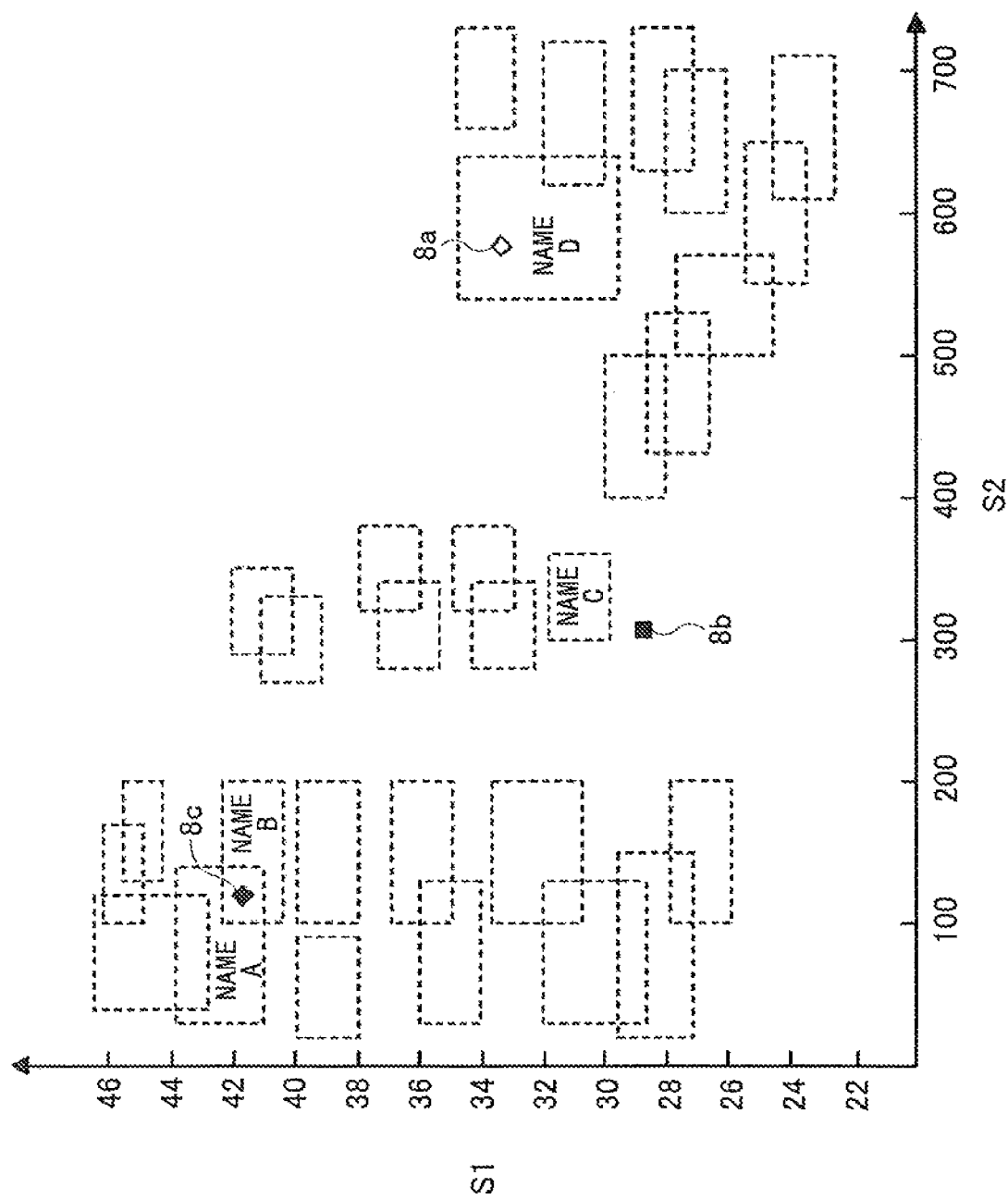
FIG. 37 is a diagram for explaining a relationship between signal levels S1 and S2 and a name of the recording paper in the eighth embodiment.

For each of multiple names of the recording papers 1 suitable for the color printer 2000a, values of the signal levels S1 and S2 are measured beforehand in a stage such as an adjustment stage or the like before the color printer 2000a is shipped. A measurement result is stored as the "recording paper determination table" in a ROM of the printer control device 2090. In FIG. 37, measured values of the signal levels S1 and S2 are illustrated for approximately 30 names related to the recording papers 1 domestically distributed. In FIG. 37, a dispersion range is illustrated by a dashed rectangle for each of the names. For example, if the measured values of the signal levels S1 and S2 indicate a value of a mark 8a, the name of the recording paper 1 is specified as a name D. If the measured values of the signal levels S1 and S2 indicate a value of a mark 8b, the name of the recording paper 1 is specified as a name C. If the measured values of the signal levels S1 and S2 indicate a value of a mark 8c, the name of the recording paper 1 is specified as either a name A or a name B. In this case, for example, a difference between an average value and the measured value of the name A is calculated. Also, a difference between an average value and the measured value of the name B is calculated. The name A or the name B having a smaller value as of the result of the calculation is specified as the name of the recording paper 1. Alternatively, if the name A is assumed as the name of the recording paper 1, dispersion including the measured value is re-calculated. Also, if the name B is assumed as the name of the recording paper 1, dispersion including the measured value is re-calculated. Then, the name A or the name B, in which the dispersion is smaller as a re-calculation result, may be selected as the name of the recording paper 1.

In a related art, it is attempted to identify the recording paper 1 by detecting the glossiness of the surface of the recording paper 1 from the light amount of the specular reflected light, and by detecting the smoothness of the surface of the recording paper 1 from a ratio of the light amounts of the specular reflection and the diffuse reflection. On the contrary, in the eighth embodiment, it is possible to detect information including the thickness and the density as other features of the recording paper 1 in addition to the glossiness and the smoothness of the surface of the recording paper 1. Thus, it is possible to expand identifiable types of the recording paper 1.

For example, in a case of using only information of the surface of the recording paper 1 used in a related method for identifying the recording paper 1, it is difficult to distinguish a matt coated paper from the plain paper. In the eighth embodiment, information inside the recording paper 1 is considered in addition to the information of the surface of the recording paper 1. Therefore, it becomes possible to not only distinguish between the plain paper and the matt coated paper but also distinguish among multiple names of the plain papers and among multiple names of the matt coated papers.

That is, in the eighth embodiment, it is possible to specify a target name from multiple of the recording papers 1 having different features of at least one of the glossiness, the smoothness, the thickness, and the density.

For each of the multiple names of the recording papers 1 suitable for the color printer 2000a, a development condition and a transfer condition suitable for each of the image formation stations are determined beforehand in the stage such as the adjustment stage or the like before the color printer 2000a is shipped. A determination result is stored as a "development and transfer table" in the ROM of the printer control device 2090.

When a power of the color printer 2000a is turned on, and when the recording paper 1 is supplied to the paper feed tray 2060, the printer control device 2090 performs a paper type specifying process. The paper type specifying process performed by the printer control device 2090 will be described in the following.

(1) The multiple light emitting elements 6a of the optical sensor 2245 are simultaneously lighted.

(2) The values of the signal levels S1 and S2 are acquired from the output signals of the light receiver 13 and the light receiver 15.

(3) The name of the recording paper 1 is specified from the values of the signal levels S1 and S2 acquired by referring to the recording paper determination table.

(4) Information indicating the specified name of the recording paper 1 is stored in a RAM, and the paper type specifying process is terminated.

When receiving a paint job request from a user, the printer control device 2090 reads out the information of the name of the recording paper 1 stored in the RAM, and acquires the development condition and the transfer condition which are the most suitable for the name of the recording paper 1, from the development and transfer table.

After that, the printer control device 2090 controls a developing device and a transfer device for each of the image formation stations depending on the most suitable development condition and transfer condition. For example, a transfer voltage and a toner quantity may be controlled. By this configuration, a high quality image is formed on the recording paper 1.

Next, a method for suppressing the speckle pattern will be described.

If a semiconductor laser is used for a light source of a sensor for detecting a surface state of the recording paper 1 from the reflected light amount, a coherent light emitted from the semiconductor laser are diffusely reflected at points on a rough surface such as the surface of the recording paper 1. Lights that are reflected at the points are interfered with each other, and the speckle pattern occurs.

Figure 38:
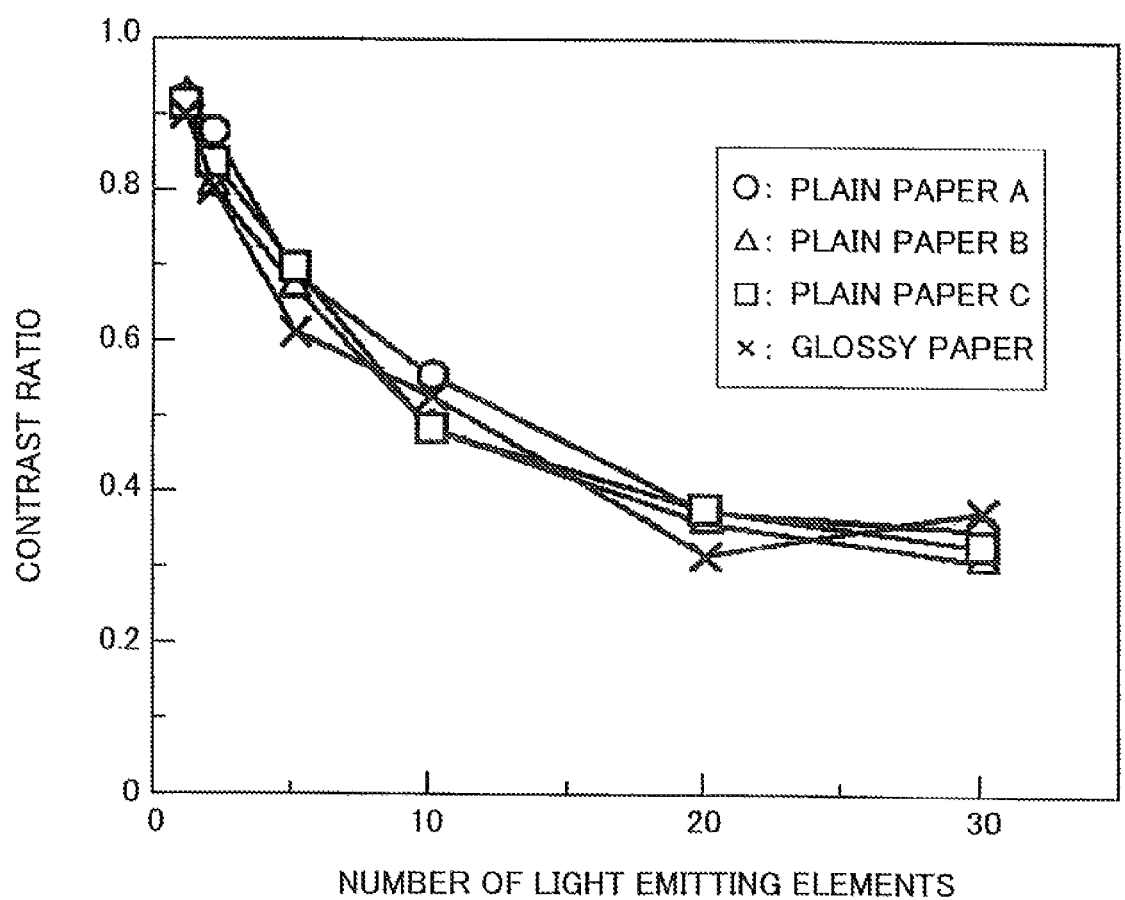
FIG. 38 is a diagram for explaining influence of the number of light emitting elements which affect a contrast ratio of the speckle pattern in the eighth embodiment.

The inventors have investigated a relationship between the number of the light emitting elements 6a and the contrast ratio of the speckle pattern in a case of using the surface emitting laser array (VCSEL array) 5a in which the light emitting elements 6a are arrayed in two dimensions (refer to FIG. 38). In the eighth embodiment, the contrast ratio is defined as a value in which a difference between a maximum value and a minimum value is normalized in an observed intensity of the speckle pattern.

Observation of the speckle pattern is performed by using a beam profiler, regarding a Y-axis direction (diffuse direction). The contrast ratio of the speckle pattern is calculated based on an observation result acquired by the beam profiler. As samples as observation targets, three types of plain papers (a plain paper A, a plain paper B, and a plain paper B) having different smoothness degrees and a glossy paper is used. The plain paper A is a paper in which the Oken type smoothness indicates 33 sec. The plain paper B is a paper in which the Oken type smoothness indicates 50 sec. The plain paper C is a paper in which the Oken type smoothness indicates 100 sec.

As illustrated in FIG. 38, when the number of the light emitting elements 6a is increased, the contrast ratio of the speckle pattern tends to decrease. Also, this tendency does not depend on the type of a paper.

Figure 39:
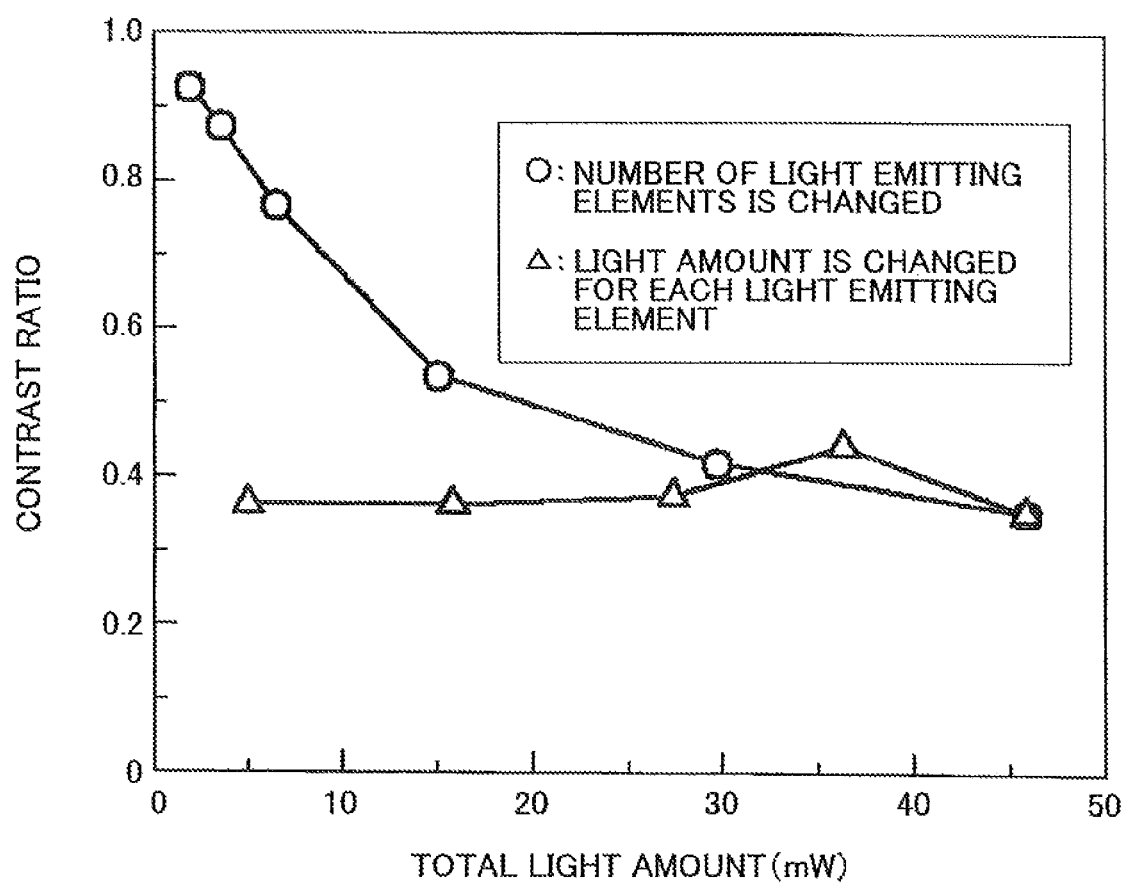
FIG. 39 is a diagram for explaining a relationship between the contrast ratio of the speckle pattern and a total light amount in a case in which the number of the light emitting elements is changed and in a case in which the light amount for each of the light emitting elements is changed in the eighth embodiment.

Moreover, the inventors performed an experimentation to confirm that an effect of decreasing the contrast ratio of the speckle pattern originated in an increase of the number of the light emitting elements 6a but did not originated in an increase of a total light amount (refer to FIG. 39).

FIG. 39 illustrates a change of the contrast ratio with respect to the total light amounts in a case of changing the number of the light emitting elements 6a while each light amount of the light emitting elements 6a is fixed (for example, 1.66 mW) and in a case of charging the light amount for each of the light emitting elements 6a while the number of the light emitting elements 6a is fixed to 30 elements.

In the case of changing the light amount for each of the light emitting elements 6a while the number of the light emitting elements 6a is fixed, the contrast ratio is approximately constant. On the contrary, in the case of changing the number of the light emitting elements 6a while each light amount of the light emitting elements 6a is fixed, if the light amount is less, that is, the number of the light emitting elements 6a is small, the contrast ratio is high. When the number of the light emitting elements 6a is increased, the contrast ratio gradually decreases. Accordingly, it is confirmed that the effect of decreasing the contrast ratio in the speckle pattern depends on the increase of the number of the light emitting elements 6a, but does not depend on the increase of the light amount.

Also, the inventors investigated whether it is possible to suppress the speckle pattern by varying the wavelength of the light emitted from the light source.

In the surface emitting laser (VCSEL), it is possible to control the wavelength of the light emitted by a driving current. When the driving current is changed, heat is generated in the VCSEL, and a refraction index is varied. Then, an effective resonator length is changed.

Figure 40:
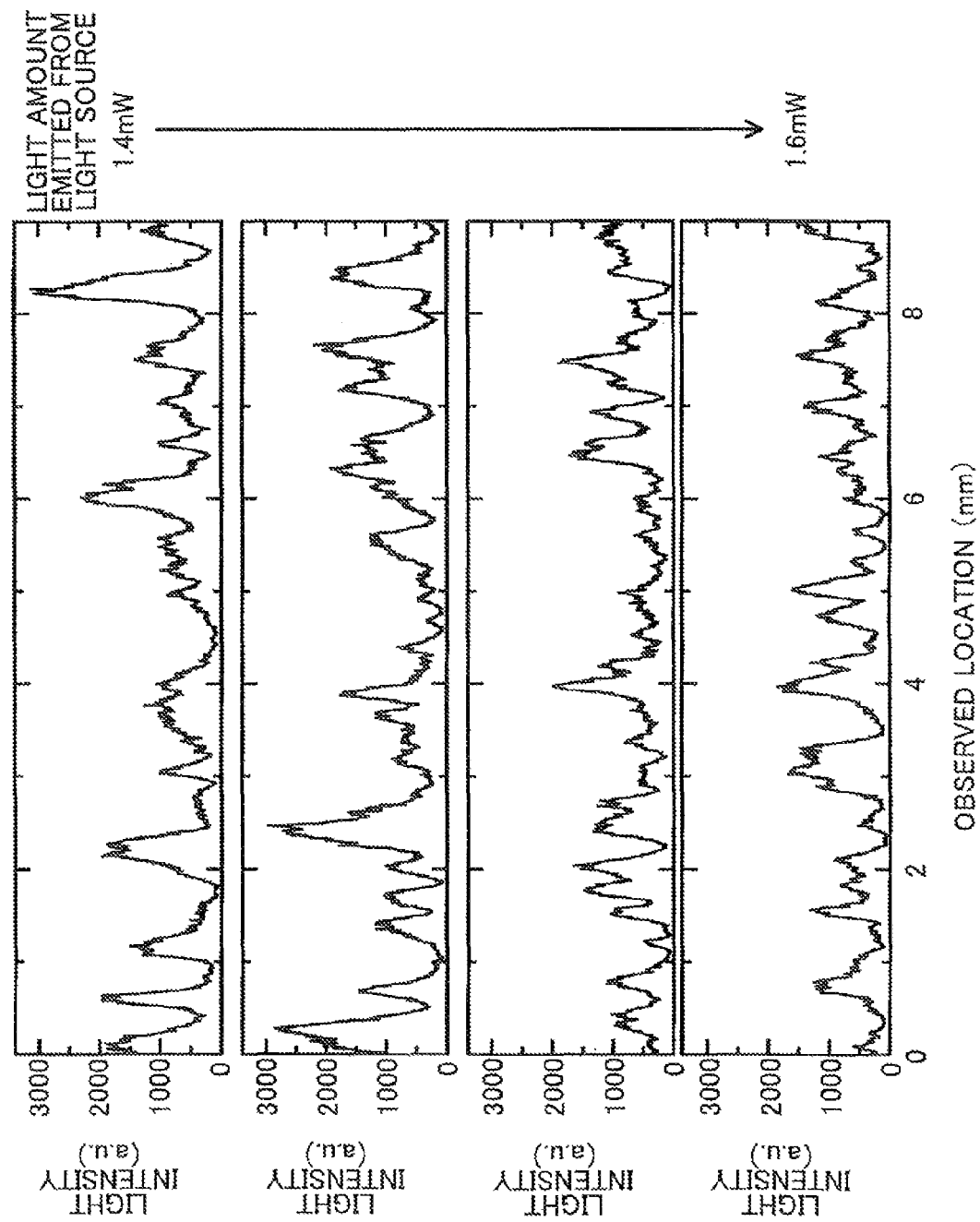
FIG. 40 is a diagram for explaining a light intensity distribution of the speckle pattern when a driving current of the light source is changed in the eighth embodiment.

FIG. 40 illustrates a light intensity distribution acquired by observing the speckle pattern by the beam profiler in a case in which the VCSEL is applied as the light source and an emitted light amount is changed from 1.4 mW to 1.6 mW by changing the driving current. As illustrated in FIG. 40, depending on the change of the driving current, the wavelength of the light emitted from the light source is changed. Thus, it is confirmed that the light intensity distribution is changed.

Figure 41:
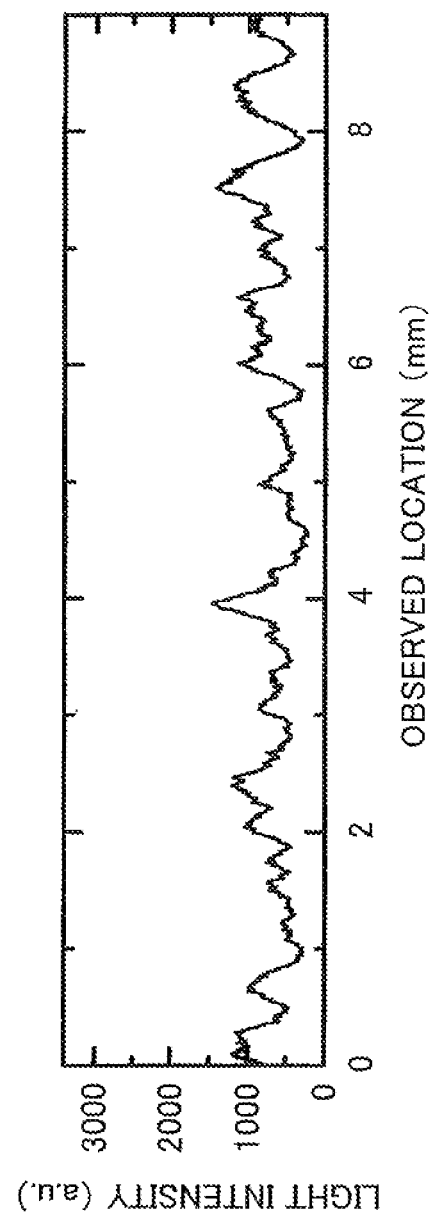
FIG. 41 is a diagram for explaining an effective light intensity distribution of the speckle pattern when the diving current of the light source is changed at higher speed in the eighth embodiment.

FIG. 41 illustrates an effective light intensity distribution in a case of charging the driving current at high speed. The light intensity distribution is the same as an average value of the light intensity distribution in multiple driving currents illustrated in FIG. 40. Thus, it is confirmed that a change of the light intensity is suppressed. The contrast ratio of the speckle pattern in the case of changing the driving current indicates 0.72, and the contrast ratio of the speckle pattern in the case of fixing the driving current indicates 0.96. Thus, the contrast ratio in the former case is suppressed to be lower than that in the latter case.

Accordingly, in a case of driving the surface emitting laser (VCSEL), for example, flow of the driving current may be controlled so as that a current value forms a triangular waveform in a temporal response. Therefore, it is possible to suppress the contrast ratio to be lower.

In the eighth embodiment, the light source 11 of the optical sensor 2245 includes the surface emitting laser array 5a in which nine light emitting elements 6a are arrayed in two dimensions. The CPU of the printer control device 2090 supplies the driving current of the triangular waveform to the surface emitting laser array 5a. By this configuration, the speckle pattern is suppressed. It is possible to detect an accurate reflected light amount. Accordingly, it is possible to improve precision of identifying the recording paper 1. That is, it is regarded that the speckle pattern is suppressed by temporality changing the wavelength of the emitted light.

Furthermore, by using the surface emitting laser array 5a, it is possible to easily perform an adjustment for collimating the irradiated light to be the parallel light.

It has been confirmed that the light amount of the P-polarization component 7p included in the internal diffuse reflected light is very small compared to the light amount of the light emitted to the recording paper 1. For example, when the incident angle θ indicates 80°, the light amount of the diffuse reflected light is approximately four figures smaller than the emitted light amount, and the light amount of the P-polarized component 7p included in the internal diffuse reflected light is further less than half the light amount of the diffuse reflected light.

In order to accurately detect the P-polarized component 7p included in the internal diffuse reflected light, it is preferable to increase an output of the light source and to receive the P-polarized component 7p included in the internal diffuse reflected light in a light receiving condition for acquiring an accurate P-polarized component 7p and a maximum detected amount.

The following is important in order to receive the P-polarized component 7p included in the internal diffuse reflected light accurately and at the maximum detected amount.

(1) The P-polarized component 7p included in the internal diffuse reflected light is not detected at least in a direction including the surface specular reflected light.

It is actually difficult to perfectly leave the S-polarization from the irradiated light. The reflected light on the surface of the recording paper 1 may include the P-polarized component 7p. In the direction including the surface specular reflected light, the P-polarized component 7p, which is originally included in the irradiated light and reflected on the surface of the recording paper 1, may become greater than the P-polarized component 7p included in the internal diffuse reflected light. If the polarizing filter 14 and the light receiver 13 are arranged in a direction including the surface specular reflected light, the reflected light amount including information of inside the recording paper 1 is not accurately detected.

It may be considered to use a polarizing filter having a higher extinction ratio, to perfectly pass the S-polarization for the irradiated light. In this case, the optical sensor becomes more expensive.

(2) The P-polarized component 7p included in the internal diffuse reflected light is detected in a normal direction of the illumination center on the recording paper 1.

Since the internal diffuse reflected light is regarded as a perfect diffuse reflected light, the reflected light amount with respect to a detection direction is approximated to a Lambert distribution, in which the reflected light amount becomes the greatest in the normal direction of the illumination center 3c. In a case in which the polarizing filter 14 and the light receiver 13 are arranged in the normal direction of the illumination center 3c, the S/N is high and the highest accuracy is obtained.

From the above explanations, the related art may be regarded as the following.

Japanese Laid-Open Patent Application No. H10-160687 discloses a sheet material quality discriminating device in which a material quality of sheet material is discriminated based on a light quantity specularly reflected on a surface of sheet material. That is, the sheet material is discriminated only based on an absolute light quantity of the specular reflected light, without considering inside a target object.

In a image forming apparatus disclosed in Japanese Laid-Open Patent Application No. 2006-062842, the light amount of the reflected light from a target object is detected in multiple directions. In this case, the glossiness is detected based on the ratio of the specular reflected light and the diffuse reflected light, and a paper type is determined, without considering inside a target object.

In an image forming apparatus disclosed in Japanese Laid-Open Patent Application No. 11-249353, the specular reflected light is divided into two polarized components, and the two polarized components are detected. Based on a light quantity difference between the two polarized components, the smoothness of the surface of a paper is acquired, and the paper type is determined. In this case, polarizations are utilized. However, the two polarized components are detected in a direction including the specular reflected light. Also, inside the target object is not considered.

In the above described related art, the non-coated paper, the coated paper, and the GHP sheet are simply determined. However, the name of the recording paper 1 is not specified.

In the method for determining the recording paper 1 in the eighth embodiment, a specifying method using the light amount of internally diffused light including information of the inside the recording paper 1, which has not been considered, is newly provided in addition to the above described related art.

In the specifying method in the eighth embodiment, it is possible to acquire information of the thickness or the density of the recording paper 1 in addition to the glossiness (smoothness) of the surface of the recording paper 1 in the related art, by receiving the reflected light at a appropriate location. Thus, it is possible to segment a specifying level in detail.

Apparently from the above explanations, in the eight embodiment, a light emitting system includes the light source 11, and the collimate lens 12. A first light detection system is formed by the light receiver 15, and a second light detection system is formed by the polarizing filter 14, and the light receiver 13.

It should be noted that in an apparatus for identifying surface property disclosed in Japanese Laid-Open Patent Application No. 2002-340518, and a printer apparatus disclosed in Japanese Laid-Open Patent Application No. 2003-292170, a surface of a recording member may be damaged, and a surface feature itself may be changed.

Moreover, for example, it may be possible to further segment the specifying level by additionally mounting various sensors such as a sensor for detecting the thickness of the recording member by using transmitted light, an ultrasonic sound, or the like, a sensor for detecting a resistance value of the recording member, a temperature sensor, in addition to a reflection type optical sensor. Disadvantageously, the number of component parts is increased. Thus, the optical sensor may cost more and a size of the optical sensor may become larger.

For a sensor to detect the surface state of a print sheet based on the reflected light amount, it is preferable to use the semiconductor laser as the light source 11, in order to improve the S/N. In this case, the speckle pattern is caused, when the light flux is emitted onto a rough surface such as the surface of the print sheet. The speckle pattern is different depending on a portion illuminated by the light flux. Dispersion of detector by the light receivers 13 and 15 is caused and accuracy is degraded. Accordingly, in general, the LED or the like has been conventionally used.

The optical sensor 2245 according to the eighth embodiment includes the light source 11, the collimate lens 12, the light receiver 13, the polarizing filter 14, the light receiver 15, the dark box 16, and the like.

Then, the light receiver 13 is arranged to receive the P-polarized component 7p included in the internal diffuse reflected light, and the light receiver 15 is arranged to mainly receive the surface specular reflected light.

In this case, it is possible to specify the name of the recording paper 1 based on an output signal of the light receiver 13 and an output signal of the light receiver 15.

As described above, by detecting the light amount of the P-polarized component 7p included in the internal diffuse reflected light, it becomes possible to separate the reflected light from inside the recording paper 1 at high accuracy. The reflected light has been difficult to separate due to its weak light. The reflected light from inside the recording paper includes information related to an inside state of the recording paper 1. By additionally considering the information, it becomes possible to improve the specifying level to a level of specifying the name which is difficult in the prior art.

Also, instead of combining various types of multiple sensors, the optical sensor 2245 is realized at a lower expense with a simplified configuration, and is minimized.

Therefore, it is possible to specify the name of the recording paper 1 in detail more than the related art, without causing the higher expense and the larger size.

Also, since the surface emitting laser array 5a is used as the light source 11, the polarizing filter 14 is not needed to form the irradiated light to be the linear polarization. Also, it is possible to easily make the irradiated light the parallel light, and also to realize a minimized light source including the multiple light emitting elements 6a. It is possible to realize the optical sensor 2245 in which the size is reduced and the expense is reduced.

The light source 11 includes the multiple light emitting elements 6a. By simultaneously lighting all of the multiple light emitting elements 6a, it is possible to increase the light amount of the P-polarized component 7p included in the internal diffuse reflected light.

The diffuse reflected light includes (A) "S-polarization reflected on the surface", (B) "S-Polarization reflected inside", and (C) "P-polarization reflected inside". In the diffuse reflected light, the "S-polarization reflected inside" is separated by the polarizing filter 14. By detecting its light amount, it is needed to further segment the specifying level. It is required to emit a greater light amount for the following reasons.

If the irradiated light is the S-polarization, a ratio of the "P-polarization reflected inside" in the diffuse reflected light (A+B+C) indicates approximately 40% at maximum. A cheaper polarizing filter, which is mounted in a general purpose sensor, has a lower transmission factor. Light is decreased by the polarizing filter at approximately 80%. The "P-polarization reflected inside" is attenuated and substantially becomes approximately 30%, when the "P-polarization reflected inside" is separated by the polarizing filter.

In the related art using the above described sensor, the type of the recording paper 1 is specified from two or three types (for example, the coated paper, a plastic sheet, and the like), depending on the light amount of the diffuse reflected light (A+B+C).

In the eighth embodiment, the type of the recording paper 1 is specified from at least ten types of recording papers 1 based on the "P-polarization reflected inside" alone. That is, in the eighth embodiment, it is possible to specify the type of the recording paper 1 in detail five times more than the related art specifying one from two types of the recording papers 1. Thus, a higher optical resolution is needed with the light amount smaller than the related art. If a photo diode (PD) with the higher optical resolution is used, it becomes possible to specify the type of the recording paper 1 with the smaller light amount. However, it may increase cost.

Accordingly, in the eighth embodiment, by increasing the emitted light amount, the higher optical resolution is acquired. In detail, the described above, since the light amount of the internal diffuser reflected light is decreased at approximately 30% substantial to the diffuse reflected light (A+B+C), the light amount of the irradiated light is required to be 3.1 times more than the related art. Moreover, since a paper determination is performed in detail five times more than the related art, the light amount, which is 3.3×5 times more than that in the related art, needed to emit. As described above, proportional to specifying more types of the recording papers 1, the light amount to emit is needed to be increased. In the eighth embodiment, in a case in which a non-polarized light source such as a LED is used to emit the S-polarization, light is needed to pass the polarizing filter to be the linear polarization (S-polarization) before the light is emitted. In this case, the cheaper polarizing filter as described above may be used. The light amount to emit onto the recording paper 1 becomes approximately 40% (=50% (cut portion of the P-polarization)×80% (decreased portion by the polarizing filter)) of the light amount emitted from the LED. Accordingly, in a case of a LED light source, the light amount to emit, which is 40 (=3.3×5/0.4) times greater than the related art, is needed. However, the light amount emitted from a cheaper LED may be approximately a few mW (1 mW as representative value). It is difficult to assure the light amount greater than 40 mW to 50 mw to emit. On the contrary, in the surface emitting laser array 5a, the multiple light emitting elements 6a are simultaneously lighted. Thus, it is possible to easily assure a desired light amount to emit. Accordingly, in the surface emitting laser array 5a, it is possible to assure the light amount for specifying the types of the recording papers 1 more than the related art.

Also, in the eighth embodiment, since the light source 11 includes the multiple light emitting elements 6a, by lighting the multiple light emitting elements 6a, compared with a case of lighting on only one of the multiple light emitting elements 6a, the contrast ratio of the speckle pattern of the reflected light is decreased. Thus, it is possible to improve an accuracy of specifying the type of the recording paper 1.

Furthermore, since the surface emitting laser array 5a is used, it is possible to emit the linear polarization which is more stable. By this configuration, it is possible to precisely detect the light amount of the P-polarized component 7p included in the internal diffuse reflected light.

Also, since a current temporally changing its value is used as the driving current of the surface emitting laser, it is possible to further reduce the contrast ratio of the speckle pattern.

Moreover, since the surface emitting laser array 5a for the light source 11, the polarizing filter for making the irradiated light the linear polarization is not required. Also, it is possible to easily make the irradiated light the parallel light, and to realize the light source 11 being minimized and including the multiple light emitting elements 6a. It is possible to realize the optical sensor 2245 being small sized and to reduce the cost of the optical sensor 2245.

The color printer 2000a according to the eighth embodiment includes the optical sensor 2245. As a result, it is possible to form a high quality image without increasing the cost and the size of the optical sensor 2245. Furthermore, it is possible to remove workload of manual settings and to overcome a printing failure.

Also, in the eighth embodiment, a case in which the light emitted onto the recording paper 1 is the S-polarization is described. The eighth embodiment is not limited to this case, and may be applied to a case in which the light emitted onto the recording paper 1 is the P-polarization. In this case, instead of using the polarizing filter 14, a polarizing filter for passing the S-polarization is used.

Figure 42:
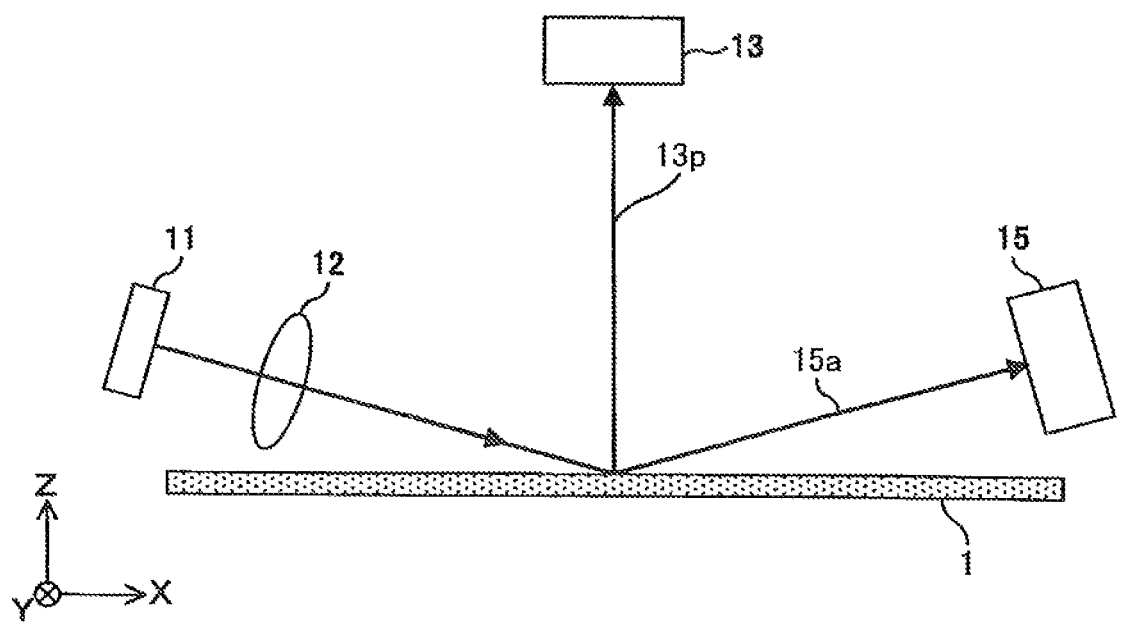
FIG. 42 is a diagram for explaining another configuration of the optical sensor in the eighth embodiment.

Moreover, in the eighth embodiment, in a case in which the specifying level of the optical sensor 2245 may be sufficient to specify one of the non-coated paper, the coated paper, and the OHP sheet, the polarizing filter 14 may not be arranged as illustrated in FIG. 42. By using the surface emitting laser array 5a, it is possible to emit the light, which has a greater light amount than a case of a single light emitting element, to emit onto the recording paper 1. It is possible to improve the S/N in the reflected light amount and to improve the specifying accuracy. In FIG. 42, reflected light 13p toward the light receiver 13 includes the surface diffuse reflected light and the internal diffuse reflected light. Reflected light toward the light receiver 15 is regarded as the surface specular reflected light.

Also, by simultaneously lighting the multiple light emitting elements 6a, the contrast ratio of the speckle pattern is reduced. It is possible to further detect the reflected light amount further accurately, and to improve the specifying accuracy.

Furthermore, in a case of using the surface emitting laser array 5a, it is possible to realize a higher density integration which has not been realized in a case of using the LED such as the related art. All laser beams are centralized in a vicinity of a light axis of the collimate lens 12, and angles of multiple light fluxes are made to be constant incident angles. Thus, the multiple light fluxes are made approximately parallel. It is possible to easily realize a collimate optical system.

Figure 43:
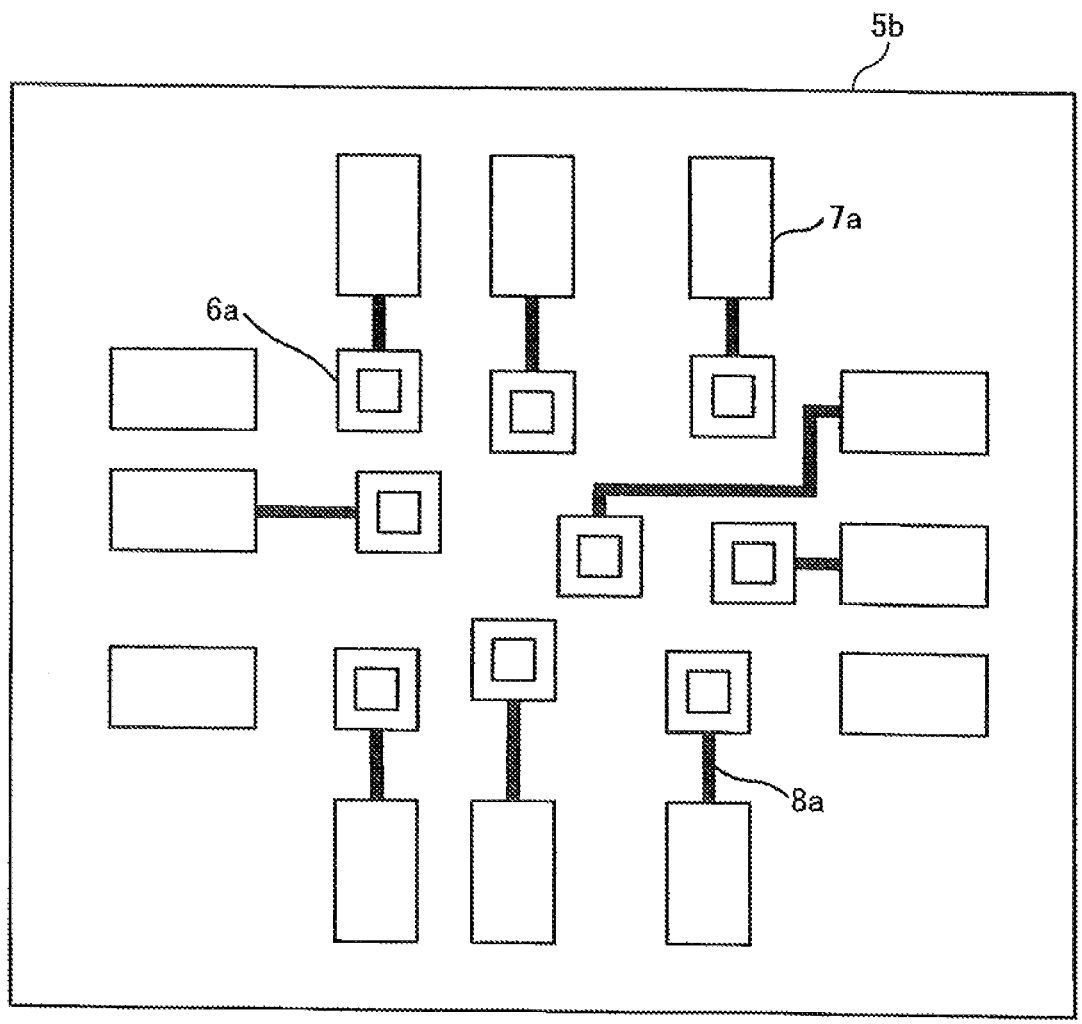
FIG. 43 is a diagram for explaining the surface emitting laser array in which light emitting elements are unequally spaced in the eighth embodiment.

Also, in the eighth embodiment, in the multiple light emitting elements 6a in a surface emitting laser array 5b as illustrated in FIG. 43, at least one interval among light emitting elements 6a may be different from other intervals. In this case, the regularity of the speckle pattern is disturbed. The contrast ratio of the speckle pattern is further reduced.

That is, it is preferable to provide different intervals between adjacent light emitting elements 6a in the surface emitting laser array 5b.

Figure 44:
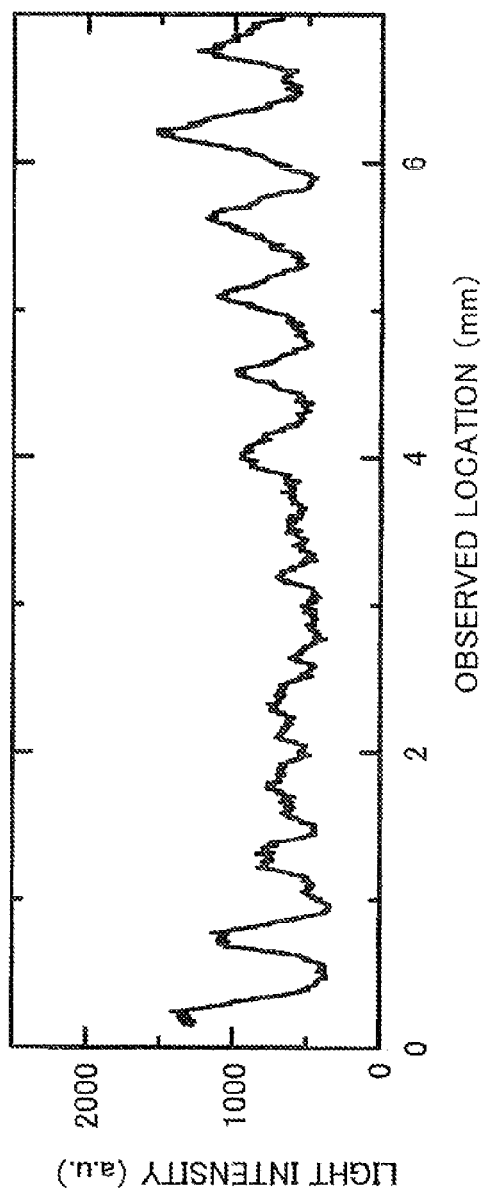
FIG. 44 is a diagram for explaining the light intensity distribution of the speckle pattern in which the light emitting elements are unequally spaced in the eighth embodiment.

FIG. 44 illustrates a light intensity distribution in which the speckle pattern is observed and acquired by the beam profiler in a case in which a light source including another surface laser array in which five light emitting elements are arrayed in one dimension and arranged at even intervals. In this case, a periodical fluctuation of the light intensity distribution, which corresponds to the regularity of an arrangement of the five light emitting elements, is confirmed. The contrast ratio indicates 0.64 in this case.

Figure 45:
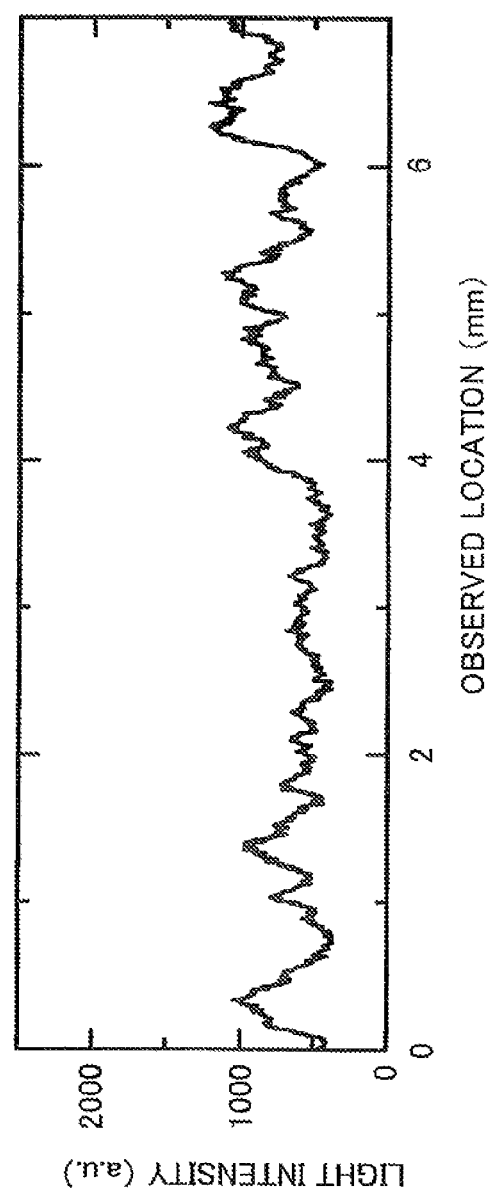
FIG. 45 is a diagram for explaining the light intensity distribution of the speckle pattern in which the light emitting elements are not equally space in the eighth embodiment.

Moreover, FIG. 45 illustrates the light intensity distribution in the light source including the surface emitting laser array in which the five light emitting elements are arrayed in one dimension and the light emitting elements are irregularly arranged with a ratio of 1.0:1.0:1.3:0.7, the light intensity distribution, which is acquired by observing the speckle pattern with a beam profiler. In this case, the periodical fluctuation of the light intensity distribution is suppressed. In this case, the contrast ratio indicates 0.56, and is reduced more than the case of arranging the light emitting elements with an equal interval.

As described above, for the surface emitting laser or the like including the multiple light emitting elements, the multiple light emitting elements are not equally spaced and are irregularly arranged. Thus, it is possible to further suppress the speckle pattern.

If the paper type may be erroneously determined due to the disturbing light and the stray light, a light detection system may be increased.

Figure 46:
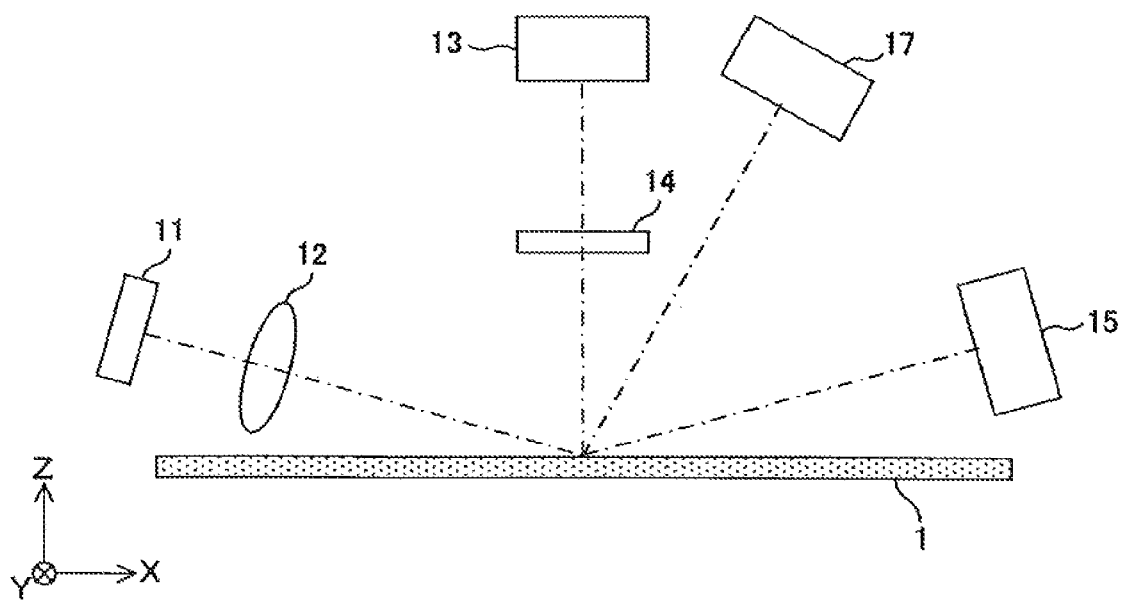
FIG. 46 is a diagram for explaining a first variation of the optical sensor in the eighth embodiment (part 1).

For example, as illustrated in FIG. 46, a light receiver 17 may be further included. The light receiver 17 may be arranged at a location where the surface diffuse reflected light and the internal diffuse reflected light are received.

Also, a center of the light source 11, the illumination center 3c, a center of the polarizing filter 14, a center of the light receiver 13, a center of the light receiver 15, and a center of the light receiver 17 exist on the same plane.

Figure 47:
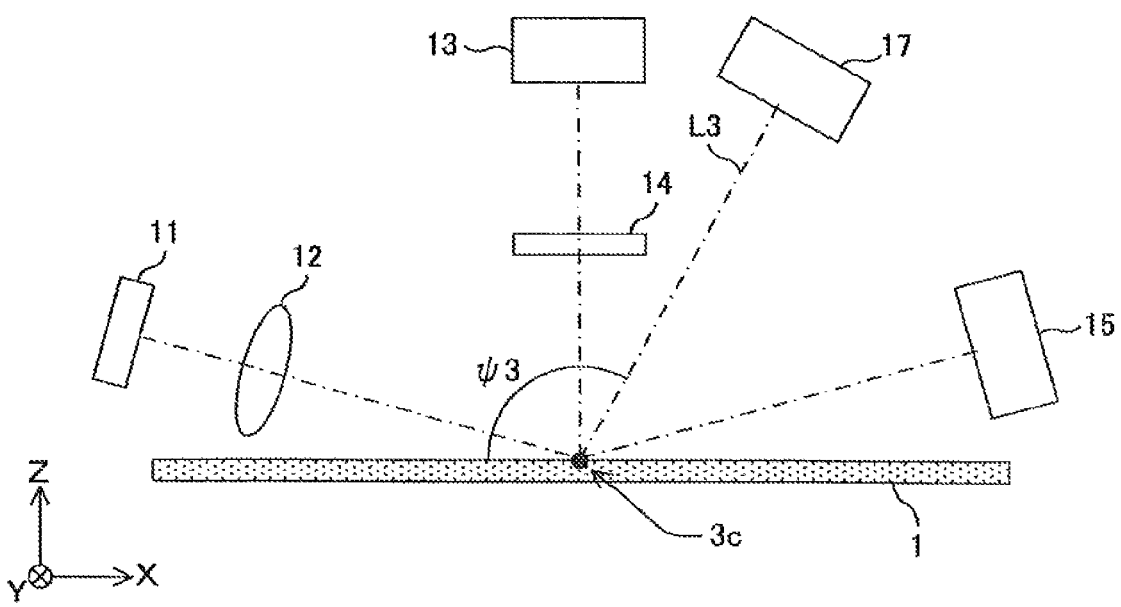
FIG. 47 is a diagram for explaining the first variation of the optical sensor in the eighth embodiment (part 2).

Thus, an angle ψ3 formed by a line L3 connecting between the illumination center 3c and the center of the light receiver 17 and the surface of the recording paper 1 is 120° (refer to FIG. 47).

The paper type specifying process performed by the printer control device 2090 in this case will be described in the following. When the light flux is emitted from the light source 11 onto the recording paper 1, a signal level of an output signal of the light receiver 17 is denoted by "S3".

(1) The multiple light emitting elements 6a of the optical sensor 2245 are simultaneously lighted.

(2) Values of the signal levels S1, S2, and S3 are acquired from output signals of the light receivers 13, 15, and 17.

(3) A value of the signal level S3 or S2 is acquired.

(4) By referring to the recording paper determination table, the name of the recording paper 1 is specified based on the acquired values of the signal levels S1 and S3 or S2.

(5) Information indicating the name of the recording paper 1 specified in the above item (4) is stored in the RAM, and the paper type specifying process in this case is terminated.

For each of multiple names of the recording papers 1 suitable for the color printer 2000a, the values of the signal levels S1 and S3 or S2 are measured beforehand in the stage such as an adjustment stage or the like before the color printer 2000a is shipped. A measurement result is stored as the "recording paper determination table" in the ROM of the printer control device 2090.

Figure 48:
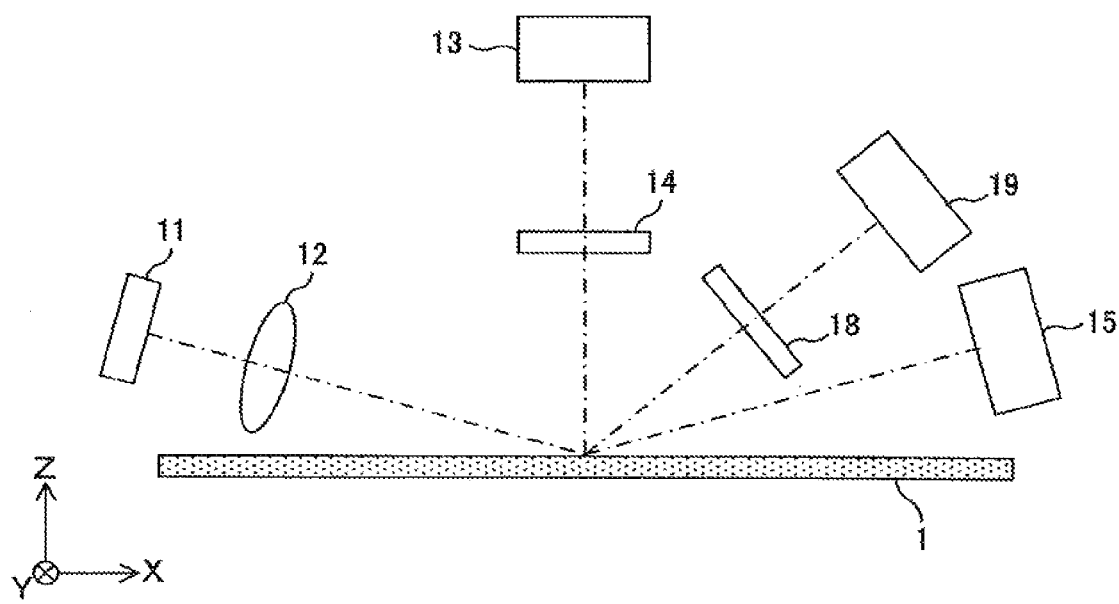
FIG. 48 is a diagram for explaining a second variation of the optical sensor in the eighth embodiment (part 1).

Also, for example, as illustrated in FIG. 48, the optical sensor 2245 may further include a polarizing filter 18 and the light receiver 19.

The polarizing filter 18 is arranged on light paths of the surface diffuse reflected light and the internal diffuse reflected light. The polarizing filter 18 is used to pass the P-polarization and shield the S-polarization.

The light receiver 19 is arranged on a light path of the light flux passing the polarizing filter 18. The light receiver 19 receives the P-polarized component 7p included in the internal diffuse reflected light.

Also, the center of the light source 11, the illumination center 3c, the center of the polarizing filter 14, the center of the light receiver 13, the center of the light receiver 15, the center of the polarizing filter 18, and a center of the light receiver 19 exist approximately on the same plane.

Figure 49:
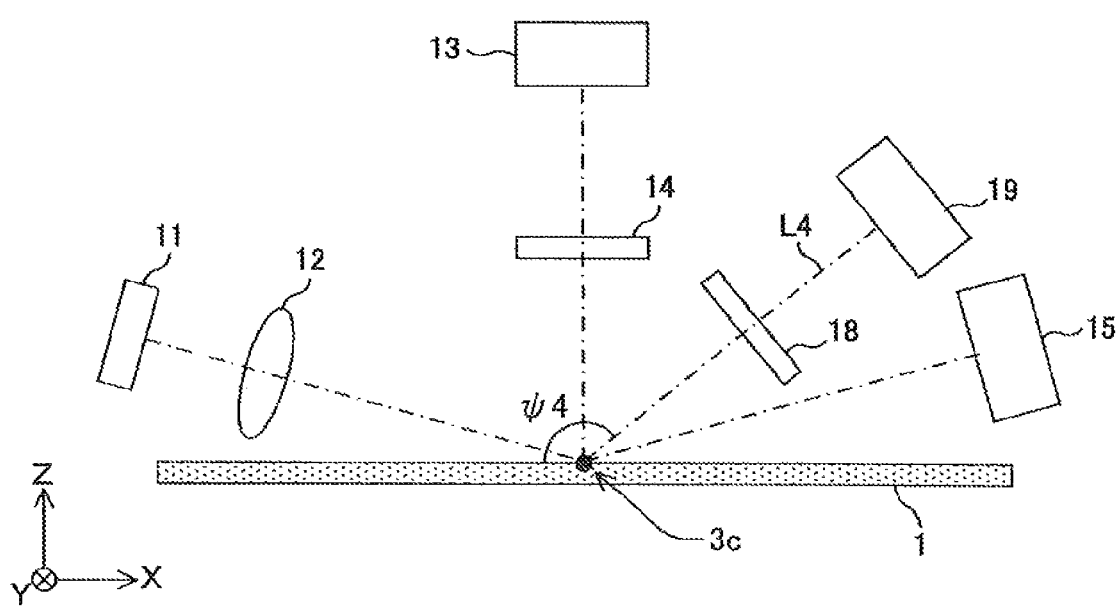
FIG. 49 is a diagram for explaining the second variation of the optical sensor in the eighth embodiment (part 2).

An angle ψ4 formed by a line L4 connecting between the illumination center 3c and the illumination center 3c, and the centers of the polarizing filter 18 and the light receiver 19 in 150° (refer to FIG. 49).

The paper type specifying process performed by the printer control device 2090 in this case will be described in the following. When the light flux is emitted from the light source 11 onto the recording paper 1, a signal level of an output signal of the light receiver 19 is denoted by "S4".

(1) The multiple light emitting elements 6a of the optical sensor 2245 are simultaneously lighted.

(2) Values of the signal levels S1, S2, and S4 are acquired from output signals of the light receiver 13, 15, and 19.

(3) A value of the signal level S4 or S1 is acquired.

(4) By referring to the recording paper determination table, the name of the recording paper 1 is specified based on the acquired value of the signal levels S4 or S1 and S2.

(5) Information indicating the name of the recording paper 1 specified if the above item (4) is stored in the RAM, and the paper type specifying process in this case is terminated.

For each of multiple names of the recording papers 1 suitable for the color printer 2000a, the values of the signal levels S4 or S1 and S2 are measured beforehand in the stage such as an adjustment stage or the like before the color printer 2000a is shipped. A measurement result is stored as the "recording paper determination table" in the ROM of the printer control device 2090.

Figure 50:
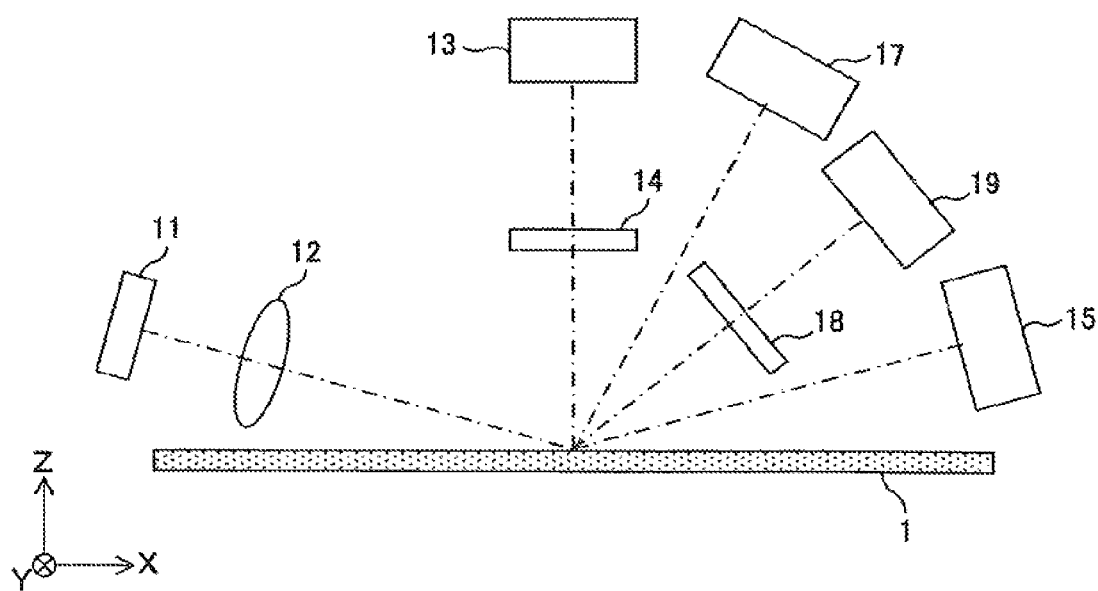
FIG. 50 is a diagram for explaining a third variation of the optical sensor in the eighth embodiment (part 1).
Figure 51:
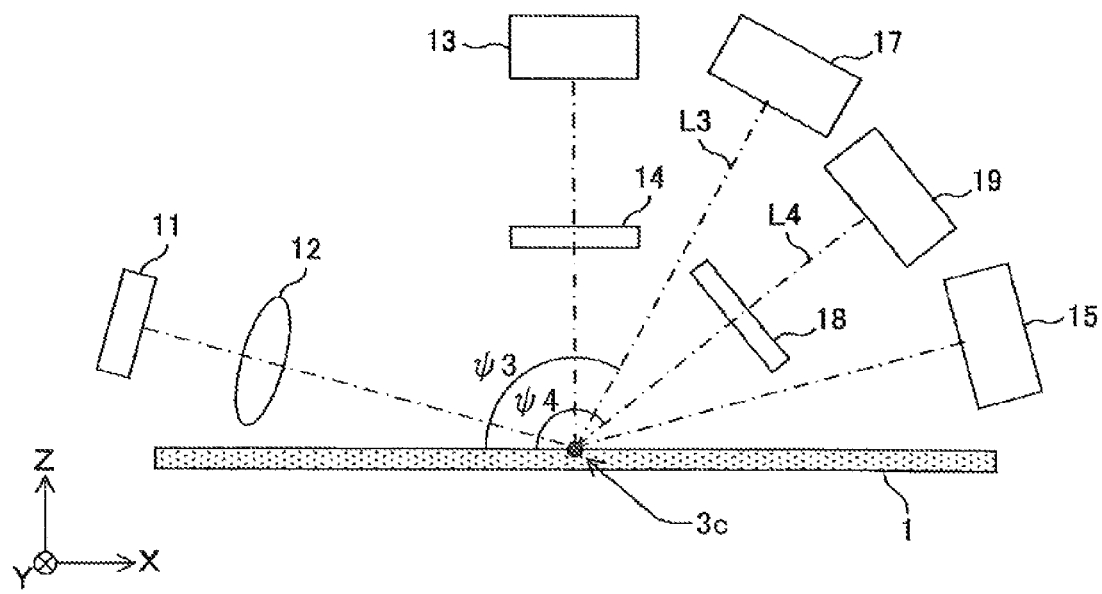
FIG. 51 is a diagram for explaining the third variation of the optical sensor in the eighth embodiment (part 2).

Also, for example, as illustrated in FIG. 50 and FIG. 51, the optical sensor 2245 may further include the light receiver 17, the polarizing filter 18, and the light receiver 19. That is, the optical sensor 2245 may further include a third light detection system formed by the light receiver 19, and a fourth light detection system formed by the polarizing filter 18 and the light receiver 19.

The paper type specifying process performed by the printer control device 2090 in this case will be described in the following.

(1) The multiple light emitting elements 6a of the optical sensor 2245 are simultaneously lighted.

(2) The values of the signal levels S1, S2, S3, and S4 are acquired from output signals of the light receivers 13, 15, 17, and 19.

(3) The values of the signal level S4 or S1 and the signal level S3 or S2 is acquired.

Figure 52:
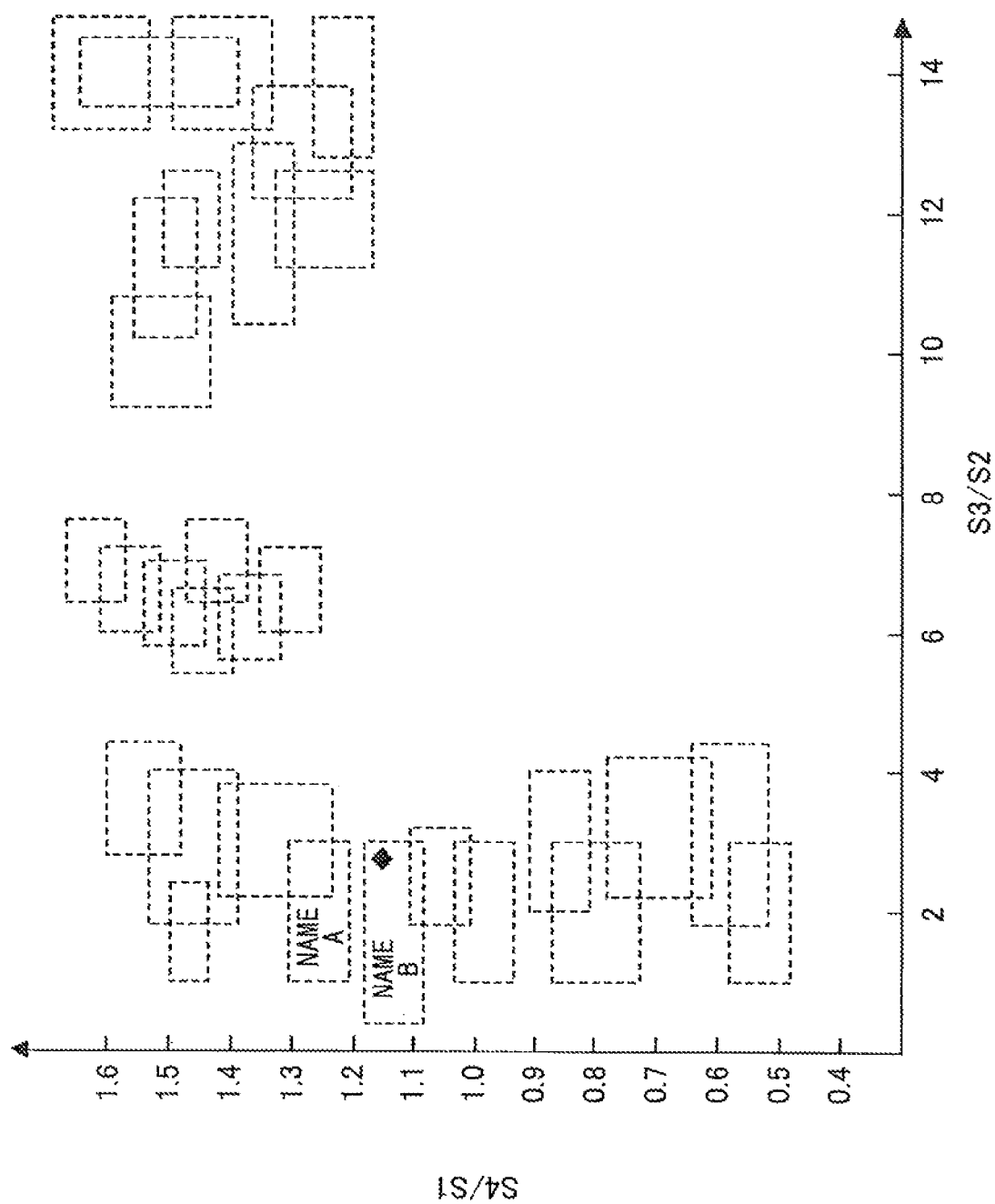
FIG. 52 is a diagram for explaining a relationship between a combination of a signal level S4 or S1 and a signal level S3 or S2, and the name of the recording paper in the eighth embodiment.

(4) By referring to the recoding paper determination table, the name of the recording paper 1 is specified based on the acquired values of the signal levels S4 or S1 and S2 (refer to FIG. 52).

(5) Information indicating the name of the recording paper 1 specified in the above item (4) is stored in the RAM, and the paper type specifying process in this case is terminated.

For each of multiple names of the recording papers 1 suitable for the color printer 2000a, the values of the signal levels S4 or S1 and S3 or S2 are measured beforehand in the stage such as an adjustment stage or the like before the color printer 2000a is shipped. A measurement result is stored as the "recording paper determination table" in the ROM of the printer control device 2090.

As described above, a plurality of light receiving systems each for detecting diffused light reflected in a different direction with each other are provided. By identifying the recording paper 1 by using calculated values such as values detected respectively by the light receiving systems, it is possible to certainly identify the recording paper 1 even if there are the disturbing light and the stray light.

Also, in this case, the printer control device 2090 may roughly specify the type of the recording paper 1 by using the signal levels S1 and S2. Then, the printer control device 2090 may specifically identify the name of the recording paper 1 by using the signal level S4 or S1 and the signal level S3 or S2.

A calculation method in this case uses the signal level S4 or S1. However, the calculation method in this case is not limited to this usage of the signal levels S4 or S1. Similarly, in a calculation method using the signal level S3 or S2, a usage of the signal level is not limited to the signal level S3 or S2.

Figure 53A:
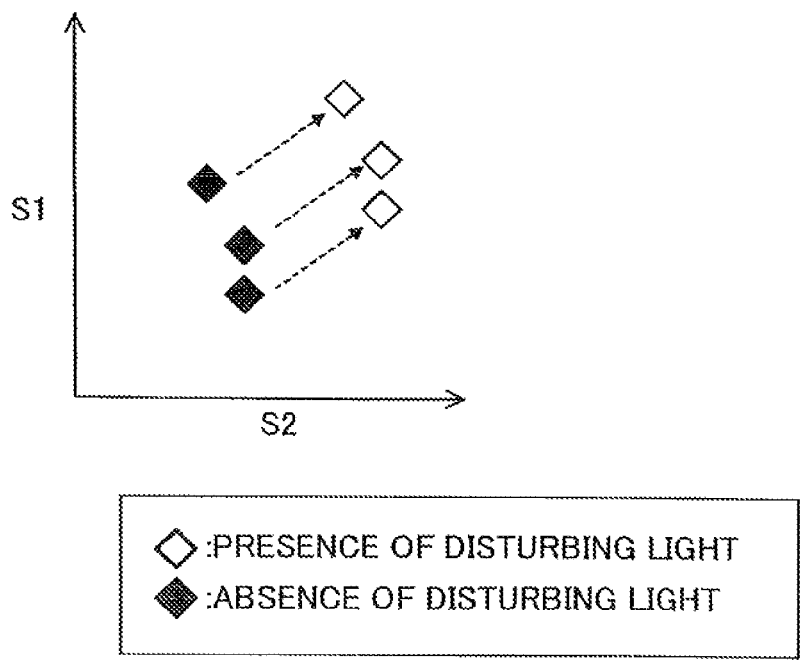
FIG. 53A and FIG. 53B are diagrams for explaining influence of distributing light in the eighth embodiment.
Figure 53B:
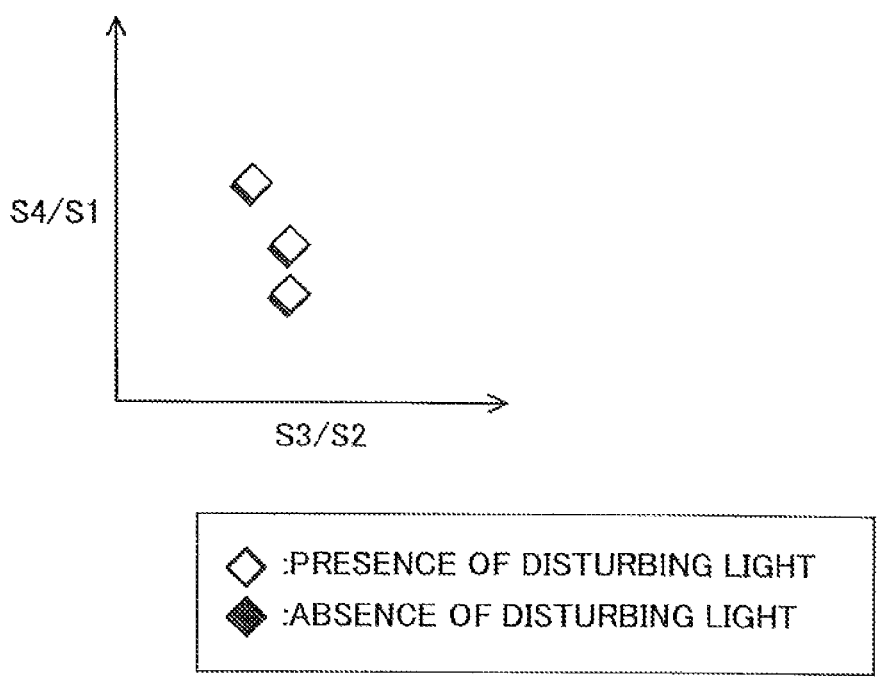

FIG. 53A illustrates an investigation result related to influence of the disturbing light in a case of specifying the paper type by using only the signal levels S1 and S2. FIG. 53B illustrates an investigation result related to influence of the disturbing light in a case of specifying the paper type by using the signal level S4 or S1 and the signal level S3 or S2. Apparent from FIG. 53A and FIG. 53B if there is the disturbing light, values respectively detected by the light receiving systems become greater. In the case of specifying the type of the recording paper 1 by using only the signal levels S1 and S2, the type may be erroneously specified. On the other hand, in the case of specifying the paper type by using the signal level S4 or S1 and the signal level S3 or S2, even if there is the disturbing light, the signal level S4 or S1 and the signal level S3 or S2 hardly change from a state in which there is no the disturbing light. Therefore, it is possible to specify a proper type of the recording paper 1.

In this case, the third light detection system may include multiple light receivers. Also, the fourth light detection system may include multiple polarizing filters.

For example, in a case in which the third light detection system may include two light receivers and the fourth light detection system may include two pairs of a polarizing filter and a light receiver, output levels of the light receivers are denoted by signal levels "S3" and "S5" in the third light detection system, and output levels of the light receivers are denoted by signal levels "S4" and "S6" in the fourth light detection system. A value calculated as (S4/S1+S6/S1) and a value calculated as (S3/S2+S4/S2) may be used, and the paper type may be specified. Also, a value of S4/S1, a value of S6/S1, a value of S3/S2, and a value of S5/S2 may be used, and the paper type may be specified.

The "recording paper determination table" depending on a calculation method used to specify the paper type is created beforehand in the stage such as an adjustment stage or the like, and is stored in the ROM of the printer control device 2090.

Figure 54:
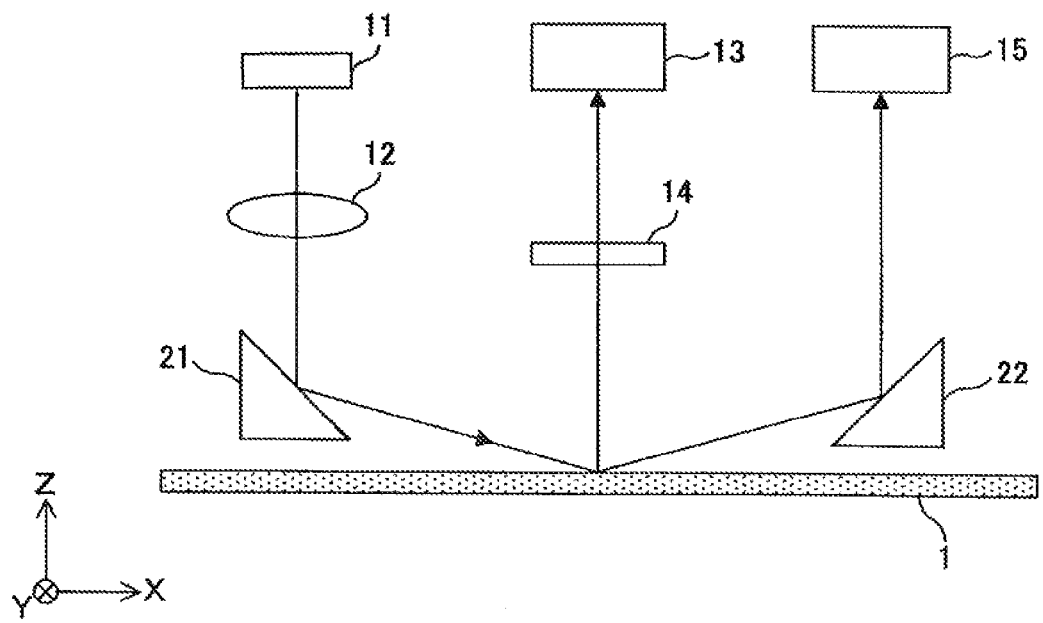
FIG. 54 is a diagram for explaining a fourth variation of the optical sensor in the eighth embodiment.

Moreover, in the eighth embodiment, as illustrated in FIG. 54 as an example, the optical sensor 2245 may further include two mirrors 21 and 22.

In this case, the light source 11 emits a light flux in a direction parallel to a Z-axis, and the collimate lens 12 is arranged so that an optical axis is parallel to the Z-axis.

Also, the mirror 21 reflects the light flux through the collimate lens 12 so that a light path of the light flux is bent.

The mirror 22 may be equivalent to the mirror 21, and is arranged at a location opposite the mirror 21 in a X-axis direction in which the opening part 3a (FIG. 31) is located between the mirrors 21 and 22. A light path of the surface specular reflected light from the recording paper 1 is bent so that its direction becomes parallel to the Z-axis.

The light receiver 15 is arranged at +Z side of the mirror 22 and receives the surface specular reflected light of which the light path is bent.

In this case, it is not required to provide support members for supporting the light source 11 and the light receivers 13 and 15 at a inclined state. Therefore, it is possible to realize the optical sensor 2245 with a lower cost and a reduced size.

Also, in a case of arranging more than three light receivers, by using mirrors for making respective directions of light fluxes toward the light receivers parallel to the Z-axis, it is possible to enhance a size reduction related to the optical sensor 2245.

Moreover, in the eighth embodiment, the configuration in which the light source 11 includes the multiple light emitting elements 6a is described above. The eighth embodiment is not limited to the case and may be applied to a configuration in which the light source 11 includes one light emitting element.

Figure 55:
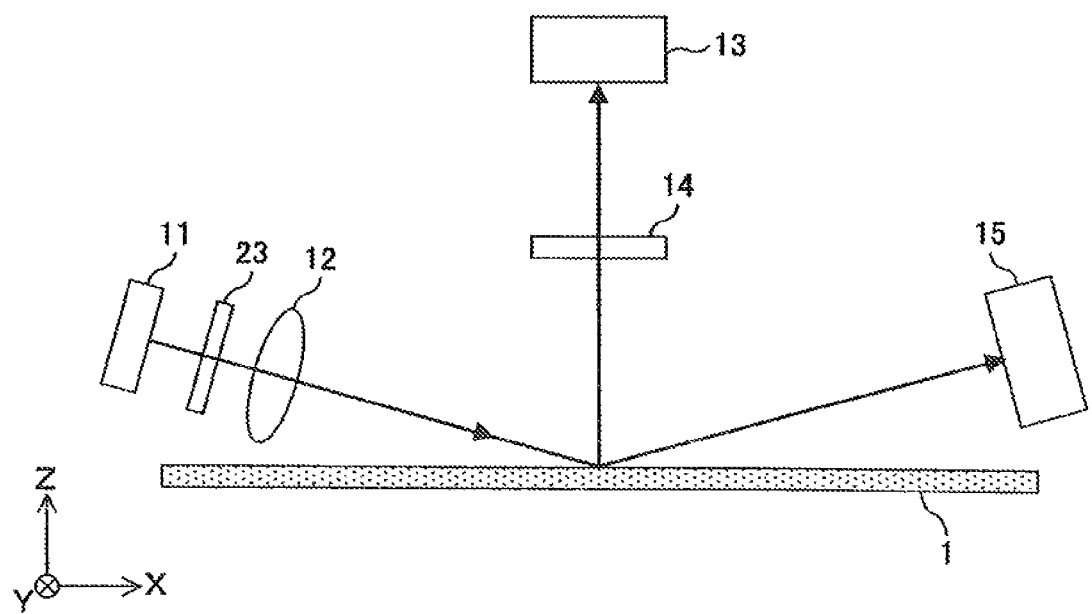
FIG. 55 is a diagram for explaining a fifth variation of the optical sensor in the eighth embodiment.

In the eighth embodiment, instead of the surface emitting laser array 5a or 5b, a conventional LD (Laser Diode) may be used. In this case, as a fifth variation illustrated in FIG. 55, a polarizing filter 23 is arranged to make the irradiated light the S-polarization.

Also, in the fifth variation, it is preferable to arrange a condensing lens in front of each of the light receivers 13 and 15. In this case, it is possible to reduce a change of the detected light amount.

It is important to reproduce a measurement for the optical sensor 2245 used to identify the recording paper 1 based on the reflected light amount. For the optical sensor 2245 used to identify the recording paper 1 based on the reflected light amount, a measurement system is arranged in a condition in which a measurement plane and the surface of the recording paper 1 are on the same plane when a measurement is performed. However, the surface of the recording paper 1 is inclined or lifted due to arcuation, vibration, and the like. Thus, the surface of the recording paper 1 may not be on the same plane as the measurement plane. In this case, the reflected light amount is charged, and a stable detailed determination is difficult to be performed. In the following, as an example, the specular reflected light will be described.

FIG. 56A illustrates a case in which a measurement plane 9a and the surface of the recording paper 1 are on the same plane. In this case, a light detection system 315 receives the specular reflected light.

FIG. 56B illustrates a case in which the surface of the recording paper 1 is inclined at an angle $\alpha$ with respect to the measurement plane 9a. In this case, if the location relationship between a light emission system and the light detection system 315 is the same as that in the case illustrated in FIG. 56A, the light detection system 315 receives light in a direction displaced at an angle $2\alpha$ from a specular reflection direction. The reflected light intensity distribution moves along the displacement. If the distance from a center location of the irradiation area to the light detection system 315 in denoted by L, the light detection system 315 receives light at a position displaced at an angle L=tan 2α. Also, an actual incident angle is displaced at the angle α from the incident angle θ with respected the perpendicular line 9b. The angle θ is regulated. A reflectance from the recording paper is varied. A change of the detected light amount is caused. As a result, it becomes difficult to identify the recording paper 1 in detail.

Moreover, FIG. 56C illustrates a case in which the surface of the recording paper 1 is displaced by distance d in height with respective to the measurement plane 9a, that is, a case in that the surface of the recording paper 1 is displaced in the Z-axis direction. In this case, if the location relationship between the light emission system and the light detection system 315 is the same as that in the case illustrated in FIG. 56A, since the reflected light intensity distribution moves along a displacement, the light detection system 315 receives light at a position displaced at an angle 2d×sin θ from a specular reflected light position. A change of the detected light amount is caused. As a result, it becomes difficult to identify the recording paper 1 in detail.

In cases illustrated in FIG. 56B and FIG. 56C, the condensing lens is arranged in front of the light detection system 115 with respect to a movement amount so as to certainly detect the specular reflected light. It is possible to correspond to a case in which the reflected light intensity distribution moves, by condensing the light fluxes.

Alternatively, by using a sufficiently large sized photo diode (PD) which is the light receiving area for the light receivers 13, 15, 17, 15, and the like, by narrowing a beam diameter for the irradiated light, it is possible to overcome a problem in which the surface of the recording paper 1 and the measurement plane are on the same plane.

Also, by using multiple photo diodes being arrayed in each of the light receivers 13, 15, 17, 19, and the like, a configuration having a sufficient large light receiving area with respect to a movement amount of the reflected light intensity distribution may be applied. In this case, even if the reflected light intensity distribution moves, a maximum signal of signals respectively detected by the multiple photo diodes may be regarded as a signal of the specular reflected light. In a case in which the multiple photo diodes are arrayed, by reducing the light receiving area for each of the multiple photo diodes, it is possible to reduce a fluctuation of an output due to a displacement between the specular reflected light and a center of the light receiving area.

In the above, the specular reflection is described. For the surface diffuse reflection and the internal diffuse reflection, the change of the detected light amount is caused due to the displacement between the measurement plane 9b and the surface of the recording paper 1. In each case for the surface diffuse reflection and the internal diffuse reflection, the same manner may be applied as the specular reflection.

In the eighth embodiment, a case of one paper feed tray 2060 is described. The number of the paper feed tray 2060 is not limited to one, and may be multiple. In this case, the optical sensor 2245 may be arranged for each of a plurality of paper feed trays 2060.

Also, in the eighth embodiment, the name of the recording paper 1 may be specified while being conveyed. In this case, the optical sensor 2245 may be arranged in a vicinity of a conveying path. For example, the optical sensor 2245 may be arranged in the vicinity of the conveying path between the feeding roller 2054 and the pair of registration rollers 2056.

Moreover, a target object identified by the optical sensor 2245 in the above described embodiments may not be limited to the recording paper 1.

In the eighth embodiment, the color printer 2000a is described above as the image forming apparatus. The eighth embodiment is not limited to the color printer 2000a, and may be applied to an optical plotter, a digital copier, or the like.

Alternatively, in the eighth embodiment, the color printer 2000a as the image forming apparatus is described above. The eighth embodiment is not limited to the color printer 2000a.

Also, the optical sensor 2245 may be applicable for another image forming apparatus in which an image is formed by jetting an ink onto the recording paper 1.

Figure 57:
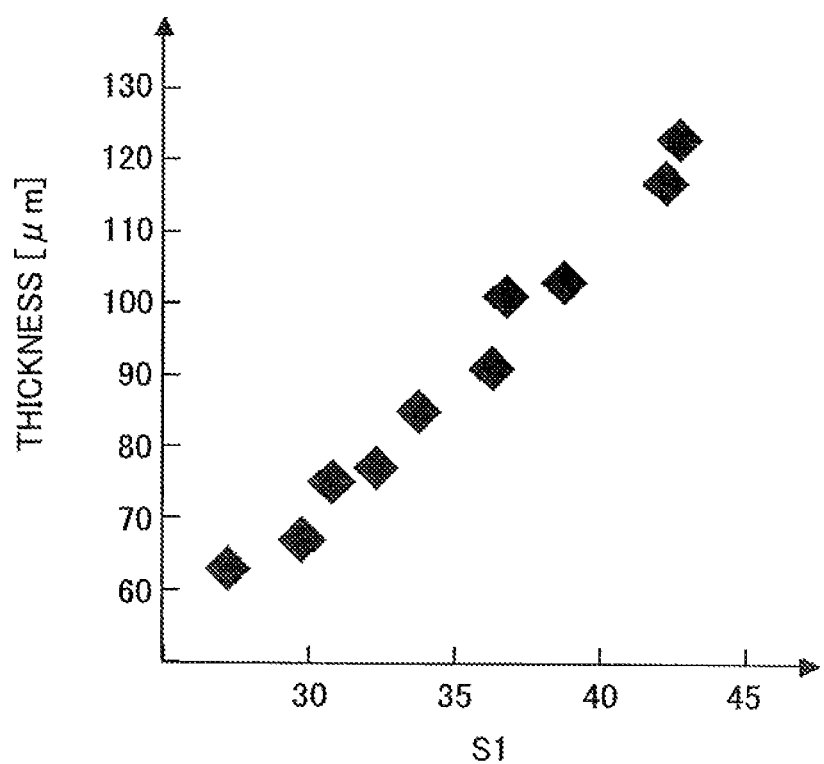
FIG. 57 is a diagram for explaining a relationship between thickness and the signal level S1 in the eighth embodiment.

It should be noted that the optical sensor 2245 is applicable to detect the thickness of the target object (refer to FIG. 57). In the related art, a thickness sensor may be a transmission-type sensor. Optical systems are always arranged symmetrically at the target object. For the optical systems, supporting members or the like are required. On the other hand, in the optical sensor 2245 in the eighth embodiment, the thickness is detected by the reflected light. The optical systems may be arranged at one side of the target object. Thus, it is possible to reduce the number of component parts and to realize the optical sensor 2245 with the lower cost and the reduced size. The optical sensor 2245 is suitable to be arranged inside the image forming apparatus in which the thickness of the target object is detected.

Figure 58:
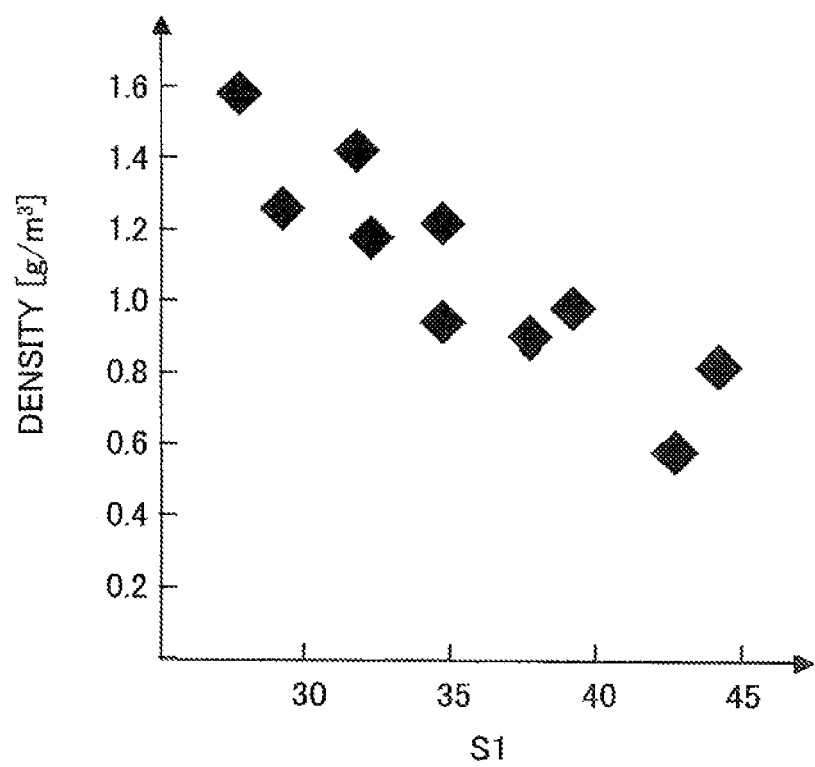
FIG. 58 is a diagram for explaining a relationship between a density and the signal level S1 in the eighth embodiment.

Moreover, it is possible to apply the optical sensor 2245 for a density detection of the target object (refer to FIG. 58). In the configuration in the related art, a density sensor may be a transmission-type sensor. The optical systems are always arranged symmetrically at the target object. For the optical systems, the supporting members or the like are required. On the other hand, in the optical sensor 2245 in the eighth embodiment, the density is detected by the reflected light. The optical systems may be arranged at one side of the target object. Thus, it is possible to reduce the number of component parts and to realize the optical sensor 2245 with the lower cost and the reduced size. The optical sensor 2245 is suitable to be arranged inside the image forming apparatus in which the density of the target object is detected.

In the above described embodiments, an optical sensor may include multiple measurement systems each configured to include a light emission system configured to emit first light of a linear polarization in a first polarization direction to a recording medium; a specular reflected light detection system configured to detect specular reflected light which is specularly reflected from the recording medium in the first light emitted from the light emission system; and a diffuse reflected light detection system configured to include an optical device for passing second light in a second polarization direction perpendicular to the first polarization direction, to detect diffuse reflected light which is diffusely reflected from the recording medium in the first light emitted from the light emission system.

Also, in the optical sensor, an angle, which is formed by a first component parallel to the recording medium of first emitted light emitted from one system of the multiple light emission system to the recording medium and a second component parallel to the recording medium of second emitted light emitted from another system of the multiple light emission system to the recording medium, may be equal to or greater than 90° and is equal to or less than 180°.

In the optical sensor, an angle, which is formed by a first component parallel to the recording medium of first emitted light emitted from one system of the multiple light emission system to the recording medium and a second component parallel to the recording medium of second emitted light emitted from another system of the multiple light emission system to the recording medium, may be 90° or 180°.

In the optical sensor, the emission system may include a light source, and a light path changing element which bends a light path of a light flux from the light source toward the incident direction.

The optical sensor may include a light path changing element configured to bend a path of light reflected on the target object.

An image forming apparatus for forming an image on the recording medium may include the above described optical sensor.

The image forming apparatus may include an adjustment device configured to specify a type of the recording medium based on an output of the optical sensor, and to adjust an image formation condition to correspond to a specified type.

The image forming apparatus may include an adjustment device configured to specify smoothness of the recording medium based on an output of the optical sensor, and to adjust an image formation condition to correspond to a specified smoothness.

The image forming apparatus may include an adjustment device configured to specify thickness of the recording medium based on an output of the optical sensor, and to adjust an image formation condition to correspond to a specified thickness.

The image forming apparatus may include an adjustment device configured to specify density of the recording medium based on an output of the optical sensor, and to adjust an image formation condition to correspond to a specified density.

The present invention is not limited to the specifically disclosed embodiments, and variations and modifications may be made without departing from the scope of the invention.

The present application is based on Japanese Priority Application No. 2010-263079 filed on Nov. 26, 2010, No. 2011-056234 filed on Mar. 15, 2011, No. 2011-159527 filed on Jul. 20, 2011, and No. 2011-171101 filed on Aug. 4, 2011, the entire contents of which are hereby incorporated by reference.

The invention claimed is:

1. An optical sensor, comprising:
a light emission system configured to emit an irradiated light of a linear polarization in a first polarization direction toward a surface of a target object having a sheet shape from an incident direction which is inclined with respect to a normal direction of the surface;
a light detection system configured to include a light detector arranged on a light path of a diffuse reflected light which is diffusely reflected from an incident plane on the target object, the light detector receiving light passed by an optical element which passes a linear polarization component of a second polarization direction perpendicular to the first polarization direction; and
an additional detection system configured to include an additional light detector arranged on a light path of a different diffuse reflected light which is diffusely reflected from the incident plane on the target object without passing the optical element,
wherein the light detection system and the additional detection system are arranged on paths different from a light path of the specular reflected light which is emitted from the light emission system and is specularly reflected from the target object.

2. The optical sensor as claimed in claim 1, wherein the optical element and the light detector of the light detection system are arranged on a light path of the diffuse reflected light which is diffusely reflected in a normal direction of the surface of the target object.

3. The optical sensor as claimed in claim 1, further comprising a processing part configured to specify the target object based on an output of the light detector and an output of another light detector arranged on a light path of the specular reflected light which is emitted from the light emission system and is specularly reflected from the target object.

4. The optical sensor as claimed in claim 1, further comprising:
a processing part configured to specify the target object based on a ratio of an output of the additional light detector and the additional detection system and an output of another light detector arranged on a light path of the specular reflected light which is emitted from the light emission system and is specularly reflected from the target object.

5. The optical sensor as claimed in claim 1, further comprising:
a third detection system configured to include another light detector arranged on a light path of the diffuse reflected light which is diffusely reflected from the incident plane on the target object, said another light detector receiving light passed by an additional optical element which passes the linear polarization of the second polarization direction perpendicular to the first polarization direction.

6. The optical sensor as claimed in claim 1, further comprising:
a processing part configured to specify the target object based on an output of the light detector, an output of the additional light detector, and an output of another light detector arranged on a light path of the specular reflected light which is emitted from the light emission system and is specularly reflected from the target object.

7. The optical sensor as claimed in claim 1, further comprising at least one of a light path changing element that bends a path of light from the light source toward the incident direction and a light path changing element that bends a path of light reflected on the target object toward at least one light detector.

8. The optical sensor as claimed in claim 1, wherein the light emission system includes a surface emitting laser as the light source.

9. An image forming apparatus for forming an image on the recording medium, comprising the optical sensor as claimed in claim 1.

* * * * *